United States Patent
Giliyar et al.

(10) Patent No.: US 11,590,147 B2
(45) Date of Patent: Feb. 28, 2023

(54) 17-HYDROXYPROGESTERONE ESTER-CONTAINING ORAL COMPOSITIONS AND RELATED METHODS

(71) Applicant: Lipocine Inc., Salt Lake City, UT (US)

(72) Inventors: Chandrashekar Giliyar, Plymouth, MN (US); Srinivasan Venkateshwaran, Salt Lake City, UT (US); Basawaraj Chickmath, Minneapolis, MN (US); Satish Nachaegari, Holladay, UT (US); Nachiappan Chidambaram, Sandy, UT (US); Mahesh V. Patel, Salt Lake City, UT (US)

( * ) Notice: Subject to any disclaimer, the term of this patent is extended or adjusted under 35 U.S.C. 154(b) by 0 days.

(21) Appl. No.: 16/927,891

(22) Filed: Jul. 13, 2020

(65) Prior Publication Data
US 2021/0169900 A1    Jun. 10, 2021

Related U.S. Application Data

(63) Continuation of application No. 16/055,594, filed on Aug. 6, 2018, now abandoned, which is a continuation of application No. 15/190,109, filed on Jun. 22, 2016, now abandoned.

(60) Provisional application No. 62/295,951, filed on Feb. 16, 2016, provisional application No. 62/183,031, filed on Jun. 22, 2015.

(51) Int. Cl.
*A61K 31/57* (2006.01)
*A61K 9/20* (2006.01)
*A61K 9/00* (2006.01)
*A61K 9/14* (2006.01)

(52) U.S. Cl.
CPC ............ *A61K 31/57* (2013.01); *A61K 9/0053* (2013.01); *A61K 9/14* (2013.01); *A61K 9/20* (2013.01); *A61K 9/2086* (2013.01)

(58) Field of Classification Search
CPC ...................................................... A61K 31/57
See application file for complete search history.

(56) References Cited

U.S. PATENT DOCUMENTS

| | | |
|---|---|---|
| 3,164,520 A | 1/1965 | Huber |
| 3,541,209 A | 11/1970 | Neumann |
| 4,196,188 A | 4/1980 | Besins |
| 4,230,702 A | 10/1980 | Eckert et al. |
| 4,439,432 A | 3/1984 | Peat |
| 5,057,319 A | 10/1991 | Gottwald et al. |
| 5,140,021 A | 8/1992 | Maxson et al. |
| 5,314,882 A | 5/1994 | Pantic et al. |
| 5,543,150 A | 8/1996 | Bologna et al. |
| 5,620,705 A | 4/1997 | Dong et al. |
| 5,633,011 A | 5/1997 | Dong et al. |
| 5,645,856 A | 7/1997 | Lacy et al. |
| 5,770,227 A | 6/1998 | Dong et al. |
| 5,948,766 A | 9/1999 | Milan et al. |
| 6,086,916 A | 7/2000 | Agnus et al. |
| 6,096,338 A | 8/2000 | Lacy et al. |
| 6,117,450 A | 9/2000 | Dittgen et al. |
| 6,294,192 B1 | 9/2001 | Patel et al. |
| 6,500,814 B1 | 12/2002 | Hesch |
| 6,544,553 B1 | 4/2003 | Hsia et al. |
| 6,602,521 B1 | 8/2003 | Ting et al. |
| 6,656,929 B1 | 12/2003 | Agnus et al. |
| 6,866,865 B2 | 3/2005 | Hsia et al. |
| 6,923,988 B2 | 8/2005 | Patel et al. |
| 7,431,941 B2 | 10/2008 | Besins et al. |
| 7,473,687 B2 | 1/2009 | Hoffman et al. |
| 7,884,093 B2 | 2/2011 | Creasy et al. |
| 7,943,602 B2 | 5/2011 | Bunschoten et al. |
| 7,976,871 B2 | 7/2011 | Vaya et al. |

(Continued)

FOREIGN PATENT DOCUMENTS

| | | |
|---|---|---|
| CA | 2512989 A1 | 8/2004 |
| CA | 2789238 A1 | 9/2011 |

(Continued)

OTHER PUBLICATIONS

Nutrition facts and calories for Grapefruit juice (published 2018). (Year: 2018).*
Aufrere et al.; "Progesterone: An Overview and Recent Advances;" Journal of Pharmaceutical Sciences; (Jun. 1976); pp. 783-800; vol. 65, No. 6.
De Lignieres; "Oral Micronized Progesterone;" Clinical Therapeutics; (Jan. 1999); pp. 41-60; vol. 21, No. 1.
Defranco et al.; "Vaginal Progesterone is Associated with a Decrease in Risk for Early Preterm Birth and Improved Neonatal Outcome in Women with a Short Cervix: A Second Analysis from a Randomized, Double-Blind; Placebo-Controlled Trial;" Ultrasound in Obstetrics and Gynecology; (Oct. 2007); pp. 697-705; vol. 30, No. 5.

(Continued)

*Primary Examiner* — Theodore R. Howell
*Assistant Examiner* — George W Kosturko
(74) *Attorney, Agent, or Firm* — Michael R. Schramm

(57) ABSTRACT

The present invention provides for bioavailable oral dosage forms containing esters of 17-hydroxyprogesterone as well as related methods. The oral dosage forms can be formulated for pregnancy support and can include a therapeutically effective amount of an ester of 17-hydroxyprogesterone and a pharmaceutically acceptable carrier. In another embodiment, a pharmaceutically acceptable oral dosage form for pregnancy support is provided. The pharmaceutically acceptable oral dosage can include a therapeutically effective amount of an ester of 17-hydroxyprogesterone and a pharmaceutically acceptable carrier. The oral dosage form can, when measured using a USP Type-II dissolution apparatus in 900 mL of deionized water with 0.5 (w/v) of sodium lauryl sulfate at 50 RPM at 37° C., release at least 20 wt % of the dose of the ester of 17-hydroxyprogesterone after 60 minutes, or in the alternative release at least 20 wt % more after 60 minutes than an equivalently dosed oral dosage form without the carrier.

20 Claims, 3 Drawing Sheets

(56) References Cited

U.S. PATENT DOCUMENTS

| | | | |
|---|---|---|---|
| 8,133,507 B2 | 3/2012 | Yum et al. | |
| 8,828,981 B2 | 9/2014 | Creasy et al. | |
| 8,951,996 B2* | 2/2015 | Giliyar | A61K 9/2059 |
| | | | 514/170 |
| 9,358,298 B2* | 6/2016 | Giliyar | A61P 17/06 |
| 9,358,299 B2* | 6/2016 | Giliyar | A61P 17/06 |
| 9,364,547 B2* | 6/2016 | Giliyar | A61P 17/10 |
| 9,399,069 B2* | 7/2016 | Giliyar | A61K 9/2013 |
| 10,022,384 B2* | 7/2018 | Giliyar | A61Q 11/00 |
| 2002/0131988 A1 | 9/2002 | Foster et al. | |
| 2003/0077297 A1 | 4/2003 | Chen et al. | |
| 2003/0236236 A1 | 12/2003 | Chen et al. | |
| 2004/0052824 A1 | 3/2004 | Abou Chacra-Vernet et al. | |
| 2004/0131553 A1 | 7/2004 | Besse | |
| 2004/0266025 A1 | 12/2004 | Hickok et al. | |
| 2005/0181041 A1 | 8/2005 | Goldman | |
| 2006/0009509 A1 | 1/2006 | Grubb et al. | |
| 2006/0275360 A1 | 12/2006 | Ahmed et al. | |
| 2008/0188829 A1 | 8/2008 | Creasy | |
| 2009/0098200 A1 | 4/2009 | Temtsin Krayz et al. | |
| 2009/0123534 A1 | 5/2009 | Besins et al. | |
| 2009/0264395 A1 | 10/2009 | Creasy | |
| 2011/0152840 A1 | 6/2011 | Lee et al. | |
| 2011/0262502 A1* | 10/2011 | Lee | A61P 33/00 |
| | | | 424/46 |
| 2011/0312927 A1 | 12/2011 | Nachaegari et al. | |
| 2011/0312928 A1 | 12/2011 | Nachaegari et al. | |
| 2012/0148675 A1 | 6/2012 | Chickmath et al. | |
| 2013/0023505 A1 | 1/2013 | Garfield et al. | |
| 2013/0029947 A1 | 1/2013 | Nachaegari et al. | |
| 2013/0029957 A1* | 1/2013 | Giliyar | A61P 5/00 |
| | | | 514/177 |
| 2014/0271882 A1 | 9/2014 | Giliyar et al. | |
| 2014/0377317 A1 | 12/2014 | Giliyar et al. | |
| 2015/0165049 A1 | 6/2015 | Giliyar et al. | |

FOREIGN PATENT DOCUMENTS

| | | | |
|---|---|---|---|
| CN | 1398590 A | 2/2003 | |
| CN | 1446540 A | 10/2003 | |
| CN | 1509720 A | 7/2004 | |
| CN | 1623550 A | 6/2005 | |
| CN | 103826640 A | 5/2014 | |
| JP | 2004155780 A | 6/2004 | |
| JP | 2006524238 A | 10/2006 | |
| JP | 2014521660 A | 8/2014 | |
| RU | 2225207 C2 | 3/2004 | |
| RU | 2340345 C2 | 12/2008 | |
| WO | WO 90/008537 A1 | 8/1990 | |
| WO | WO 93/012797 A1 | 7/1993 | |
| WO | WO 95/005807 A1 | 3/1995 | |
| WO | WO 00/59482 A1 | 10/2000 | |
| WO | WO 03/077923 A1 | 9/2003 | |
| WO | WO 2004/080438 A1 | 9/2004 | |
| WO | WO 2005/092441 A2 | 10/2005 | |
| WO | WO 2006/128057 A2 | 11/2006 | |
| WO | WO 2009/070794 A1 | 6/2009 | |
| WO | WO 2010/117873 A2 | 10/2010 | |
| WO | WO 2011/053666 A1 | 5/2011 | |
| WO | WO 2011/160136 A2 | 12/2011 | |
| WO | WO 2013/016697 A2 | 1/2013 | |
| WO | WO-2013016697 A2 * | 1/2013 | A61K 31/57 |

OTHER PUBLICATIONS

Emerald Performance Materials; "Benzyl Benzoate;" Product Information Bulletin; (Upon Belief and Knowledge Prior to May 17, 2013); 3 pages; Revision 01; Emerald Kalama Chemical, LLC.

Facchinetti et al.; "Cervical Length Changes During Preterm Cervical Ripening: Effects of 17-Alpha-Hydroxyprogesterone Caproate;" Research; American Journal of Obstetrics and Gynecology; (May 2007); pp. 453c1-453c4; vol. 196(453).

FDA; "17a Alpha Hydroxyprogesterone Caproate for Prevention of Preterm Birth; Overview of FDA Background Document;" (Aug. 2, 2006); 62 pages (see introduction); Food and Drug Administration.

Greene; "Progesterone and Preterm Delivery—Déjá Vu All Over Again;" The New England Journal of Medicine; (Jun. 12, 2003); pp. 2453-2455; vol. 348, No. 24.

Hargrove et al.; "Absorption of Oral Progesterone is Influenced by Vehicles and Particle Size;" American Journal of Obstetrics and Gynecology; (Oct. 1989); pp. 948-951; vol. 161, Issue 4; <doi: 10.1016/0002-9378(89)90759-X>; [abstract].

Johnson et al.; "Efficacy of 17 Alpha-Hydroxyprogesterone Caproate in the Prevention of Premature Labor;" The New England Journal of Medicine; (Oct. 2, 1975); pp. 675-680; vol. 293, No. 14.

Levy et al.; "Pharmacokinetics of Natural Progesterone Administered in the Form of a Vaginal Tablet;" Human Reproduction; (Mar. 1999); pp. 606-610; vol. 14, No. 3; European Society of Human Reproduction and Embryology.

Meis et al.; "Prevention of Recurrent Preterm Delivery by 17 Alpha-Hydroxyprogesterone Caproate;" The New England Journal of Medicine; (Jun. 12, 2003); pp. 2379-2385; vol. 348, No. 24.

Merck Manual; "Oral Contraceptive (OC);" The Merck Manual of Diagnosis and Therapy; (1992); pp. 1773-1778; Ch. 169. Family Planning: Contraception; 16th Ed. Third Printing.

Migally; "Effect of Castor Oil and Benzyl Benzoate Used as a Vehicle for Antiandrogens on the Adrenal Cortex;" Archives of Andrology; (1979); pp. 365-369; vol. 2, No. 4.

Nadai; "Foundation of Drug Pharmacokinetics and Application to Dosage Regimen;" Journal of The Japanese Society for Pediatric Nephrology; (2006); pp. 111-123; vol. 19, No. 2; <doi: https://doi.org/10.3165/jjpn.19.111 >. [Japanese with English Abstract].

Nihon Sankafujinka Gakkaihen; Teiyouryou Keikou Hininyaku no Shiyuou in Kan Sura Gaidorain; (2005); 69 pages.

O'Brien et al.; "Progesterone Vaginal Gel for the Reduction of Recurrent Preterm Birth: Primary Results From a Randomized, Double-Blind, Placebo-Controlled Trial;" Ultrasound in Obstetrics and Gynecology; (Oct. 2007); pp. 687-696; vol. 30, No. 5.

Rai et al.; "Oral Micronized Progesterone for Prevention of Preterm Birth;" International Journal of Gynecology and Obstetrics; (Jan. 2009); pp. 40-43; vol. 104, No. 1.

Ratner et al.; "Menopause and Hormone-Replacement Therapy; Part 2: Hormone-Replacement Therapy Regimens;" West Journal of Medicine; (Jul. 2001); pp. 32-34; vol. 175, No. 1.

Rogers et al.; "Micronized Powders of a Poorly Water Soluble Drug Produced by a Spray-Freezing Into Liquid-Emulsion Process;" European Journal of Pharmaceutics and Biopharmaceutics; (Mar. 2003); pp. 161-172; vol. 55.

Sexton et al.; "Functional Effects of 17-Alpha-Hydroxyprogesterone Caproate (17P) on Human Myometrial Contractility in Vitro;" Reproductive Biology and Endocrinology; (Dec. 7, 2004); 6 pages; vol. 2, No. 80.

Tita et al.; "Progesterone for Preterm Birth Prevention: An Evolving Intervention;" Reviews; American Journal of Obstetrics and Gynecology; (Mar. 2009); pp. 219-224.

Vidaeff et al.; "Critical Appraisal of the Efficacy, Safety, and Patient Acceptability of Hydroxyprogesterone Caproate Injection to Reduce the Risk of Preterm Birth;" Patent Preference and Adherence; (Jul. 11, 2013); pp. 683-691.

Wikipedia; "17-Hydroxyprogesterone;" Wikipedia, The Free Encyclopedia; [online]; [retrieved Apr. 22, 2011]; 5 pages; Retrieved from <URL: http://en.wikipedia.org/wiki/17-Hydroxyprogesterone >; Wikimedia Foundation, Inc.

* cited by examiner

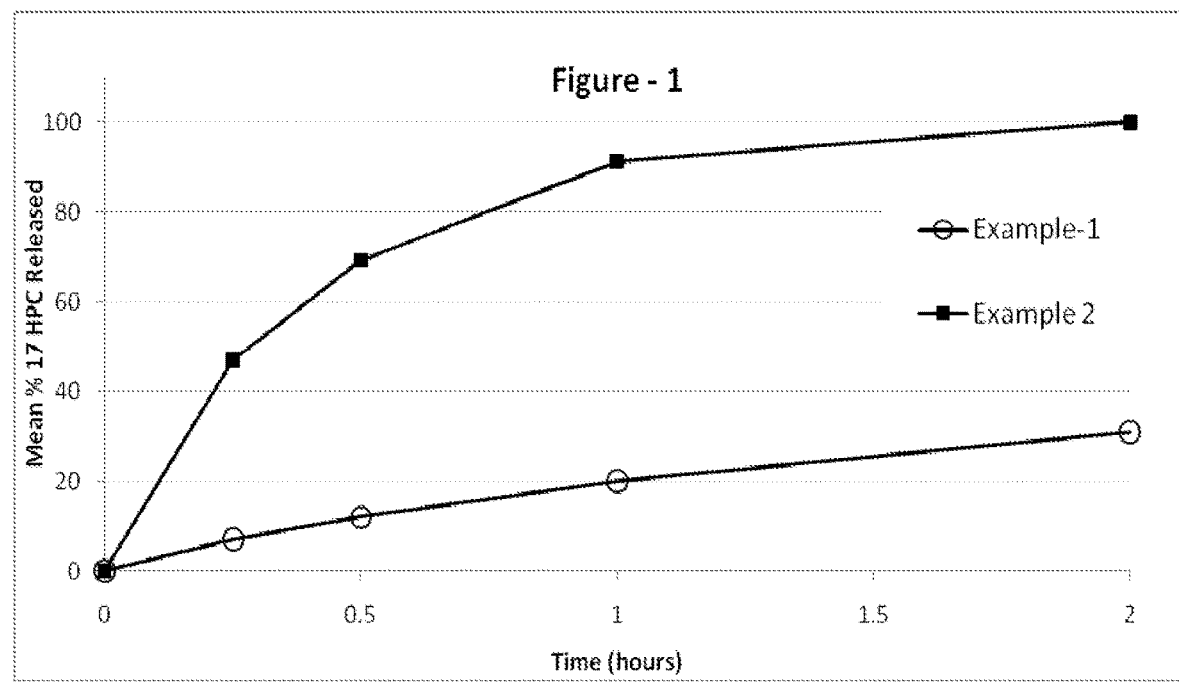
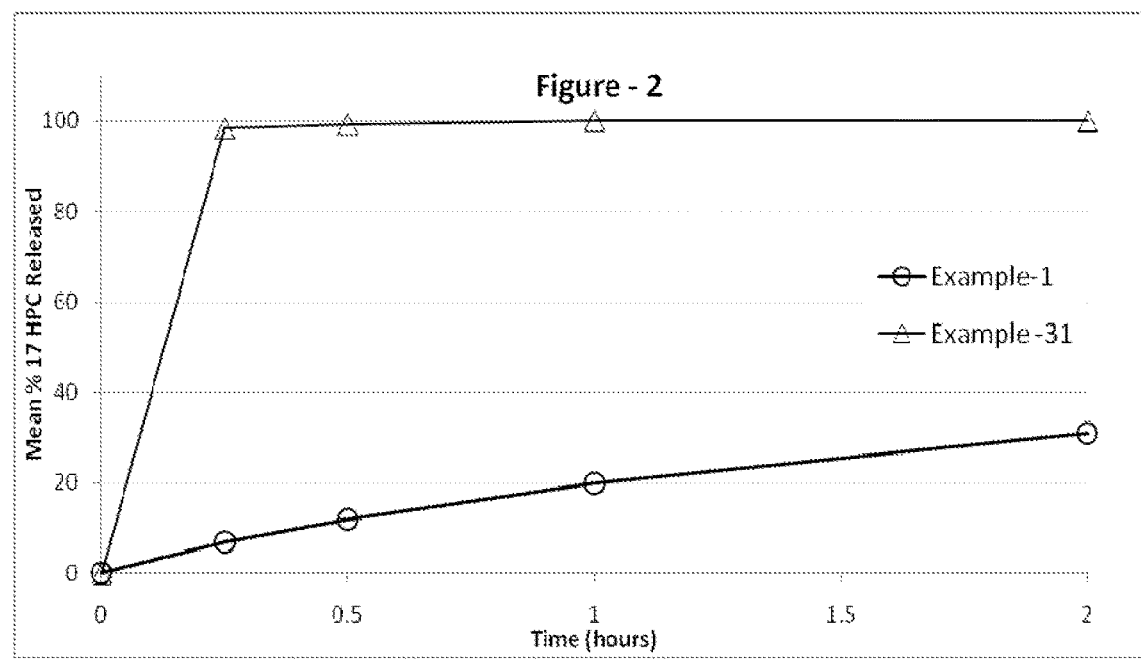

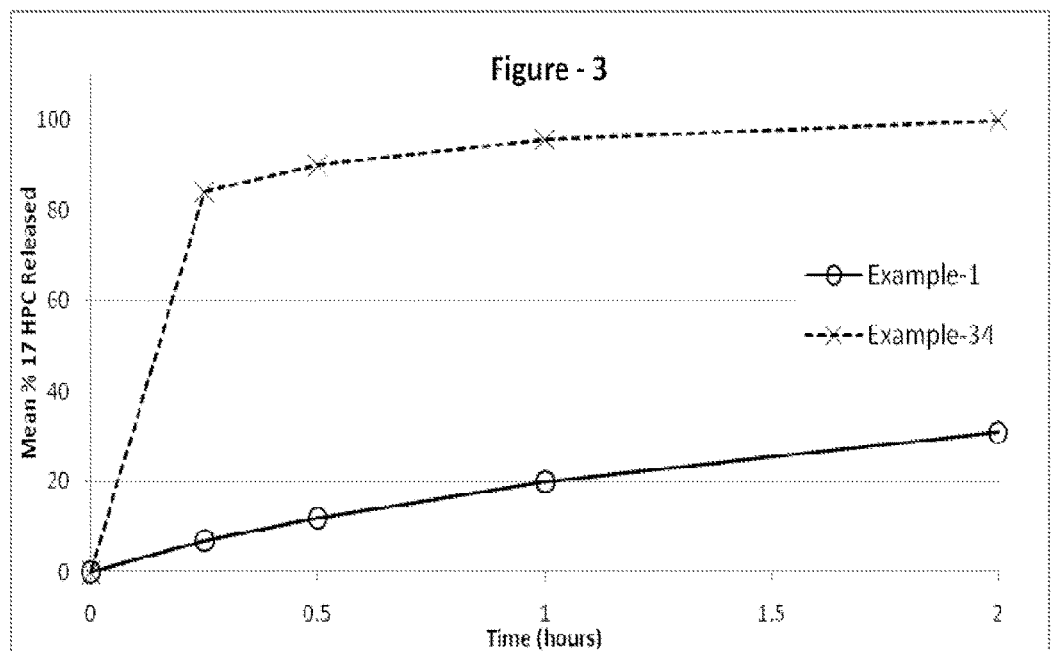
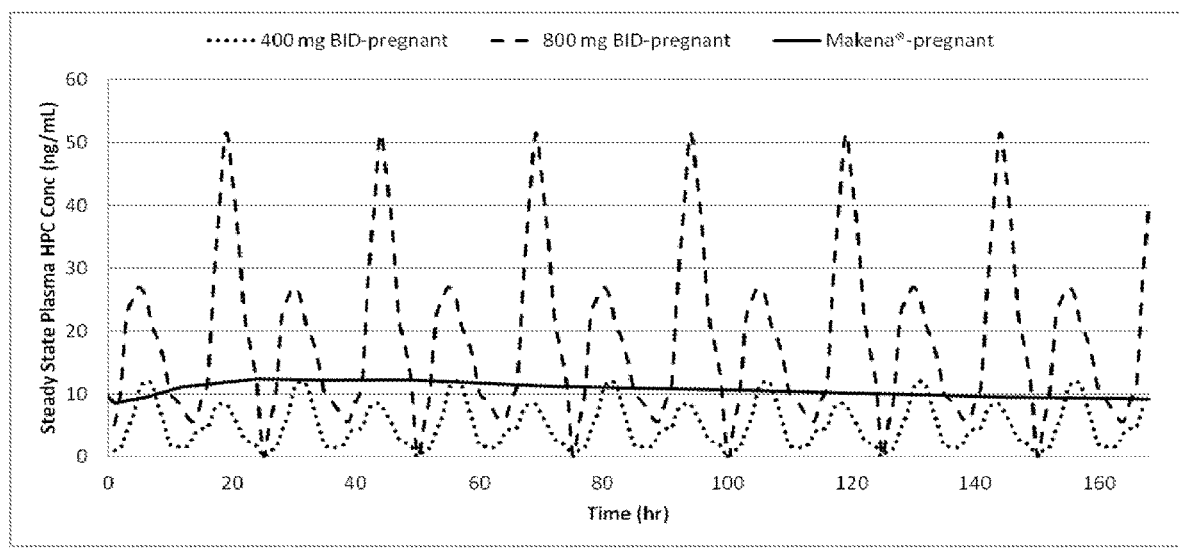
Figure - 4

17-HYDROXYPROGESTERONE ESTER-CONTAINING ORAL COMPOSITIONS AND RELATED METHODS

CROSS-REFERENCE TO RELATED APPLICATION

This application is a continuation of U.S. patent application Ser. No. 16/055,594 filed Aug. 6, 2018, which is a continuation of U.S. patent application Ser. No. 15/190,109, filed Jun. 22, 2016, which claims the benefit of U.S. Provisional Application No. 62/183,031 filed Jun. 22, 2015 and U.S. Provisional Application No. 62/295,951 filed Feb. 16, 2016, each of which is incorporated by reference in their entireties.

FIELD OF THE INVENTION

The present invention relates to 17-hydroxyprogesterone ester containing compositions, oral dosage forms thereof, and associated methods. Accordingly, this invention involves the fields of chemistry, pharmaceutical sciences, medicine and other health sciences.

BACKGROUND OF THE INVENTION 17-alpha hydroxyprogesterone (alternatively hereinafter referred to as 17-hydroxyprogesterone or "17HP") is a C-21 endogenous steroid hormone produced during the syntheses of glucocorticoids and sex steroids. Like progesterone, 17HP is a natural progestagen. It has been isolated from both adrenal glands and corpora lutea. Esters of 17HP are reported to have progestogenic effects and hence, can be used for indications related to pregnancy support as well as non-pregnancy support in both pre- and post-menopausal women. It is reported that 17HP, without esterification, has no progestational activity. However, the synthetic esters of 17HP such 17-hydroxyprogesterone acetate or 17-alpha-hydroxyprogesterone caproate (also referred hereafter as 17 hydroxyprogesterone caproate or 17 HPC) have been shown to exhibit marked progestational activity when administered intramuscularly in animal experiments. 17-Hydroxyprogesterone caproate is a commonly used progestin available for intramuscular injection to prevent Preterm Birth (alternatively hereinafter referred to as "PTB"). This synthetic caproate ester is reportedly inactive when given by mouth but works as a long-acting progestin when administered intramuscularly. The metabolism of 17HP and the metabolism of 17-hydroxyprogesterone caproate in the human female are not yet fully established. Data from humans and animals indicate that intramuscularly administered 17-hydroxyprogesterone caproate has more potent progestational effect on endometrium and is longer lasting than progesterone (alternatively hereinafter referred to as "P"). This may be due to more avid binding of 17-hydroxyprogesterone caproate to the progesterone receptors (alternatively referred to hereinafter as "PR") and placental glucocorticoid receptors (alternatively referred to hereinafter as "GR") that could prevent an increase of placental corticotropin releasing hormone which is associated with onset of labor. 17-hydroxyprogesterone caproate is reportedly effective in providing luteal support in patients undergoing IVF-Embryo Transfer Cycles.

PTB is medically defined as delivery from 20 to 36 weeks of gestation. According to the 2009 Center for Disease Control Report, PTB occurs in about 12.3% of births in the US alone translating to about half a million PTBs annually. Spontaneous PTB accounts for approximately 70-80% of PTB. Of all the pregnancies in the US, one out of every eight live-born infants is born preterm representing an increase of >18% since 1990. Late pre-term birth between 35-36 weeks of gestation contributes to more than half of all PTBs. PTB is the primary cause of neonatal morbidity and mortality. Mortality risk is three fold higher at 35-36 weeks and morbidities such as respiratory distress requiring oxygen, temperature instability, hypoglycemia, jaundice, attention deficit disorders, cerebral palsy, developmental delay, etc. are quite common. PTB related time and costs in intensive care are a major health, social and economic issue with an average cost of PTB delivery amounting to up to 10× that of normal delivery.

Major risk factors implicated in PTB are as follows: History of previous spontaneous PTB (past obstetrics history), cervical length (<2.5 cm at mid pregnancy), presence of fetal fibronectin in vaginal secretions; multiple gestation, low maternal Body Mass Index (BMI), maternal race; maternal age (<17 and >35 years), and smoking. The prior history of at least one PTB is a good indicator of future occurrence potential with 17-50% recurrence potential and 28-70% recurrence potential with two previous PTBs. Benefits of prolonging pregnancy to full term with therapeutic intervention include improved child survival as a function of gestational age, and reduced neonatal hospital stay.

Intramuscular injection of 17-hydroxyprogesterone caproate is available for reducing the risk of PTB in women with singleton pregnancy and history of single spontaneous PTB. The injection marketed as Makena® (250 mg 17-hydroxyprogesterone caproate in 1 mL) mandates regular visits to the doctor's office, as the typical treatment cycle consists of 16-20 weeks of injection repeated every week. This therapy regimen could result increasing the patient's distress and/or anxiety in addition to increasing the repeated travel risks for the patient and fetus. The injection therapy's interferences with the personal and family activities and disruption in professional life are also a major disadvantage.

In addition, adverse events associated with injection of 17-hydroxyprogesterone caproate (e.g. Makena®) at once weekly intervals (every 7 days) the injection site reactions (~45%) such as urticaria, pruritis, swelling, nodule formation and pain at the site of injection have been reported as significant.

Esters of hydroxy progesterone such as acetate, caproate, undecanoate are more lipophilic than hydroxy progesterone. The active substance (17-hydroxyprogesterone caproate) in Makena® is known to be extremely insoluble in water (<20 ng/mL), and very lipophilic with ClogP of about 5.7. Moreover, 17-hydroxyprogesterone caproate has the potential to be metabolized in the presence of fetal and adult hepatocytes and is a substrate for cytochrome inactivation such as CYP3A4 which is overly expressed in pregnant women (~40% upregulation). Due to its extremely low water solubility and a potential to be susceptible for first pass hepatic inactivation oral delivery of long chain esters of 17HP has remained a challenge. It is reported that there is no oral activity with 17 hydroxyprogesterone caproate, an ester of 17 HP, (Saxton D J et. al. *Reproductive Biology and Endocrinology* 2004, 2:80; Greene M F, *NJEM* 348:2453-2455). This could be likely due to very poor or no oral bioavailability of 17 HPC. Although much desired, to date the development of an orally active composition of long chain ester of hydroxyl progesterone remains a significant unmet need. In addition, development of dosage forms that enable administration of lesser number of dosage units per dose and/or at reduced frequency per day is most often desirable.

SUMMARY OF THE INVENTION

It has now been surprisingly found that esters of 17HP can be effectively delivered orally to mammals. The pharmaceutical oral compositions and dosage forms of the present inventions can provide effective bioavailability of an ester of 17HP. Further, the compositions and/or dosage forms disclosed herein provide effective release enhancement for 17 HP esters. We have also surprisingly found that an ester of 17HP can be formulated into oral compositions and oral dosage forms thereof with higher percent w/w loading of the ester. For example, we have found that when one or more solubilizing agents such as for example, benzyl alcohol, benzyl benzoate etc., is incorporated in the composition, a significant amount (i.e. greater than 12% w/w) of the ester of 17HP can be solubilized in the composition or dosage form. The increased drug loading in the compositions and dosage forms of the current inventions, can provide avid advantages including but not limited to reduced size or volume of the unit dosage (i.e., tablet, capsule, syrup, elixir, beverage, etc.), reduced number of dosage units to be taken per single administration, improved patient compliance etc., because patients typically can take fewer number of dosage units per day in order to get a sufficient dose to provide the desired efficacy. In a separate aspect, it was also surprisingly found that an effective bioavailability of the ester of 17HP can be provided by the compositions of the current inventions which when dispersed in an aqueous medium, provide clear or colloidal to hazy or unclear dispersions having partially or fully solubilized drug in the dispersions.

It was also found that the compositions of current invention facilitate production of solid dosage forms such as tablets, caplets, granules, beads, particulates etc., which can solve the drawbacks of having the 17HP ester in a liquid solution form in the dosage unit. This eliminates a number of undesirable inconveniences, such as specialized manufacturing process and/or equipment, poor chemical and/or physical stability of the ester typical to liquid solutions due to the nature of the ester or solvents used, and so-on.

All the oral dosage forms of the present inventions having the drug in the form of solution, suspension, particulates, etc., can be produced by conventional methods of processing and manufacture known in the art.

The present invention provides for compositions and oral dosage forms containing esters of 17HP as well as related methods. The compositions and oral dosage forms can be formulated to include a therapeutically effective amount of an ester of 17HP and a pharmaceutically acceptable carrier. In one embodiment, a pharmaceutically acceptable oral dosage form for pregnancy support and non-pregnancy support is provided. The pharmaceutically acceptable oral dosage can include a therapeutically effective amount of an ester of 17HP and a pharmaceutically acceptable carrier. The oral dosage form can, when measured using a USP Type-II dissolution apparatus in 900 mL of deionized water with 0.5% (w/v) of sodium lauryl sulfate at 50 RPM at 37° C., release at least 20 wt % of the dose of the ester of 17HP after 60 minutes.

In yet a further embodiment, a pharmaceutically acceptable oral dosage form for pregnancy or non-pregnancy support is provided. The pharmaceutically acceptable oral dosage can include a therapeutically effective amount of an ester of 17HP and a pharmaceutically acceptable carrier. The oral dosage form can, when measured using a USP Type-II dissolution apparatus in 900 mL of deionized water with 0.5% (w/v) of sodium lauryl sulfate at 50 RPM at 37° C., release at least 20 wt % more 17HP ester after 60 minutes than an equivalently dosed oral dosage form without the carrier.

In some aspects, the oral dosage forms of the present invention can be used to treat pregnant female subjects who are at risk of preterm birth. Such methods of treatment may include the step of orally administering to the female subject the oral pharmaceutical composition. In some aspects, the dosage amount is an amount sufficient to provide an intended therapeutic effect. In another embodiment, the oral dosage forms can be administered to subjects in need thereof. The administration of the oral dosage form can treat at least one condition selected from preterm labor, preterm birth, infertility and miscarriage. The conditions and the relative treatment can be based on their primary and secondary outcome measurements associated with the administration of the ester of 17HP.

BRIEF DESCRIPTION OF THE DRAWINGS

FIG. 1 is a plot of the in vitro release profile of a 17-hydroxyprogesterone caproate containing oral dosage form in accordance with an embodiment of the present invention compared to a carrier-free dose of 17-hydroxyprogesterone caproate.

FIG. 2 is a plot of the in vitro release profiles of 17-hydroxyprogesterone containing oral dosage forms in accordance with an embodiment of the present invention.

FIG. 3 is a plot of the in vitro release profiles of 17-hydroxyprogesterone containing oral dosage forms in accordance with an embodiment of the present invention.

FIG. 4 is a plot of pharmacokinetics in accordance with embodiments described herein and Example 55.

Figure 5:
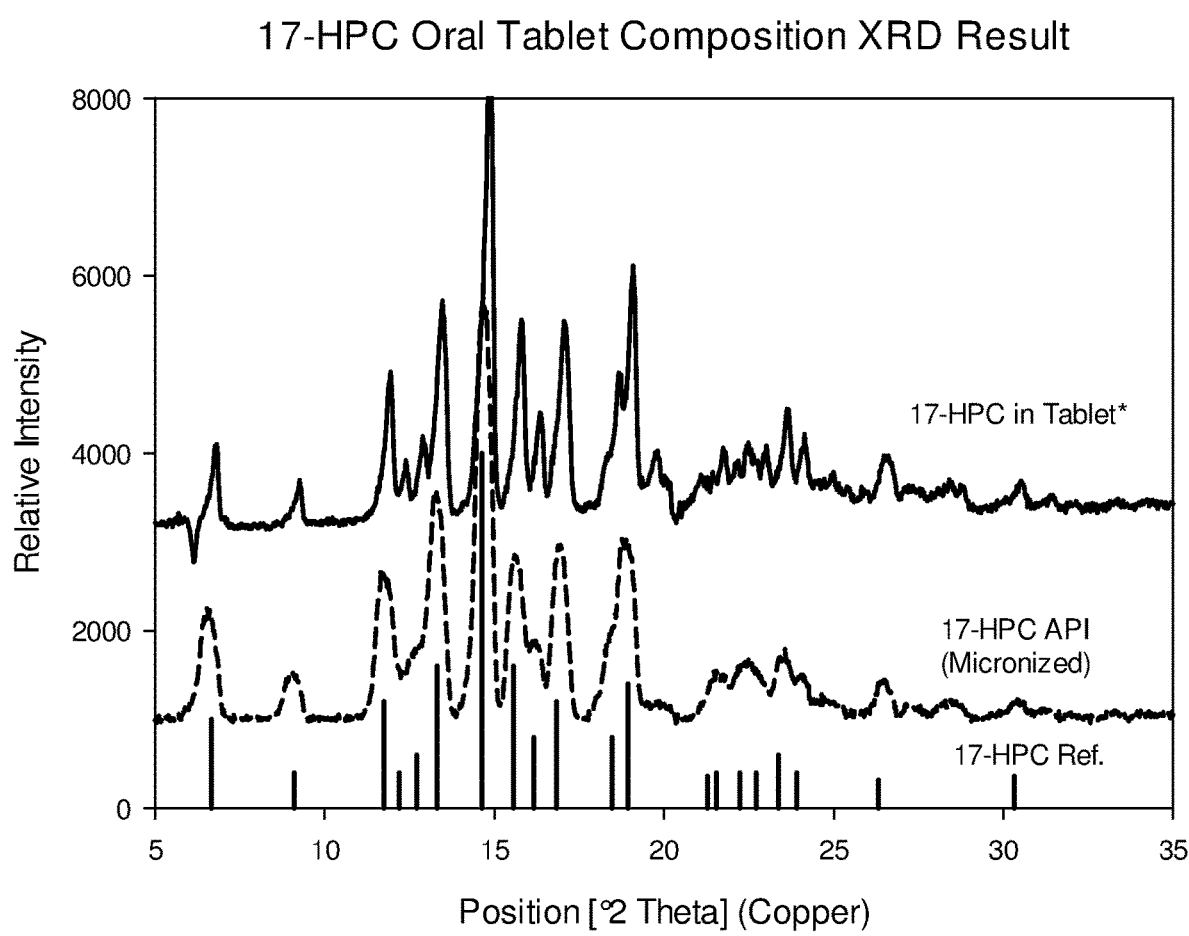
FIG. 5 is a plot of XRD data in accordance with embodiments described here in and Example 56.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Before the present oral dosage forms and methods for the delivery and use of 17-hydroxyprogesterone esters are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It should be noted that, as used in the written description, the singular forms "a," "an," and, "the" include express support for plural referents unless the context clearly dictates otherwise. Thus, for example, reference to "an excipient" includes reference to one or more of such excipients, and reference to "the carrier" includes reference to one or more of such carriers.

Definitions

As used herein, "drug," "active agent," "bioactive agent," "pharmaceutically active agent," "therapeutically active agent" and "pharmaceutical," may be used interchangeably to refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical and medicinal arts. Further, when these terms are used, or when a particular active agent is specifically identified by name or category, it is understood that such recitation is intended to include the active agent per se, as well as pharmaceutically acceptable salts, esters or compounds significantly related thereto, including without limitation, prodrugs, active metabolites, isomers, and the like.

As used herein, the term "recurrent" is used to refer to a repeat or re-occurrence of at least one incidence like "miscarriage", "preterm birth" or "preterm labor" or "multifetal gestation" or any like medical situation in reference with or without same partner, with or without previous live birth.

As used herein, the term "treatment" when used in conjunction with the administration of a 17-hydroxyprogesterone ester, refers to the administration of the 17-hydroxyprogesterone ester to subjects who are either asymptomatic or symptomatic. In other words, "treatment" can refer to the act of reducing or eliminating a condition (i.e. symptoms manifested), or it can refer to prophylactic treatment, (i.e. administering to a subject not manifesting symptoms in order to prevent their occurrence). Such prophylactic treatment can also be referred to as prevention of the condition, preventative action, preventative measures, etc.

As used herein, the term "ester" represents compounds produced by reaction between acids and alcohols with the elimination of water. As described herein, the term "ester" can also represent the class of organic compounds corresponding to the inorganic salts formed from an organic acid and an alcohol. In one aspect, the "ester of 17-hydroxyprogesterone" can be the caproate ester, but can also represent esters of the longer chain fatty acids such as undecanoic acid and higher, that typically get lymphatically absorbed and avoid first pass hepatic metabolism for improved efficacy or safety.

As used herein, the terms "formulation" and "composition" are used interchangeably and refer to a mixture of two or more compounds, elements, or molecules. In some aspects, the terms "formulation" and "composition" may be used to refer to a mixture of one or more active agents with a carrier or other excipients. Furthermore, the term "dosage form" can include one or more formulation(s) or composition(s) provided in a format for administration to a subject. When any of the above terms is modified by the term "oral" such terms refer to compositions, formulations, or dosage forms formulated and intended for oral administration to subjects.

The terms "pharmaceutically acceptable carrier" or "carrier" are used interchangeably and refer to a pharmaceutically acceptable substance that enables a pharmaceutical composition and/or a dosage form of an ester of 17-hydroxyprogesterone. Further, in some aspects, the carrier is an element or ingredient that can be varied for the alteration of release rate and/or extent of the active agent, for example an ester of 17-hydroxyprogesterone, from the composition and/or the dosage form. In one aspect of the invention, a pharmaceutically acceptable carrier is a compound, or a mixture of compounds, that determines, controls, or contributes, at least in part, to the release of an ester of 17-hydroxyprogesterone from a pharmaceutical oral composition and/or dosage form, when tested using a USP Type II apparatus in about 900 mL of simulated intestinal fluid (according to USP, SIF, without enzyme) having 0.5% w/w sodium lauryl sulfate at about 37° C. and 50 rpm.

In another embodiment, the composition or dosage form provides a release of the ester of 17-hydroxyprogesterone such that when tested using a USP Type II apparatus in about 900 mL of simulated intestinal fluid having 0.5% w/w sodium lauryl sulfate at about 37° C. and 50 rpm, at least 20% more the ester of 17-hydroxyprogesterone is released after the first 60 minutes compared to an equivalent dose an ester of 17-hydroxyprogesterone oral dosage form without the pharmaceutically acceptable carrier. In another particular embodiment, the composition or the dosage form releases at least 40% more of the ester of 17-hydroxyprogesterone after the first 60 minutes compared to an equivalent dose an ester of 17-hydroxyprogesterone oral dosage form without the pharmaceutically acceptable carrier.

It should be noted that the release of the ester of 17-hydroxyprogesterone from the composition or the dosage form can be tested in a suitable solubilizing medium or a non-solubilizing aqueous medium at about 37° C., in a USP Type II apparatus at 50 rpm. For example, aqueous medium can be water, simulated gastric fluid (SGF) with or without enzyme, simulated intestinal fluid (SIF) with or without enzyme, a hydro-alcoholic solution, a surfactant solution and the like. The aqueous medium can be used for the purpose of determining the release rate and/or extent of the ester of 17-hydroxyprogesterone from the compositions or the dosage forms. The aqueous medium can be a non-solubilizing aqueous medium (for example, having low or no surfactant in the medium) for the entire amount of the ester present in the composition or the dosage form. In one embodiment, the non-solubilizing aqueous medium can solubilize about 90% or less of the amount of ester present in the composition or dosage form. In another embodiment, the non-solubilizing aqueous medium can solubilize about 80% or less, about 70% or less, about 60% or less, about 50% or less, about 30% or less, or about 20% or less of the total amount of the ester present in the composition or dosage form.

Conversely, in another embodiment the aqueous medium is capable of solubilizing substantially all of the ester of 17-hydroxyprogesterone present in the composition or dosage form. In one embodiment, the aqueous medium can solubilize at least about 90% of the amount of the ester of 17-hydroxyprogesterone present in the composition or dosage form. In a particular embodiment the aqueous medium can solubilize about 1.5 times or more, about 3 times or more, 5 times or more of the amount of the ester 17-hydroxyprogesterone present in the composition or dosage form.

As used herein, "subject" refers to a mammal that may benefit from the administration of a drug composition or method of this invention. Examples of subjects include humans, and may also include other animals such as horses, pigs, cattle, dogs, cats, rabbits, and aquatic mammals. In one specific aspect, a subject is a human. In another aspect, the subject is a female. In yet another aspect, the oral dosage form of the current invention is for a female requiring pregnancy support.

The term "oral administration" represents any method of administration in which an active agent can be administered by swallowing, chewing, or sucking or drinking an oral dosage form. Such solid or liquid oral dosage forms are traditionally intended to substantially release and or deliver the active agent in the gastrointestinal tract beyond the mouth and/or buccal cavity. Examples of solid dosage forms include conventional tablets, multi-layer tablets capsules, caplets, etc., which do not substantially release the drug in the mouth or in the oral cavity.

As used herein, the terms "release" and "release rate" are used interchangeably to refer to the discharge or liberation of a substance, including without limitation a drug, from the dosage form into a surrounding environment such as an aqueous medium either in vitro or in vivo.

As used herein, the term "lipophilic" when used in combination with both solid and liquid lipophilic additives (alternatively referred to hereinafter as "LA"), refers to additives that "love oil" and generally have poor or no solubility in water. "Lipophilic surfactants" (alternatively referred to hereinafter as "LS") refer to lipophilic additives that have HLB values of 10 or less, preferably between 2 to 10. Conversely, the term "hydrophilic," when used in combination with both solid and liquid hydrophilic additives (alternatively referred to hereinafter as "HA"), refers to additives that "love water", and generally have average or good solubility in water. "Hydrophilic surfactants" (alternatively referred to hereinafter as "HS") are hydrophilic additives that have significant surface active property and that have HLB values of more than 10.

As used herein, the term "lipid" or lipid substance" when used in connection, with various compounds, refers to fatty acid (unless otherwise specified, having chain length greater than $C_6$) or fatty acid esters or glycerides of fatty acid esters, mixtures thereof and derivatives thereof, although not including salts thereof.

In some aspects of the present invention, the release of the drug may be controlled release. As used herein, the term "controlled release" represents the release of the drug from the dosage form according to a predetermined profile. In some aspects, the controlled release selected can be, intermediate, delayed, extended, sustained, pulsatile, gastric, enteric or colonic. In another aspect, combinations of the aforementioned release profiles may be used in order to achieve specific delivery results, such as an immediate release followed by a delayed and/or a sustained release of the active agent.

As used herein, a composition or dosage form provides "immediate release" when greater than about 90% of the drug is released after the first 30 minutes, in a USP simulated gastric fluid (SGF) with or without enzyme.

As used herein, the term "pregnancy support" when used to describe the functionality of the oral compositions or dosage forms of the present invention, can refer to providing exogenous progestational support from inception through birth including, but not limited to preterm birth, preterm labor, and miscarriage. The pregnancy support can provide improved quality of the pregnancy for the pregnant woman, the fetus, or both. Further, pregnancy support can also include increased fertility for a woman trying to become pregnant.

As used herein, the term "non-pregnancy" support when used to describe the functionality of the oral compositions or dosage forms of the present invention, can refer to conditions that require exogenous supplementation of a progestogen agent to a non-pregnant subject, such as a non-pregnant woman, including but not limited to, delaying or preventing the occurrence of pregnancy, preventing or treating conditions due to progesterone deficiencies such as amenorrhea, fibroids, contraception, postpartum lactation suppression, treatment of dysfunctional uterine bleeding, endometriosis, endometrial hyperplasia, cervical hyperplasia, hormone replacement therapy, treatment of hypoventilation, prevention and treatment of osteoporosis, management of breast, hypothyroidism, migraine headaches, pemporomandibular joint syndrome, catamenial epilepsy, endometrial, and/or renal carcinomas. In one embodiment, the term "non-pregnancy" support when used to describe the functionality of the oral compositions or dosage forms of the present invention can refer to conditions that require exogenous supplementation of the progestogen agent of the invention to a male human for example, to effect contraception, to counter estogenic activity, etc. It should be noted that the present compositions and dosage forms of the ester of the 17-hydroxyprogesterone may be administered alone or in combination with other therapy. In another embodiment, the current invention compositions and dosage forms of the ester of the 17-hydroxyprogesterone may be used to supplement, augment, mitigate, treat, cure or prevent, or for providing prophylaxis in a subject in need thereof.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

As used herein, the term "about" is used to provide flexibility to a numerical range endpoint by providing that a given value may be "a little above" or "a little below" the endpoint. As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

EXEMPLARY EMBODIMENTS

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

During pregnancy, it has been shown that serum progestogen, including progesterone and 17-hydroxyprogesterone levels are decreased in the pregnant female in cases of intrauterine death, premature labor, threatened premature labor, premature rupture of membranes, amnionitis and abruption of placenta. As discussed above, it has been discovered that esters of 17-hydroxyprogesterone have potential for use in pregnancy to treat and or prevent the following conditions or occurrences: spontaneous abortion in women who have had previous spontaneous abortion, history of recurrent spontaneous abortion, previous stillbirth, previous premature delivery (<37 weeks), previous premature (<37 weeks) rupture of membranes or PROM, previous pregnancy related hypertension or toxemia, previous abruption of placenta, threatened premature labor or cerclage, multiple pregnancy, primary or secondary infertility, congenital uterine anomaly or any other condition where endogenous progestogen (e.g. progesterone) levels are lower than in normal pregnancy.

Primary and secondary outcome measures can be used to determine the need for and/or the effectiveness of ester of 17-hydroxyprogesterone supplementation therapy for pregnancy related support to a particular subject and its direct or indirect effect on the neonates. Typical primary and secondary outcome measures for preterm birth and preterm labor include, without limitation, Primary Outcome Measures (Maternal):
1. Perinatal mortality
2. Preterm birth (less than 32 weeks' gestation)
3. Preterm birth (less than 34 weeks' gestation)
4. Preterm birth (less than 37 weeks' gestation)
5. Major neuro-developmental handicap at childhood follow up Secondary Outcome Measures (Maternal):
1. Threatened preterm labor
2. Pre-labor spontaneous rupture of membranes
3. Adverse drug reaction
4. Pregnancy prolongation (interval between randomization and birth)
5. Mode of birth
6. Number of antenatal hospital admissions
7. Satisfaction with the therapy
8. Use of tocolysis Secondary Outcome Measures (Infant):
1. Birth before 37 completed weeks
2. Birth before 34 completed weeks
3. Birth before 32 completed weeks
4. Birth before 28 completed weeks
5. Birth weight less than the third centile for gestational age
6. Birth weight less than 2500 grams
7. Apgar score of less than seven at five minutes
8. Respiratory distress syndrome
9. Use of mechanical ventilation
10. Duration of mechanical ventilation
11. Intraventricular hemorrhage—grades III or IV
12. Periventricular leucomalacia
13. Retinopathy of prematurity
14. Retinopathy of prematurity—grades III or IV
15. Chronic lung disease
16. Necrotizing enterocolitis
17. Neonatal sepsis
18. Fetal death
19. Neonatal death
20. Admission to neonatal intensive care unit
21. Neonatal length of hospital stay
22. Teratogenic effects (including virilisation in female infants)

Secondary Outcome Measures (Child):
1. Major sensorineural disability (defined as any of legal blindness, sensorineural deafness requiring hearing aids, moderate or severe cerebral palsy, or developmental delay or intellectual impairment)
2. Developmental delay
3. Intellectual impairment
4. Motor impairment
5. Visual impairment
6. Blindness
7. Deafness
8. Hearing impairment
9. Cerebral palsy
10. Child behavior
11. Child temperament
12. Learning difficulties
13. Growth assessments at childhood follow up (weight, head circumference, length, skin fold thickness)

In-vitro Fertilization
1. Primary Outcome Measures:
   1.1. Pregnancy Rate
   1.2. Live birth
   1.3. Ongoing pregnancy rate
   1.4. Clinical pregnancy, defined as ultrasound evidence of fetal heart activity at 6-8 weeks of gestation
   1.5. Fetus Vitality measured by heart beat
   1.6. Rate of complete abortion 24-48 hrs after receiving medical treatment for early pregnancy failure.
2. Secondary Outcome Measures:
   2.1. Clinical pregnancy
   2.2. Cycle Cancellation Rates
   2.3. Number of Oocytes Generated
   2.4. Number of Embryos Generated
   2.5. Serum hormonal evaluation
   2.6. Follicular fluid evaluation
   2.7. Peak estradiol level
   2.8. Ampules of gonadotropins required during ovarian stimulation
   2.9. Number of days of ovarian stimulation
   2.10. Number of oocytes retrieved
   2.11. Number of embryos transferred
   2.12. Number of embryos frozen
   2.13. Embryo grade
   2.14. Implantation rate
   2.15. Miscarriage rate
   2.16. Pregnancy outcome
   2.17. rate of complete abortion at one week, time to expulsion of products of conception, correlation of abortion rates to serum 17-hydroxyprogesterone levels and type of pregnancy failure, number of bleeding days and patient satisfaction
   2.18. Ovarian Response [assessed upon completion of the controlled ovarian stimulation and the egg collection procedures]

Miscarriage
1. Primary Outcomes
   1.1. Miscarriage
   1.2. Early miscarriage up to 12 weeks
   1.3. Miscarriage later than 12 weeks and less than 23 weeks
   1.4. Cytokine ratio IFN/IL-10
   1.5. Clinical pregnancy rate at 8 weeks and 12 weeks of pregnancy
2. Secondary Outcomes
   2.1. Mother
      a. Pain relief (threatened miscarriage)
      b. Severity of 'morning sickness'—intensified headache
      c. nausea, breast tenderness
      d. reported thromboembolic events
      e. Thrombolytic events
      f. depression;
      g. admission to special care unit
      h. subsequent fertility.
      i. PIBF level
      j. Uterine contraction frequency
   2.2. Child
      a. Preterm birth;
      b. stillbirth;
      c. neonatal death;
      d. low birthweight less than 2500 g
      e. fetal genital abnormalities;
      f. teratogenic effects (impairing normal fetal development);
      g. admission to special care unit.
   2.3. General
      a. Intrauterine fetal death
      b. Still birth
      c. Fetal
      d. Exploratory analysis of pregnancy outcome by monitoring biochemical and clinical pregnancy parameters, weekly evaluation of serum progesterone
      e. live birth rate, cycle cancellation rate, rate of spontaneous abortion, rate of biochemical pregnancy, rate of ectopic pregnancy Several biomarkers have been implicated in predicting preterm birth (PTB). Among symptomatic women, the likelihood ratio (LR+) for the prediction of PTB is known to be greater than 10 using amniotic fluid (AF) interleukin-6 (IL-6), AF *Ureaplasma urealyticum*, as well as a multimarker consisting of cervical IL-6, cervical IL-8, and cervical length (CL). The LR+ is also known to be between 5 and 10 for serum C-reactive protein (CRP). An LR+ between 2.5 and 5 was recorded for serum corticotropin-releasing hormone (CRH), cervical IL-6, serum relaxin.

In asymptomatic women, AFU urealyticum and a multimarker consisting of five individual markers [fFN, CL, serum alpha-fetoprotein (AFP), serum alkaline phosphatase, and serum granulocyte colony-stimulating factor (G-CSF)] predict PTB with an LR+ greater than 10. The LR+ was between 5 and 10 for serum relaxin and CL. LRs+ recorded for serum alkaline phosphatase, salivary estriol, serum CRH, serum G-CSF, cervical IL-6, AF IL-6, cervical fFN, AFP, and chlamydia all ranged between 2.5 and 5. Finally, an LR+ below 2.5 has been documented for serum ferritin, serum CRP, BV, and cervical ferritin.

Miscarriages and possible miscarriages can be categorized in several ways: A) threatened or possible miscarriage—when any bleeding from the uterus occurs before 20 weeks, but the cervix is closed and the fetus is alive; B) Inevitable abortion or miscarriage (inevitable—meaning it cannot be stopped, particularly if there is bleeding from the uterus and the cervix is opening prior to 20 weeks, but neither the fetus nor placenta have passed out of the woman's body)—the membranes around the fetus may or may not have ruptured (broken); C) Incomplete abortion or miscarriage—when a portion of the fetus or placenta has passed out of the uterus prior to 20 weeks gestation while some of the placenta or fetus remains in the uterus; D) Complete miscarriage—complete expulsion of all the membranes around the fetus and the placenta and the cervix closes prior to 20 weeks; E) Missed abortion or miscarriage—death of the fetus prior to 20 weeks gestation with neither the fetus nor the placenta having been expelled from the uterus; F) Recurrent miscarriage—a woman is said to have recurrent miscarriage after she has already had two or more miscarriages in a row; G) Blighted ovum or anembryonic gestation—occurs when a gestational sac forms inside the uterus, but no fetus is present after seven weeks.

Threatened miscarriage, as demonstrated by low endogenous progesterone or 17-hydroxyprogesterone, or vaginal bleeding with or without abdominal cramps within 26 weeks of conception, is a common complication of pregnancy. It occurs in about 20% of recognized pregnancies. Risk of miscarriage is increased in older women and those with a history of miscarriage.

It has been shown that low serum levels of progestogen (progesterone or 17 HP) or human chorionic gonadotropin (hCG) are a risk factor for miscarriage. Threatened miscarriage causes considerable stress and anxiety for a pregnant woman. Because esters of 17-hydroxyprogesterone interact with the progesterone receptor, it is believed that treatment with esters of 17-hydroxyprogesterone can be designed based on progesterone levels. One diagnostic criterion is low serum progesterone, but levels vary widely during early pregnancy and any later decline may be attributed to a dysfunctioning placenta. Nevertheless, luteal support is widely used for the management of threatened miscarriage. First trimester pregnancies show risk of miscarriage with declining serum progesterone levels. Levels of <5 ng/ml were associated with a spontaneous miscarriage in 86% of cases compared with only 8% at levels of 20-25 ng/ml. A threshold value of 14 ng/ml has been reported to differentiate between the viable and non-continuing pregnancies. Other maternal serum biomarkers such as Tumor marker CA-125, Inhibin A, Anandamide and progesterone induced blocking factor (PIBF) are also good indicators of miscarriage risk.

In one embodiment, the compositions of the present invention are intended to provide an increase in the baseline endogenous progesterone and/or 17-hydroxyprogesterone. In a particular embodiment, the increase in the baseline endogenous progesterone can be greater than 10%. Progestogens also have a direct pharmacological effect by reducing the synthesis of prostaglandins, thereby relaxing uterine smooth musculature and preventing inappropriate contractions that may result in miscarriage.

Although the oral dosage forms and methods of the present invention can be used in most female subjects, patients most suitable for receiving oral 17-hydroxyprogesterone ester of this invention are the ones that have one or more of the following conditions, symptoms, and/or needs: 1) are in need of an anti-inflammatory; 2) are progesterone deficient with base line progesterone in early (first trimester) pregnancy of $C_{avg}$<14 ng/ml or baseline progesterone levels, $C_{avg}$ of less than 50 ng/ml in late (second and third trimester) pregnancy; 3) have genetic variation of the SERPINH1 gene that cause to produce a reduced amount of the protein, collagen, which may lead to weakened fetal membranes; 4)

have a genetic variant of the Prolylcarboxypeptidase gene associated with preeclampsia; 5) have certain bacterial infections (bacterial vaginosis) including *Ureaplasma urealyticum, Mycoplasma hominis, Gardnerella vaginalis*, and *Peptostreptococcus* and *Bacteroides* species; 6) have abnormal amniotic fluid metabolome (the sum of all metabolic processes occurring in the amniotic fluid) indicating risk for prematurity; 7) have had above average total phthalate exposure; 8) abnormal prepregnancy body mass index; 9) have inflammatory milieu of the vagina in early pregnancy; 10) have increased maternal plasma urocortin levels; 11) show increased uterine activity as noted by Home Uterine Activity Monitoring; 12) test positive to salivary estriol levels predicting preterm delivery; 13) show alarming fetal Fibronectin Screening (fFS) results; 14) show unusual cervical shortening relative to gestational age as measured by cervical ultrasonography, or transvaginal ultrasound or digital examination with/without use of Cervilenz™; 15) show unusual maternal serum bio markers such as Tumour marker CA-125, or Inhibin A, or Anandamide or Progesterone Induced Blocking factor (PIBF); 16) have unbalanced ratio of Th-1 cytokines to Th-2 cytokines such as IFN to IL-10.

Besides maintaining pregnancy, other potential uses of the ester of 17-hydroxyprogesterone containing oral dosage forms of the present invention include, but are not limited to: a) preventing estrogen dominance; b) stimulating new bone formation and prevent/reverse osteoporosis; c) providing the precursor for adrenal cortex hormones (corticosteroids); d) treating variety of skin problems such as acne in adult women, seborrhea, rosacea, psoriasis, and keratosis; e) promoting myelin sheath production to protect nerve fibers and speed nerve signals; f) managing depression that accompany PMS, menopause, postpartum depression, etc.; g) protecting from brain/spinal cord injury, stroke, and/or hemorrhage.

In one embodiment, the present invention provides for oral dosage forms containing esters of 17-hydroxyprogesterone as well as related methods. The oral dosage forms can be formulated for pregnancy support and can include a therapeutically effective amount of an ester of 17-hydroxyprogesterone and a pharmaceutically acceptable carrier. The oral dosage form can, when measured using a USP Type-II dissolution apparatus in 900 mL of deionized water with 0.5 (w/v) of sodium lauryl sulfate at 50 RPM at 37° C., release at least 20 wt % of the dose of the ester of 17-hydroxyprogesterone after 60 minutes. In yet a further embodiment, the oral dosage form can, when measured using a USP Type-II dissolution apparatus in 900 mL of deionized water with 0.5 (w/v) of sodium lauryl sulfate at 50 RPM at 37° C., release at least 20 wt % more 17-hydroxyprogesterone ester after 60 minutes than an equivalently dosed oral dosage form without the carrier.

A number of 17-hydroxyprogesterone esters can be used in the compositions and oral dosages of the present invention. Examples of specific acceptable esters of 17-hydroxyprogesterone include without limitation, acetate esters of 17-hydroxyprogesterone, caproate esters of 17-hydroxyprogesterone, undecanoate esters of 17-hydroxyprogesterone, and the like and combinations thereof. Other pharmacologically active and acceptable esters of 17-hydroxyprogesterone may also be prepared and used in accordance with the embodiments of the present invention so long as they provide the desired support in pregnancy and/or non-pregnancy conditions.

The ester of 17-hydroxyprogesterone can be present in the compositions and oral dosage forms of the present disclosure in a variety of forms. In one embodiment, the ester of 17-hydroxyprogesterone can be present in particulate form. The particulate form can have a mean diameter of about 50 µm or less. The particulate form can have a mean diameter of about 25 µm or less. In another embodiment, the particulate form can have a mean diameter of about 1 µm or less. In another embodiment, the ester of 17-hydroxyprogesterone can be present in a fully solubilized form. In another embodiment, the ester of 17-hydroxyprogesterone can be present in a partially solubilized form. In another embodiment, a portion of the ester of 17-hydroxyprogesterone present in the composition and/or dosage form can be present in particulate or unsolubilzied form. In some embodiments, the ester of 17-hydroxyprogesterone can be present in both solubilized form as well as in particulate form.

In some embodiments, the carrier of the compositions or oral dosage forms of the present invention can act to facilitate the delivery, release, and/or bioavailability of the ester of 17-hydroxyprogesterone. In certain aspects, the carrier can be one or a mixture of two or more compounds. The carrier can include at least one of a lipophilic and/or a hydrophilic component additive. The lipophilic and hydrophilic additives that can be used in the compositions of the invention can be selected from a variety of classes of the pharmaceutical aids including, but not limited to, absorbents, acids, adjuvants, anticaking agent, antitacking agents, antifoamers, anticoagulants, antimicrobials, antioxidants, antiphlogistics, astringents, antiseptics, bases, binders, bufferants, chelating agents, sequestrants, celluloses, coagulants, coating agents, colorants, dyes, pigments, complexing agents, crystal growth regulators, denaturants, desiccants, drying agents, dehydrating agents, diluents, disintegrants, dispersants, emollients, emulsifiers, encapsulants, enzymes, extenders, fillers, flavor masking agents, flavorants, fragrances, gelling agents, glidants hardeners, stiffening agents, humectants, lubricants, moisturizers, pH control agents, plasticizers, soothing agents, demulcents, retarding agents, spreading agents, stabilizers, suspending agents, sweeteners, thickening agents, consistency regulators, surfactants, opacifiers, polymers, preservatives, antigellants, rheology control agents, softeners, solubilizers; solvents tonicifiers, viscosity modulators UV absorbers, or combinations thereof. In some embodiments additives from multiple classes or types can be used.

Non-limiting examples of compounds that can form all or a part of the carrier are set forth in the following lists which have been organized in general categories. It is to be understood that the categories are not intended to limit the particular carrier compounds, but are simply present for ease of organization and presentation. With this in mind, example carrier compounds can include one or more of the following:

Triglycerides such as Aceituno oil; Almond oil; Arachis oil; Babassu oil; Blackcurrant seed oil; Borage oil; Canola oil (Lipex 108 (Abitec)); Castor oil; Cocoa butter; Coconut oil (Pureco 76 (Abitec)); Coffee seed oil); Corn oil; Cottonseed oil; Crambe oil; Cuphea species oil; Evening primrose oil; Grapeseed oil; Groundnut oil; Hemp seed oil; Illipe butter; Kapok seed oil; Linseed oil; Menhaden oil; Mowrah butter; Mustard seed oil; Oiticica oil; Olive oil; Palm oil; Palm kernel oil; Peanut oil; Poppy seed oil; Rapeseed oil; Rice bran oil; Safflower oil; Sal fat; Sesame oil; Shark liver oil; Shea nut oil; Soybean oil; Stillingia oil; Sunflower oil; Tall oil; Tea sead oil; Tobacco seed oil; Tung oil (China wood oil): Vernonia oil; Wheat germ oil; Hydrogenated castor oil (Castorwax); Hydrogenated coconut oil (Pureco 100 (Abitec)); Hydrogenated cottonseed oil (Dritex C (Abitec)); Hydrogenated palm oil (Dritex PST (Abitec); Softisan154 (Huls)); Hydrogenated soybean oil (Sterotex HM NF (Abitec); Dritex S (Abitec)); Hydrogenated vegetable oil (Sterotex NF (Abitec): Hydrokote M (Abitec)); Hydrogenated cottonseed and castor oil (Sterotex K (Abitec)); Partially hydrogenated soybean oil (Hydrokote AP5 (Abitec)); Partially soy and cottonseed oil (Apex B (Abitec)); Glyceryl tributyrate (Sigma); Glyceryl tricaproate (Sigma); Glyceryl tricaprylate (Sigma); Glyceryl tricaprate (Captex 1000 (Abitec)); Glyceryl trundecanoate (Captex 8227 (Abitec)); Glyceryl trilaurate (Sigma); Glyceryl trimyristate (Dynasan 114 (Huls)); Glyceryl tripalmitate (Dynasan 116 (Huls)); Glyceryl tristearate (Dynasan 118 (Huls)); Glyceryl triarcidate (Sigma); Glyceryl trimyristoleate (Sigma); Glyceryl tripalmitoleate (Sigma); Glyceryl trioleate (Sigma); Glyceryl trilinoleate (Sigma); Glyceryl tricaprylate/caprate (Captex 300 (Abitec); Captex 355 (Abitec); Miglyol 810 (Huls); Miglyol 812 (Huls)); Glyceryl tricaprylate/caprate/laurate (Captex 350 (Abitec)); Glyceryl tricaprylate/caprate/linoleate (Captex 810 (Abitec); Miglyol 818 (Huls)); Glyceryl tricaprylate/caprate/stearate (Softisan 378 (Huls); (Larodan); Glyceryl tricaprylate/laurate/stearate (Larodan); Glyceryl 1,2-caprylate-3-linoleate (Larodan); Glyceryl 1,2-caprate-3-stearate (Larodan); Glyceryl 1,2-laurate-3-myristate (Larodan); Glyceryl 1,2-myristate-3-laurate (Larodan); Glyceryl 1,3-palmitate-2-butyrate (Larodan); Glyceryl 1,3-stearate-2-caprate (Larodan); Glyceryl 1,2-linoleate-3-caprylate (Larodan), mixtures and derivatives thereof. Fractionated triglycerides, modified triglycerides, synthetic triglycerides, and mixtures of triglycerides are also within the scope of the invention.

PEG-Fatty Acid Monoester Surfactants (listed as compound name (common commercial product name (supplier) (HLB)): PEG 4-100 monolaurate (Crodet L series (Croda) (>9)); PEG 4-100 monooleate (Crodet 0 series (Croda) (>8)); PEG 4-100 monostearate (Crodet S series (Croda), Myrj Series (Atlas/ICI) (>6)); PEG 400 distearate (Cithrol 4DS series (Croda) (>10)); PEG 100, 200, 300 monolaurate (Cithrol ML series (Croda) (>10)); PEG 100, 200, 300 monooleate (Cithrol MO series (Croda) (>10)); PEG 400 dioleate (Cithrol 4DO series (Croda) (>10)); PEG 400-1000 monostearate (Cithrol MS series (Croda) (>10)); PEG-1 stearate (Nikkol MYS-1EX (Nikko), Coster K1 (Condea) (2)); PEG-2 stearate (Nikkol MYS-2 (Nikko) (4)); PEG-2 oleate (Nikkol MYO-2 (Nikko) (4.5)); PEG-4 laurate (Mapeg® 200 ML (PPG), Kessco® PEG 200 ML (Stepan), LIPOPEG 2 L (LIPO Chem.) (9.3)); PEG-4 oleate (Mapeg® 200 MO (PPG), Kessco® PEG 200 MO (Stepan) (8.3)); PEG-4 stearate (Kessco® PEG 200 MS (Stepan), Hodag 20 S (Calgene), Nikkol MYS-4 (Nikko) (6.5)); PEG-5 stearate (Nikkol TMGS-5 (Nikko) (9.5)); PEG-5 oleate (Nikkol TMGO-5 (Nikko) (9.5)); PEG-6 oleate (Algon OL 60 (Auschem SpA), Kessco® PEG 300 MO (Stepan), Nikkol MYO-6 (Nikko), Emulgante A6 (Condea) (8.5)); PEG-7 oleate (Algon OL 70 (Auschem SpA) (10.4)); PEG-6 laurate (Kessco® PEG300 ML (Stepan) (11.4)); PEG-7 laurate (Lauridac 7 (Condea) (13)); PEG-6 stearate (Kessco® PEG300 MS (Stepan) (9.7)); PEG-8 laurate (Mapeg® 400 ML (PPG), LIPOPEG 4DL (Lipo Chem.) (13)); PEG-8 oleate (Mapeg® 400 MO (PPG), Emulgante A8 (Condea) (12)); PEG-8 stearate (Mapeg® 400 MS (PPG), Myrj 45 (12)); PEG-9 oleate (Emulgante A9 (Condea) (>10)); PEG-9 stearate (Cremophor S9 (BASF) (>10)); PEG-10 laurate (Nikkol MYL-10 (Nikko), Lauridac 10 (Croda) (13)); PEG-10 oleate (Nikkol MYO-10 (Nikko) (11)); PEG-12 stearate (Nikkol MYS-10 (Nikko), Coster K100 (Condea) (11)); PEG-12 laurate (Kessco® PEG 600 ML (Stepan) (15)); PEG-12 oleate (Kessco® PEG 600 MO (Stepan) (14)); PEG-12 ricinoleate (CAS #9004-97-1) (>10)); PEG-12 stearate (Mapeg® 600 MS (PPG), Kessco® PEG 600 MS (Stepan) (14)); PEG-15 stearate (Nikkol TMGS-15 (Nikko), Koster K15 (Condea) (14)); PEG-15 oleate (Nikkol TMGO-15 (Nikko) (15)); PEG-20 laurate (Kessco® PEG 1000 ML (Stepan) (17)); PEG-20 oleate (Kessco® PEG 1000 MO (Stepan) (15)); PEG-20 stearate (Mapeg® 1000 MS (PPG), Kessco® PEG 1000 MS (Stepan), Myrj 49 (16)); PEG-25 stearate (Nikkol MYS-25 (Nikko) (15)); PEG-32 laurate (Kessco® PEG 1540 ML (Stepan) (16)); PEG-32 oleate (Kessco® PEG 1540 MO (Stepan) (17)); PEG-32 stearate (Kessco® PEG 1540 MS (Stepan) (17)); PEG-30 stearate (Myrj 51 (>10)); PEG-40 laurate (Crodet L40 (Croda) (17.9)); PEG-40 oleate (Crodet O40 (Croda) (17.4)); PEG-40 stearate (Myrj 52, Emerest 2715 (Henkel), Nikkol MYS-40 (Nikko) (>10)); PEG-45 stearate (Nikkol MYS-45 (Nikko) (18)); PEG-50 stearate (Myrj 53 (>10)); PEG-55 stearate (Nikkol MYS-55 (Nikko) (18)); PEG-100 oleate (Crodet 0-100 (Croda) (18.8)); PEG-100 stearate (Myrj 59, Ariacel 165 (ICI) (19)); PEG-200 oleate (Albunol 200 MO (Taiwan Surf) (>10)); PEG-400 oleate (LACTOMUL (Henkel), Albunol 400 MO (Taiwan Surf) (>10)); PEG-600 oleate (Albunol 600 MO (Taiwan Surf) (>10)); and combinations thereof.

PEG-Fatty Acid Diesters (listed as compound name (common commercial product name (supplier) (HLB)): PEG-4 dilaurate (Mapeg®200 DL (PPG), Kessco® PEG 200 DL (Stepan), LIPOPEG 2-DL (Lipo Chem.) (7)); PEG-4 dioleate (Mapeg® 200 DO (PPG), (6)); PEG-4 distearate (Kessco® 200 DS (Stepan) (5)); PEG-6 dilaurate (Kessco® PEG 300 DL (Stepan) (9.8)); PEG-6 dioleate (Kessco® PEG 300 DO (Stepan) (7.2)); PEG-6 distearate (Kessco® PEG 300 DS (Stepan) (6.5)); PEG-8 dilaurate (Mapeg® 400 DL (PPG), Kessco® PEG 400 DL (Stepan), LIPOPEG 4 DL (Lipo Chem.) (11)); PEG-8 dioleate (Mapeg® 400 DO (PPG), Kessco® PEG 400 DO (Stepan), LIPOPEG 4 DO (Lipo Chem.) (8.8)); PEG-8 distearate (Mapeg® 400 DS (PPG), CDS 400 (Nikkol) (11)); PEG-10 dipalmitate (Polyaldo 2PKFG (>10)); PEG-12 dilaurate (Kessco® PEG 600 DL (Stepan) (11.7)); PEG-12 distearate (Kessco® PEG 600 DS (Stepan) (10.7)); PEG-12 dioleate (Mapeg® 600 DO (PPG), Kessco® 600 DO (Stepan) (10)); PEG-20 dilaurate (Kessco® PEG 1000 DL (Stepan) (15)); PEG-20 dioleate (Kessco® PEG 1000 DO (Stepan) (13)); PEG-20 distearate (Kessco® PEG 1000 DS (Stepan) (12)); PEG-32 dilaurate (Kessco® PEG 1540 DL (Stepan) (16)); PEG-32 dioleate (Kessco® PEG 1540 DO (Stepan) (15)); PEG-32 distearate (Kessco® PEG 1540 DS (Stepan) (15)); PEG-400 dioleate (Cithrol 4DO series (Croda) (>10)); PEG-400 distearate (Cithrol 4DS series (Croda) (>10)); and combinations thereof.

PEG-Fatty Acid Mono- and Di-ester Mixtures (listed as compound name (common commercial product name (supplier) (HLB)): PEG 4-150 mono, dilaurate (Kessco® PEG 200-6000 mono, dilaurate (Stepan))); PEG 4-150 mono, dioleate (Kessco® PEG 200-6000 mono, dioleate (Stepan))); PEG 4-150 mono, distearate (Kessco® 200-6000 mono, distearate (Stepan)), and combinations thereof.

Polyethylene Glycol Glygerol Fatty Acid Esters (listed as compound name (common commercial product name (supplier) (HLB)): PEG-20 glyceryl laurate (Tagat® L (Goldschmidt) (16)); PEG-30 glyceryl laurate (Tagat® L2 (Goldschmidt) (16)); PEG-15 glyceryl laurate (Glycerox L series (Croda) (15)); PEG-40 glyceryl laurate (Glycerox L series (Croda) (15)); PEG-20 glyceryl stearate (Capmul® EMG (ABITEC), (13)); (Aldo® MS-20 KFG (Lonza))); PEG-20 glyceryl oleate (Tagat® O (Goldschmidt) (>10)); PEG-30 glyceryl oleate (Tagat® O2 (Goldschmidt) (>10)); and combinations thereof.

Alcohol-oil Transesterification Products: (listed as compound name (common commercial product name (supplier) (HLB)): PEG-3 castor oil (Nikkol CO-3 (Nikko) (3)); PEG-5, 9, and 16 castor oil (ACCONON CA series (ABITEC) (6-7)); PEG-20 castor oil (Emalex C-20 (Nihon Emulsion), Nikkol CO-20 TX (Nikko) (11)); PEG-23 castor oil (Emulgante EL23 (>10)); PEG-30 castor oil (Emalex C-30 (Nihon Emulsion), Alkamuls® EL 620 (Rhone-Poulenc), Incrocas 30 (Croda) (11)); PEG-35 castor oil (Cremophor EL and EL-P (BASF), Emulphor EL, Incrocas-35 (Croda), Emulgin RO 35 (Henkel))); PEG-38 castor oil (Emulgante EL 65 (Condea))); PEG-40 castor oil (Emalex C-40 (Nihon Emulsion), Alkamuls® EL 719 (Rhone-Poulenc) (13)); PEG-50 castor oil (Emalex C-50 (Nihon Emulsion) (14)); PEG-56 castor oil (Eumulgin® PRT 56 (Pulcra SA) (>10)); PEG-60 castor oil (Nikkol CO-60TX (Nikko) (14)); PEG-100 castor oil (Thornley (>10)); PEG-200 castor oil (Eumulgin® PRT 200 (Pulcra SA) (>10)); PEG-5 hydrogenated castor oil (Nikkol HCO-5 (Nikko) (6)); PEG-7 hydrogenated castor oil (Simusol® 989 (Seppic), Cremophor WO7 (BASF) (6)); PEG-10 hydrogenated castor oil (Nikkol HCO-10 (Nikko) (6.5)); PEG-20 hydrogenated castor oil (Nikkol HCO-20 (Nikko) (11)); PEG-25 hydrogenated castor oil (Simulsol® 1292 (Seppic), Cerex ELS 250 (Auschem SpA) (11)); PEG-30 hydrogenated castor oil (Nikkol HCO-30 (Nikko) (11)); PEG-40 hydrogenated castor oil (Cremophor RH 40 (BASF), Croduret (Croda), Emulgin HRE 40 (Henkel) (13)); PEG-45 hydrogenated castor oil (Cerex ELS 450 (Auschem Spa) (14)); PEG-50 hydrogenated castor oil (Emalex HC-50 (Nihon Emulsion) (14)); PEG-60 hydrogenated castor oil (Nikkol HCO-60 (Nikko); Cremophor RH 60 (BASF) (15)); PEG-80 hydrogenated castor oil (Nikkol HCO-80 (Nikko) (15)); PEG-100 hydrogenated castor oil (Nikkol HCO-100 (Nikko) (17)); PEG-6 corn oil (Labrafil® M 2125 CS (Gattefosse) (4)); PEG-6 almond oil (Labrafil® M 1966 CS (Gattefosse) (4)); PEG-6 apricot kernel oil (Labrafil® M 1944 CS (Gattefosse) (4)); PEG-6 olive oil (Labrafil® M 1980 CS (Gattefosse) (4)); PEG-6 peanut oil (Labrafil® M 1969 CS (Gattefosse) (4)); PEG-6 hydrogenated palm kernel oil (Labrafil® M 2130 BS (Gattefosse) (4)); PEG-6 palm kernel oil (Labrafil® M 2130 CS (Gattefosse) (4)); PEG-6 triolein (Labrafil® M 2735 CS (Gattefosse) (4)); PEG-8 corn oil (Labrafil® WL 2609 BS (Gattefosse) (6-7)); PEG-20 corn glycerides (Crovol M40 (Croda) (10)); PEG-20 almond glycerides (Crovol A40 (Croda) (10)); PEG-25 trioleate (TAGAT® TO (Goldschmidt) (11)); PEG-40 palm kernel oil (Crovol PK-70 (>10)); PEG-60 corn glycerides (Crovol M70 (Croda) (15)); PEG-60 almond glycerides (Crovol A70 (Croda) (15)); PEG-4 caprylic/capric triglyceride (Labrafac® Hydro (Gattefosse), (4-5)); PEG-8 caprylic/capric glycerides (Labrasol (Gattefosse), Labrafac CM 10 (Gattefosse) (>10)); PEG-6 caprylic/capric glycerides (SOFTIGEN® 767 (Huls), Glycerox 767 (Croda) (19)); Lauroyl macrogol-32 glyceride (GELUCIRE 44/14 (Gattefosse) (14)); Stearoyl macrogol glyceride (GELUCIRE 50/13 (Gattefosse) (13)); Mono, di, tri, tetra esters of vegetable oils and sorbitol (SorbitoGlyceride (Gattefosse) (<10)); Pentaerythrityl tetraisostearate (Crodamol PTIS (Croda) (<10)); Pentaerythrityl distearate (Albunol DS (Taiwan Surf.) (<10)); Pentaerythrityl tetraoleate (Liponate P0-4 (Lipo Chem.) (<10)); Pentaerythrityl tetrastearate (Liponate PS-4 (Lipo Chem.) (<10)); Pentaerythrityl tetracaprylate/tetracaprate (Liponate PE-810 (Lipo Chem.), Crodamol PTC (Croda) (<10)); Pentaerythrityl tetraoctanoate (Nikkol Pentarate 408 (Nikko))); and combinations thereof.

Polyglycolized Fatty Acids: (listed as compound name (common commercial product name (supplier) (HLB)): Polyglyceryl-2 stearate (Nikkol DGMS (Nikko) (5-7)); Polyglyceryl-2 oleate (Nikkol DGMO (Nikko) (5-7)); Polyglyceryl-2 isostearate (Nikkol DGMIS (Nikko) (5-7)); Polyglyceryl-3 oleate (Caprol® 3GO (ABITEC), Drewpol 3-1-O (Stepan) (6.5)); Polyglyceryl-4 oleate (Nikkol Tetraglyn 1-O (Nikko) (5-7)); Polyglyceryl-4 stearate (Nikkol Tetraglyn 1-S(Nikko) (5-6)); Polyglyceryl-6 oleate (Drewpol 6-1-O (Stepan), Nikkol Hexaglyn 1-O (Nikko) (9)); Polyglyceryl-10 laurate (Nikkol Decaglyn 1-L (Nikko) (15)); Polyglyceryl-10 oleate (Nikkol Decaglyn 1-O (Nikko) (14)); Polyglyceryl-10 stearate (Nikkol Decaglyn 1-S (Nikko) (12)); Polyglyceryl-6 ricinoleate (Nikkol Hexaglyn PR-15 (Nikko) (>8)); Polyglyceryl-10 linoleate (Nikkol Decaglyn 1-LN (Nikko) (12)); Polyglyceryl-6 pentaoleate (Nikkol Hexaglyn 5-O (Nikko) (<10)); Polyglyceryl-3 dioleate (Cremophor G032 (BASF) (<10)); Polyglyceryl-3 distearate (Cremophor GS32 (BASF) (<10)); Polyglyceryl-4 pentaoleate (Nikkol Tetraglyn 5-O (Nikko) (<10)); Polyglyceryl-6 dioleate (Caprol® 6G20 (ABITEC); Hodag PGO-62 (Calgene), PLUROL OLEIQUE CC 497 (Gattefosse) (8.5)); Polyglyceryl-2 dioleate (Nikkol DGDO (Nikko) (7)); Polyglyceryl-10 trioleate (Nikkol Decaglyn 3-O (Nikko) (7)); Polyglyceryl-10 pentaoleate (Nikkol Decaglyn 5-O (Nikko) (3.5)); Polyglyceryl-10 septaoleate (Nikkol Decaglyn 7-O (Nikko) (3)); Polyglyceryl-10 tetraoleate (Caprol® 10G40 (ABITEC); Hodag PGO-62 (CALGENE), Drewpol 10-4-O (Stepan) (6.2)); Polyglyceryl-10 decaisostearate (Nikkol Decaglyn 10-IS (Nikko) (<10)); Polyglyceryl-101 decaoleate (Drewpol 10-10-O (Stepan), Caprol 10G100 (ABITEC), Nikkol Decaglyn 10-O (3.5)); Polyglyceryl-10 mono, dioleate (Caprol® PGE 860 (ABITEC) (11)); Polyglyceryl polyricinoleate (Polymuls (Henkel) (3-20)); and combinations thereof.

Propylene Glycol Fatty Acid Esters: (listed as compound name (common commercial product name (supplier) (HLB)): Propylene glycol monocaprylate (Capryol 90 (Gattefosse), Nikkol Sefsol 218 (Nikko) (<10)); Propylene glycol monolaurate (Lauroglycol 90 (Gattefosse), Lauroglycol FCC (Gattefosse) (<10)); Propylene glycol oleate (Lutrol OP2000 (BASF) (<10)); Propylene glycol myristate (Mirpyl (<10)); Propylene glycol monostearate (ADM PGME-03 (ADM), LIPO PGMS (Lipo Chem.), Aldo® PGHMS (Lonza) (3-4)); Propylene glycol hydroxy stearate (<10)); Propylene glycol ricinoleate (PROPYMULS (Henkel) (<10)); Propylene glycol isostearate (<10)); Propylene glycol monooleate (Myverol P-O6 (Eastman) (<10)); Propylene glycol dicaprylate/dicaprate (Captex® 200 (ABITEC), Miglyol® 840 (Huls), Neobee® M-20 (Stepan) (>6)); Propylene glycol dioctanoate (Captex® 800 (ABITEC) (>6)); Propylene glycol caprylate/caprate (LABRAFAC PG (Gattefosse) (>6)); Propylene glycol dilaurate (>6)); Propylene glycol distearate (Kessco® PGDS (Stepan) (>6)); Propylene glycol dicaprylate (Nikkol Sefsol 228 (Nikko) (>6)); Propylene glycol dicaprate (Nikkol PDD (Nikko) (>6)); and combinations thereof.

Mixtures of Propylene Glycol Esters and Glycerol-Esters: (listed as compound name (common commercial product name (supplier) (HLB)): Oleic (ATMOS 300, ARLACEL 186 (ICI) (3-4)); Stearic (ATMOS 150 (3-4)); and combinations thereof.

Mono- and Diglycerides: (listed as compound name (common commercial product name (supplier) (HLB)): Monopalmitolein (C16:1) (Larodan) (<10)); Monoelaidin (C18:1) (Larodan) (<10)); Monocaproin (C6) (Larodan) (<10)); Monocaprylin (Larodan) (<10)); Monocaprin (Larodan) (<10)); Monolaurin (Larodan) (<10)); Glyceryl monomyristate (C14) (Nikkol MGM (Nikko) (3-4)); Glyceryl monooleate (C18:1) (PECEOL (Gattefosse), Hodag GMO-D, Nikkol MGO (Nikko) (3-4)); Glyceryl monooleate (RYLO series (Danisco), DIMODAN series (Danisco), EMULDAN (Danisco), ALDO® MO FG (Lonza), Kessco GMO (Stepan), MONOMULS® series (Henkel), TEGIN 0, DREWMULSE GMO (Stepan), Atlas G-695 (ICI), GMOrphic 80 (Eastman), ADM DMG-40, 70, and 100 (ADM), Myverol (Eastman) (3-4)); Glycerol monooleate/linoleate (OLICINE (Gattefosse) (3-4)); Glycerol monolinoleate (Maisine (Gattefosse), MYVEROL 18-92, Myverol 18-06 (Eastman) (3-4)); Glyceryl ricinoleate (Softigen® 701 (Huls), HODAG GMR-D (Calgene), ALDO® MR (Lonza) (6)); Glyceryl monolaurate (ALDO® MLD (Lonza), Hodag GML (Calgene) (6.8)); Glycerol monopalmitate (Emalex GMS-P (Nihon) (4)); Glycerol monostearate (Capmul® GMS (ABITEC), Myvaplex (Eastman), IMWITOR® 191 (Huls), CUTINA GMS, Aldo® MS (Lonza), Nikkol MGS series (Nikko) (5-9)); Glyceryl mono-,dioleate (Capmul® GMO-K (ABITEC) (<10)); Glyceryl palmitic/stearic (CUTINA MD-A, ESTAGEL-G18 (<10)); Glyceryl acetate (Lamegin® EE (Grunau GmbH) (<10)); Glyceryl laurate (Imwitor® 312 (Huls), Monomuls® 90-45 (Grunau GmbH), Aldo® MLD (Lonza) (4)); Glyceryl citrate/lactate/oleate/linoleate (Imwitor® 375 (Huls) (<10)); Glyceryl caprylate (Imwitor® 308 (Huls), Capmul® MCMC8 (ABITEC) (5-6)); Glyceryl caprylate/caprate (Capmul® MCM (ABITEC) (5-6)); Caprylic acid mono,diglycerides (Imwitor® 988 (Huls) (5-6)); Caprylic/capric glycerides (Imwitor® 742 (Huls) (<10)); Mono- and diacetylated monoglycerides (Myvacet® 9-45, Myvacet® 9-40, Myvacet® 9-08 (Eastman), Lamegin® (Grunau) (3.8-4)); Glyceryl monostearate (Aldo® MS, Arlacel 129 (ICI), LIPO GMS (Lipo Chem.), Imwitor® 191 (Huls), Myvaplex (Eastman) (4.4)); Lactic acid esters of mono,diglycerides (LAMEGIN GLP (Henkel) (<10)); Dicaproin (C6) (Larodan) (<10); Dicaprin (C10) (Larodan) (<10); Dioctanoin (C8) (Larodan) (<10); Dimyristin (C14) (Larodan) (<10); Dipalmitin (C16) (Larodan) (<10); Distearin (Larodan) (<10); Glyceryl dilaurate (C12) (Capmul® GDL (ABITEC) (3-4)); Glyceryl dioleate (Capmul® GDO (ABITEC) (3-4)); Glycerol esters of fatty acids (GELUCIRE 39/01 (Gattefosse), GELUCIRE 43/01 (Gattefosse) GELUCIRE 37/06 (Gattefosse) (1 6)); Dipalmitolein (C16:1) (Larodan) (<10]; 1,2 and 1,3-diolein (C18:1) (Larodan) (<10]; Dielaidin (C18:1) (Larodan) (<10); Dilinolein (C18:2) (Larodan) (<10); and combinations thereof.

Sterol and Sterol Derivatives: (listed as compound name (common commercial product name (supplier) (HLB)): Cholesterol, sitosterol, lanosterol (<10)); PEG-24 cholesterol ether (Solulan C-24 (Amerchol) (>10)); PEG-30 cholestanol (Nikkol DHC (Nikko) (>10)); Phytosterol (GENEROL series (Henkel) (<10)); PEG-25 phyto sterol (Nikkol BPSH-25 (Nikko) (>10)); PEG-5 soya sterol (Nikkol BPS-5 (Nikko) (<10)); PEG-10 soya sterol (Nikkol BPS-10 (Nikko) (<10)); PEG-20 soya sterol (Nikkol BPS-20 (Nikko) (<10)); PEG-30 soya sterol (Nikkol BPS-30 (Nikko) (>10)); and combinations thereof.

Polyethylene Glycol Sorbitan Fatty Acid Esters: (listed as compound name (common commercial product name (supplier) (HLB)): PEG-10 sorbitan laurate (Liposorb L-10 (Lipo Chem.) (>10)); PEG-20 sorbitan monolaurate (Tween-20 (Atlas/ICI), Crillet 1 (Croda), DACOL MLS 20 (Condea) (17)); PEG-4 sorbitan monolaurate (Tween-21 (Atlas/ICI), Crillet 11 (Croda) (13)); PEG-80 sorbitan monolaurate (Hodag PSML-80 (Calgene); T-Maz 28 (>10)); PEG-6 sorbitan monolaurate (Nikkol GL-1 (Nikko) (16)); PEG-20 sorbitan monopalmitate (Tween-40 (Atlas/ICI), Crillet 2 (Croda) (16)); PEG-20 sorbitan monostearate (Tween-60 (Atlas/ICI), Crillet 3 (Croda) (15)); PEG-4 sorbitan monostearate (Tween-61 (Atlas/ICI), Crillet 31 (Croda) (9.6)); PEG-8 sorbitan monostearate (DACOL MSS (Condea) (>10)); PEG-6 sorbitan monostearate (Nikkol TS106 (Nikko) (11)); PEG-20 sorbitan tristearate (Tween-65 (Atlas/ICI), Crillet 35 (Croda) (11)); PEG-6 sorbitan tetrastearate (Nikkol GS-6 (Nikko) (3)); PEG-60 sorbitan tetrastearate (Nikkol GS-460 (Nikko) (13)); PEG-5 sorbitan monooleate (Tween-81 (Atlas/ICI), Crillet 41 (Croda) (10)); PEG-6 sorbitan monooleate (Nikkol TO-106 (Nikko) (10)); PEG-20 sorbitan monooleate (Tween-80 (Atlas/ICI), Crillet 4 (Croda) (15)); PEG-40 sorbitan oleate (Emalex ET 8040 (Nihon Emulsion) (18)); PBG-20 sorbitan trioleate (Tween-85 (Atlas/ICI), Crillet 45 (Croda) (11)); PEG-6 sorbitan tetraoleate (Nikkol GO-4 (Nikko) (8.5)); PEG-30 sorbitan tetraoleate (Nikkol GO-430 (Nikko) (12)); PEG-40 sorbitan tetraoleate (Nikkol GO-440 (Nikko) (13)); PEG-20 sorbitan monoisostearate (Tween-120 (Atlas/ICI), Crillet 6 (Croda) (>10)); PEG sorbitol hexaoleate (Atlas G-1086 (ICI) (10)); PEG-6 sorbitol hexastearate (Nikkol GS-6 (Nikko) (3)); and combinations thereof.

Polyethylene Glycol Alkyl Ethers: (listed as compound name (common commercial product name (supplier) (HLB)): PEG-2 oleyl ether,oleth-2 (Brij 92/93 (Atlas/ICI) (4.9)); PEG-3 oleyl ether,oleth-3 (Volpo 3 (Croda) (<10)); PEG-5 oleyl ether,oleth-5 (Volpo 5 (Croda) (<10)); PEG-10 oleyl ether,oleth-10 (Volpo 10 (Croda), Brij 96/97 (Atlas/ICI) (12)); PEG-20 oleyl ether,oleth-20 (Volpo 20 (Croda), Brij 98/99 (Atlas/ICI) (15)); PEG-4 lauryl ether, laureth-4 (Brij 30 (Atlas/ICI) (9.7)); PEG-9 lauryl ether (>10)); PEG-23 lauryl ether, laureth-23 (Brij 35 (Atlas/ICI) (17)); PEG-2 cetyl ether (Brij 52 (ICI) (5.3)); PEG-10 cetyl ether (Brij 56 (ICI) (13)); PEG-20 cetyl ether (BriJ 58 (ICI) (16)); PEG-2 stearyl ether (Brij 72 (ICI) (4.9)); PEG-10 stearyl ether (Brij 76 (ICI) (12)); PEG-20 stearyl ether (Brij 78 (ICI) (15)); PEG-100 stearyl ether (Brij 700 (ICI) (>10)); and combinations thereof.

Sugar Esters: (listed as compound name (common commercial product name (supplier) (HLB)): Sucrose distearate (SUCRO ESTER 7 (Gattefosse), Crodesta F-10 (Croda) (3)); Sucrose distearate/monostearate (SUCRO ESTER 11 (Gattefosse), Crodesta F-110 (Croda) (12)); Sucrose dipalmitate (7.4)); Sucrose monostearate (Crodesta F-160 (Croda) (15)); Sucrose monopalmitate (SUCRO ESTER 15 (Gattefosse) (>10)); Sucrose monolaurate (Saccharose monolaurate 1695 (Mitsubisbi-Kasei) (15)); and combinations thereof.

Polyethylene Glycol Alkyl Phenols: (listed as compound name (common commercial product name (supplier) (HLB)): PEG-10-100 nonyl phenol (Triton X series (Rohm & Haas), Igepal CA series (GAF, USA), Antarox CA series (>10)); (GAF, UK); PEG-15-100 octyl phenol ether (Triton N-series (Rohm & Haas), Igepal CO series (GAF, USA), Antarox CO series (GAF, UK) (>10)); and combinations thereof.

Polyethylene-Polyoxypropylene Block Copolymers (AKA—"poloxamer"): These polymers have the formula: $HO(C_2H_4O)_a(C_3H_6O)_b(C_2H_4O)_aH$ where "a" and "b" denote the number of polyoxyethylene and polyoxypropylene units, respectively. The compounds are listed by generic name, with the corresponding "a" and "b" values. POE-POP Block Copolymers)); (a, b values in)); (HO(C<2>H<4>O)<a>)); (COMPOUND (C<3>H<6>O)<b>(C<2>H<4>O)<a>H (HLB)); (Poloxamer 105 (a=11 (b=16 (8)); (Poloxamer 108 (a=46 (b=16 (>10)); (Poloxamer 122 (a=5 (b=21 (3)); (Poloxamer 123 (a=7 (b=21 (7)); (Poloxamer 124 (a=11 (b=21 (>7)); (Poloxamer 181 (a=3 (b=30)); (Poloxamer 182 (a=8 (b=30 (2)); (Poloxamer 183 (a=10 (b=30)); (Poloxamer 184 (a=13 (b=30)); (Poloxamer 185 (a=19 (b=30)); (Poloxamer 188 (a=75 (b=30 (29)); (Poloxamer 212 (a=8 (b=35)); (Poloxamer 215 (a=24 (b=35)); (Poloxamer 217 (a=52 (b=35)); (Poloxamer 231 (a=16 (b=39)); (Poloxamer 234 (a=22 (b=39)); (Poloxamer 235 (a=27 (b=39)); (Poloxamer 237 (a=62 (b=39 (24)); (Poloxamer 238 (a=97 (b=39)); (Poloxamer 282 (a=10 (b=47)); (Poloxamer 284 (a=21 (b=47)); (Poloxamer 288 (a=122 (b=47 (>10)); (Poloxamer 331 (a=7 (b=54 (0.5)); (Poloxamer 333 (a=20 (b=54)); (Poloxamer 334 (a=31 (b=54)); (Poloxamer 335 (a=38 (b=54)); (Poloxamer 338 (a=128 (b=54)); (Poloxamer 401 (a=6 (b=67)); (Poloxamer 402 (a=13 (b=67)); (Poloxamer 403 (a=21 (b=67)); (Poloxamer 407 (a=98 (b=67)); and combinations thereof.

Sorbitan Fatty Acid Esters: (listed as compound name (common commercial product name (supplier) (HLB)): Sorbitan monolaurate (Span-20 (Atlas/ICI), Crill 1 (Croda), Arlacel 20 (ICI) (8.6)); Sorbitan monopalmitate (Span-40 (Atlas/ICI), Crill 2 (Croda), Nikkol SP-10 (Nikko) (6.7)); Sorbitan monooleate (Span-80 (Atlas/ICI), Crill 4 (Croda), Crill 50 (Croda) (4.3)); Sorbitan monostearate (Span-60 (Atlas/ICI), Crill 3 (Croda), Nikkol SS-10 (Nikko) (4.7)); Sorbitan trioleate (Span-85 (Atlas/ICI), Crill 45 (Croda), Nikkol SO-30 (Nikko) (4.3)); Sorbitan sesquioleate (Arlacel-C (ICI), Crill 43 (Croda), Nikkol SO-15 (Nikko) (3.7)); Sorbitan tristearate (Span-65 (Atlas/ICI) Crill 35 (Croda), Nikkol SS-30 (Nikko) (2.1)); Sorbitan monoisostearate (Crill 6 (Croda), Nikkol SI-10 (Nikko) (4.7)); Sorbitan sesquistearate (Nikkol SS-15 (Nikko) (4.2)); and combinations thereof.

Lower Alcohol Fatty Acid Esters: (listed as compound name (common commercial product name (supplier) (HLB)): Ethyl oleate ((Crodamol EO (Croda), Nikkol EOO (Nikko) (<10)); Isopropyl myristate (Crodamol IPM (Croda) (<10)); Isopropyl palmitate (Crodamol IPP (Croda) (<10)); Ethyl linoleate (Nikkol VF-E (Nikko) (<10)); Isopropyl linoleate (Nikkol VF-IP (Nikko) (<10)); and combinations thereof Ionic Surfactants: (listed as compound name (HLB) Fatty acid salts (>10)); Sodium caproate; Sodium caprylate; Sodium caprate; Sodium laurate; Sodium myristate)); Sodium myristolate; Sodium palmitate; Sodium palmitoleate; Sodium oleate (18); Sodium ricinoleate)); Sodium linoleate; Sodium linolenate; Sodium stearate; Sodium lauryl sulfate (40); Sodium tetradecyl sulfate; Sodium lauryl sarcosinate; Sodium dioctyl sulfosuccinate; Bile Salts (>10); Sodium cholate; Sodium taurocholate; Sodium glycocholate; Sodium deoxycholate; Sodium taurodeoxycholate; Sodium glycodeoxycholate; Sodium ursodeoxycholate; Sodium chenodeoxycholate; Sodium taurochenodeoxycholate; Sodium glyco cheno deoxycholate; Sodium cholylsarcosinate; Sodium N-methyl taurocholate; and combinations thereof.

Phospholipids: such as Egg/Soy lecithin (Epikuron™; Ovothin™); Lyso egg/soy lecithin; Hydroxylated lecithin; Lysophosphatidylcholine; Cardiolipin; Sphingomyelin; Phosphatidylcholine; Phosphatidyl ethanolamine; Phosphatidic acid; Phosphatidyl glycerol; Phosphatidyl serine, and combinations thereof.

Phosphoric Acid Esters: Diethanolammonium polyoxyethylene-10 oleyl ether phosphate; Esterification products of fatty alcohols or fatty alcohol ethoxylates with phosphoric acid or anhydride.

Carboxylates, such as: Ether carboxylates (by oxidation of terminal OH group of fatty alcohol ethoxylates) Succinylated monoglycerides; Sodium stearyl fumarate; Stearoyl propylene glycol hydrogen succinate; Mono/diacetylated tartaric acid esters of mono- and diglycerides; Citric acid esters of mono-, diglycerides; Glyceryl-lacto esters of fatty acids; and combinations thereof.

Acyl lactylates such as: lactylic esters of fatty acids; calcium/sodium stearoyl-2-lactylate; calcium/sodium stearoyl lactylate; alginate salts like sodium alginate, calcium alginate and others; and combinations thereof.

Hydrophilic Polymers such as: carboxyvinyl polymer, polyvinylpyrrolidone, polyvinyl alcohol, methacrylic acid copolymers, macrogol, starch, gelatin, dextrin, pullulan, agar, acacia, poly(ethylene glycol), poly(ethylene oxide), poly(vinyl alcohol), poly(ethylene-co-vinyl alcohol), poly (acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), or poly(ethylene oxide)-co-poly (propylene oxide); block copolymers, graft copolymers of lactic acid, glycolic acid, epsilon-caprolactone, lactic-coglycolic acid oligomers, trimethylene carbonate, anhydrides, and amino acids acrylates, benzoquinones, naphthoquinones and the like; N-vinylpyrrolidone-co-vinyl alcohol, poly(ethylene-co-vinyl alcohol); acrylic or methacrylic acid copolymers; carbomers, Chitosan, methacrylates (Eudragits), and combinations thereof.

Acids such as: acetic acid, hydrochloric acid, hydrobromic acid, hydriodic acid, phosphoric acid, sulfuric acid, nitric acid, acrylic acid, adipic acid, alginic acid, alkanesulfonic acid, an amino acid, ascorbic acid, benzoic acid, boric acid, butyric acid, carbonic acid, citric acid, fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, salts thereof, and mixtures thereof.

Bases such as: amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, and mixtures of combinations thereof.

Chelating Agents such as: Sodium EDTA, Dieditate Sodium, and mixtures or combinations thereof. Complexing Agents such as: Hydroxypropyl Cyclodextrin, Hydroxy propyl beta Cyclodextrin, sulfabutyl ether cyclodextrin, and mixtures and combinations thereof. Salts such as: salts of acids, bases, salts of fatty acids, fatty acid glycerides, Salts of bile acids, and mixtures and combinations thereof.

Amides such as: for example 2-pyrrolidone, 2-piperidone, epsilon-caprolactam, N-alkylpyrrolidone, N-hydroxyalkylpyrrolidone, N-alkylpiperidone, N-alkylcaprolactam, dimethylacetamide, polyvinylpyrrolidone and the like.

Alcohols such as: ethanol, isopropanol, butanol, benzyl alcohol, ethylene glycol, propylene glycol, glycerol, sorbitol, mannitol, dimethyl isosorbide, polyethylene glycol, fatty acid alcohol, vinyl alcohol polypropylene glycol, polyvinyl-alcohol, tocopherols, cellulose cyclodextrins, other derivatives, forms, mixtures thereof, or the like.

Glycerols and Propylene Glycols such as: glycerine, propylene glycol, polypropylene glycol, polypropylene oxides, and mixtures thereof. Polyethylene Glycol (PEG) such as: PEG 300, PEG 400, PEG 4000, PEG 6000, PEG 8000, PEG 20000, and combinations thereof.

Esters such as: ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, epsilon-caprolactone and isomers thereof, delta-valerolactone and isomers thereof, beta-butyrolactone and isomers thereof; dimethyl acetamide, dimethyl isosorbide, N-methyl pyrrolidones, monooctanoin, diethylene glycol monoethyl ether, or the like.

Bile acids such as: cholate, taurocholate, glycocholate, deoxycholate, taurodeoxycholate, chenodeoxycholate, glycodeoxycholate, glycochenodeoxycholate, taurochenodeoxycholate, ursodeoxycholate, lithocholate, tauroursodeoxycholate, glycoursodeoxycholate, cholylsarcosine).

Celluloses such as: microcrystalline cellulose, ethyl cellulose (EC), methylethyl cellulose (MEC), carboxymethyl cellulose (CMC), carboxymethyl ethylcellulose (CMEC), hydroxyethyl cellulose (HEC), hydroxypropyl cellulose (HPC), cellulose acetate (CA), cellulose propionate (CPr), cellulose butyrate (CB), cellulose acetate butyrate (CAB), cellulose acetate phthalate (CAP), cellulose acetate trimellitate (CAT), hydroxypropyl methyl cellulose (HPMC), hydroxypropyl methyl cellulose phthalate (HPMCP), hydroxypropyl methyl cellulose acetate succinate (HPMCAS), hydroxypropyl methyl cellulose acetate trimellitate (HPMCAT), and ethylhydroxy ethylcellulose (EHEC), various grades of low viscosity (MW less than or equal to 50,000 daltons) and high viscosity (MW greater than 50,000 daltons) HPMC, and combinations thereof.

Cellulose Esters such as: Cellulose acetate, Cellulose Acetate Butyrate, Cellulose acetate phthalate, Hydroxypropyl methylcellulose phthalate, and combinations thereof.

Mucoadhesive Polymers such as for example tocopherols such as for example tocopherol, tocopherol acetate, tocopherol succinate, and combinations thereof.

Amino Acids and Modified Amino acids such as: aminoboronic acid derivatives, n-acetylcysteine, and mixtures thereof.

Sugars such as: maltose, sucrose, dextrose, lactose, fructose, mannitol, sucralose, fructalose, trehelose, dextrose, maltodextrose, and combinations thereof.

Sugar Alcohols such as: mannitol, xylitol, sorbitol, combinations thereof, and the like Osmotic agents such as: Hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP) and crosslinked PVP, polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carbox cellulose (CEC), sodium alginate, polycarbophil, gelatin, xanthan gum, and sodium starch glycolate and the like.

Other carriers such as: dibasic calcium phosphate, croscarmellose sodium, sodium starch glycolate, sodium alginate, phospholipids, lecithins, proteins (e.g., collagen, gelatin, Zein, gluten, mussel protein, lipoprotein); carbohydrates (e.g., alginates, carrageenan, cellulose derivatives, pectin, starch); gums (e.g., xanthan gum, gum Arabic, gum tragacanth, gum acacia); spermaceti; natural or synthetic waxes; carnuaba wax; fatty acids (e.g., stearic acid, hydroxystearic acid); Magnesium stearate, calcium stearate, titanium dioxide, polyacrylic acid, silicates, magnesium aluminum silicates, siloxanes, mimeticones, paraffins, fatty alcohols; dibutyl phthalate; dibutyl sebacate; diethyl phthalate; dimethyl phthalate; triethyl citrate; butyl and glycol esters of fatty acids; mineral oil; cetyl alcohol; stearyl alcohol; camphor oil; triethyl citrate, shellacs, benzalkonium chloride, methyl paraben, propyl paraben, sodium benzoate and the like.

In one embodiment, the pharmaceutical composition or oral dosage form can be formulated to include at least one of the following preferred carriers: citric acid, maleic acid, tartaric acid, ascorbic acid, lactic acid, and salts thereof, potassium hydroxide, sodium hydroxide, sodium hydrogen carbonate, calcium carbonate, silicon dioxide, magnesium aluminum silicate, triethylamine, fatty acid glycerides, pyrrolidone, polyvinylpyrrolidone, ethyl alcohol, benzyl alcohol, glycerol, propylene glycol, polyethylene glycol, triethylcitrate, triacetin, benzyl benzoate, bile acid, salts of bile acid, ethyl cellulose, hydroxypropyl ethyl cellulose, cellulose esters, carbomer, methacrylates, polyvinyl alcohol, gelatin, distearin, monopalmitolein tocopherol, tocopherol succinate, corn oil, olive oil, peanut oil, safflower oil, sesame oil, soybean oil, hydrogenated castor oil, glyceryl tricaprate, glyceryl trilinoleate, glyceryl tricaprylate/caprate, glyceryl tricaprylate/caprate/linoleate, saturated polyglycolized glycerides, linoleic glycerides, caprylic/capric glycerides, capric acid, caprylic acid, palmitic acid, Lauric acid, stearic acid, linoleic acid, oleic acid, arachidonic acid, eicosapentaenoic acid, docosahexaenoic acid, glyceryl monooleate, glyceryl monolinoleate, glyceryl monolaurate, glycerol monostearate, glyceryl distearate, glyceryl palmitostearate, glyceryl laurate, glyceryl caprylate, PEG-6 corn oil, PEG-6 apricot kernel oil, stearoyl macrogol glyceride, PEG-20 sorbitan monostearate, PEG-40 hydrogenated castor oil, PEG-35 castor oil, sodium oleate, sodium lauryl sulfate, sodium lauryl sarcosinate, sodium dioctyl sulfosuccinate, polyglyceryl-3 oleate, polyglyceryl-10 oleate, polyglyceryl-6 dioleate, polyglyceryl-10 mono, dioleate, poloxamer 188, poloxamer 108, poloxamer 182, propylene glycol monocaprylate, propylene glycol monolaurate, propylene glycol dicaprylate/dicaprate, propylene glycol caprylate/caprate, sorbitan monolaurate, sorbitan monopalmitate, sorbitan monooleate, sorbitan monostearate, sorbitan sesquioleate, sorbitan sesquistearate, maltose, sucrose, fructose, mannitol, xylitol, and combinations thereof.

In one embodiment, the pharmaceutical compositions or oral dosage forms of the present invention can be formulated to include a hydrophilic additive. In another embodiment, the hydrophilic additive can be a hydrophilic surfactant. In one embodiment, when the hydrophilic additive includes a hydrophilic surfactant, the hydrophilic surfactant does not appreciably solubilize the ester of 17-hydroxyprogesterone. Non-limiting examples of hydrophilic additives include salts of citric acid, maleic acid, tartaric acid, acetic acid, ascorbic acid, benzoic acid and lactic acid, potassium hydroxide, sodium hydroxide, sodium hydrogen carbonate, calcium carbonate, silicon dioxide, magnesium aluminum silicate, hydroxypropyl cyclodextrin, fatty acid glycerides, salts of bile acids, pyrrolidone, polyvinylpyrrolidone, ethyl alcohol, benzyl alcohol, glycerol, propylene glycol, polyethylene glycol methyl cellulose, hydroxypropyl methyl cellulose, cellulose ssters, carbomer, chitosan, methacrylates, polyvinyl alcohol, gelatin, PEG-8 caprylic/capric glycerides, lauroyl macrogol-32 glyceride, stearoyl macrogol glyceride, PEG-40 hydrogenated castor oil, PEG-35 castor oil, sodium oleate, sodium lauryl sulfate, sodium lauryl sarcosinate, sodium dioctyl sulfosuccinate, PEG-10 laurate, PEG-20 oleate, PEG-30 stearate, PEG-40 laurate, PEG-20 glyceryl laurate, PEG-20 glyceryl tearate, PEG-40 glyceryl laurate, PEG-20 glyceryl oleate, PEG-10 sorbitan laurate, PEG-20 sorbitan monolaurate, PEG-20 sorbitan monooleate, polyglyceryl-10 oleate, polyglyceryl-10 mono, dioleate, poloxamer 188, poloxamer 108, maltose, sucrose, fructose, mannitol, xylitol, and combinations thereof.

In another particular embodiment, the carrier can include a hydrophilic surfactant that is an ionic or non-ionic surfactant. Non-limiting examples of hydrophilic surfactants include proteins, gelatin, salts of bile acids, PEG-8 caprylic/capric glycerides, lauroyl macrogol-32 glyceride, stearoyl macrogol glyceride, PEG-40 hydrogenated castor oil, PEG-35 castor oil, sodium oleate, sodium lauryl sulfate, sodium lauryl sarcosinate, sodium dioctyl sulfosuccinate, PEG-10 laurate, PEG-20 oleate, PEG-30 stearate, PEG-40 laurate, PEG-20 glyceryl laurate, PEG-20 glyceryl tearate, PEG-40 glyceryl laurate, PEG-20 glyceryl oleate, PEG-10 sorbitan laurate, PEG-20 sorbitan monolaurate, PEG-20 sorbitan monooleate, polyglyceryl-10 oleate, polyglyceryl-10 mono, dioleate, poloxamer 188, poloxamer 108, and combinations thereof.

In one embodiment, the hydrophilic additive can be free of hydrophilic surfactants, and can be citric acid, maleic acid, tartaric acid, acetic acid, ascorbic acid, benzoic acid, lactic acid, potassium hydroxide, sodium hydroxide, sodium hydrogen carbonate, calcium carbonate, silicon dioxide, magnesium aluminum silicate, hydroxypropyl cyclodextrin, pyrrolidone, polyvinylpyrrolidone, ethyl alcohol, benzyl alcohol, glycerol, propylene glycol, polyethylene glycol, methyl cellulose, hydroxypropyl methyl cellulose, cellulose esters, carbomer, chitosan, methacrylates, polyvinyl alcohol, gelatin, maltose, sucrose, fructose, mannitol, xylitol, and combinations thereof.

In another embodiment, the carrier of the pharmaceutical compositions or oral dosage forms can include a lipophilic additive. Non-limiting examples of lipophilic additives include tributylcitrate, triethylcitrate, triacetin, ethyl cellulose, cellulose esters, cellulose acetate, cellulose acetates butyrate, cellulose acetate phthalate, hydroxypropyl methylcellulose phthalate, tocopherol, tocopherol acetate, tocopherol succinate, corn oil, olive oil, peanut oil, safflower oil, sesame oil, soybean oil, hydrogenated castor oil, glyceryl tricaprate, glyceryl trilaurate, glyceryl trioleate, glyceryl trilinoleate, glyceryl tricaprylate/caprate, glyceryl tricaprylate/caprate/laurate, glyceryl tricaprylate/caprate/linoleate, glyceryl tricaprylate/caprate/stearate, saturated polyglycolized glycerides linoleic glycerides, caprylic/capric glycerides capric acid, caprylic acid, palmitic acid, lauric acid, stearic acid, linoleic acid, oleic acid, arachidonic acid, eicosapentaenoic acid, docosahexaenoic acid, glyceryl monooleate, glyceryl monolinoleate, glyceryl monolaurate, glycerol monostearate, glyceryl distearate, glyceryl palmitostearate, glyceryl laurate, glyceryl caprylate, distearin, monopalmitolein, monolaurin, ethyl oleate, PEG-6 corn oil, PEG-6 apricot kernel oil, PEG-4 caprylic/capric triglyceride, PEG-20 sorbitan monostearate, PEG-4 laurate, PEG-6 dilaurate, polyglyceryl-3 oleate, polyglyceryl-6 dioleate, poloxamer 182, propylene glycol monocaprylate, propylene glycol monolaurate, propylene glycol dicaprylate/dicaprate, propylene glycol caprylate/caprate, sorbitan monolaurate, sorbitan monopalmitate, sorbitan monooleate, sorbitan monostearate, sorbitan sesquioleate, sorbitan sesquistearate, and combinations thereof. In one embodiment, the carrier of the current invention can include at least 50 wt % of lipophilic additive.

In a particular embodiment, the lipophilic additive is at least one agent selected from tributylcitrate, triethylcitrate, triacetin, ethyl cellulose, cellulose esters, cellulose acetate, cellulose acetates butyrate, cellulose acetate phthalate, hydroxypropyl methylcellulose phthalate, tocopherol, tocopherol acetate, tocopherol succinate, triglycerides, corn oil, olive oil, peanut oil, safflower oil, sesame oil, soybean oil, hydrogenated castor oil, glyceryl tricaprate, glyceryl trilaurate, glyceryl trioleate, glyceryl trilinoleate, glyceryl tricaprylate/caprate, glyceryl tricaprylate/caprate/laurate, glyceryl tricaprylate/caprate/linoleate, glyceryl tricaprylate/caprate/stearate, saturated polyglycolized glycerides linoleic glycerides, caprylic/capric glycerides, capric acid, caprylic acid, palmitic acid, lauric acid, stearic acid, linoleic acid, oleic acid, arachidonic acid, eicosapentaenoic acid, docosahexaenoic acid, glyceryl distearate, glyceryl palmitostearate, distearin, tristearin, paraffin oil, bees wax, animal fat, phytosterol, cholesterol, shellac and combinations thereof.

In a particular embodiment, the lipophilic additive is a triglyceride. Non-limiting examples of triglycerides suitable for this invention include corn oil, olive oil, peanut oil, palm oil, coconut oil, arachis oil, safflower oil, sesame oil, soybean oil, castor oil, primrose oil, cotton seed oil, vegetable oil, borage oil, linseed oil, flax seed oil, omega oils, partially or fully hydrogenated castor oil, fish oil, shark oil, whale oil, seal oil, glyceryl tricaprate, glyceryl trilaurate, glyceryl trioleate, glyceryl trilinoleate, glyceryl tricaprylate/caprate, glyceryl tricaprylate/caprate/laurate, glyceryl tricaprylate/caprate/linoleate, glyceryl tricaprylate/caprate/stearate, saturated polyglycolized glycerides linoleic glycerides, caprylic/capric glycerides, tristearin and the like, and combinations thereof In one embodiment, the lipophilic additive can be free of lipophilic surfactants. In one particular embodiment, the carrier is a lipophilic surfactant. Non-limiting examples of lipophilic surfactants suitable for this invention include tributylcitrate, triethylcitrate, triacetin, ethyl cellulose, cellulose esters, cellulose acetate, cellulose acetates butyrate, benzyl benzoate, cellulose acetate phthalate, hydroxypropyl methylcellulose phthalate, tocopherol, tocopherol acetate, tocopherol succinate, corn oil, olive oil, peanut oil, safflower oil, sesame oil, soybean oil, hydrogenated castor oil, glyceryl tricaprate, glyceryl trilaurate, glyceryl trioleate, glyceryl trilinoleate, glyceryl tricaprylate/caprate, glyceryl tricaprylate/caprate/laurate, glyceryl tricaprylate/caprate/linoleate, glyceryl tricaprylate/caprate/stearate, saturated polyglycolized glycerides linoleic glycerides, caprylic/capric glycerides capric acid, caprylic acid, palmitic acid, lauric acid, stearic acid, linoleic acid, oleic acid, arachidonic acid, eicosapentaenoic acid, docosahexaenoic acid, glyceryl monooleate, glyceryl monolinoleate, glyceryl monolaurate, glycerol monostearate, glyceryl distearate, glyceryl palmitostearate, glyceryl laurate, glyceryl caprylate, distearin, monopalmitolein, monolaurin, ethyl oleate, PEG-6 corn oil, PEG-6 apricot kernel oil, PEG-4 caprylic/capric triglyceride, PEG-20 sorbitan monostearate, PEG-4 laurate, PEG-6 dilaurate, polyglyceryl-3 oleate, polyglyceryl-6 dioleate, poloxamer 182, propylene glycol monocaprylate, propylene glycol monolaurate, propylene glycol dicaprylate/dicaprate, propylene glycol caprylate/caprate, sorbitan monolaurate, sorbitan monopalmitate, sorbitan monooleate, sorbitan monostearate, sorbitan sesquioleate, sorbitan sesquistearate, and combinations thereof.

In another particular embodiment, the compositions or dosage form of the present invention can be free of triglycerides, or substantially free of triglycerides. Thus, in one embodiment, the present invention does not include lipophilic or hydrophilic additive, which contain triglycerides as an intended or added component. However, it should be appreciated that the present invention does not exclude the use of lipophilic or hydrophilic additives, which contain small amounts of triglycerides as impurities or as unreacted starting material. It is expected that when such lipophilic or hydrophilic additive is used in the compositions of the present invention, the total triglyceride content does not exceed 5% by weight of the composition or dosage form. Thus, "substantially triglyceride-free" should be understood as meaning free of added triglycerides, and the triglyceride impurity from the lipophilic or hydrophilic additives constitute about 5%, or less than 5%, less than 2%, or preferably 0% (triglyceride free), by weight of the composition. Further, the present invention does not exclude lipophilic or hydrophilic additives that are derivatives of triglycerides, such as for example polyethylene glycol or propylene glycol derivatives of triglycerides; while these derivatized triglycerides may have surfactant properties, the triglycerides are not surfactants by themselves.

Non-limiting examples of such lipophilic additives include tributylcitrate, triethylcitrate, triacetin, ethyl cellulose, cellulose esters, cellulose acetate, cellulose acetates butyrate, cellulose acetate phthalate, hydroxypropyl methylcellulose phthalate, tocopherol, tocopherol acetate, tocopherol succinate, saturated polyglycolized glycerides linoleic glycerides, caprylic/capric glycerides capric acid, caprylic acid, palmitic acid, lauric acid, stearic acid, linoleic acid, oleic acid, arachidonic acid, eicosapentaenoic acid, benzyl benzoate, docosahexaenoic acid, glyceryl monooleate, glyceryl monolinoleate, glyceryl monolaurate, glycerol monostearate, glyceryl distearate, glyceryl palmitostearate, glyceryl laurate, glyceryl caprylate, distearin, monopalmitolein, monolaurin, ethyl oleate, PEG-6 corn oil, PEG-6 apricot kernel oil, PEG-4 caprylic/capric triglyceride, PEG-20 sorbitan monostearate, PEG-4 laurate, PEG-6 dilaurate, polyglyceryl-3 oleate, polyglyceryl-6 dioleate, poloxamer 182, propylene glycol monocaprylate, propylene glycol monolaurate, propylene glycol dicaprylate/dicaprate, propylene glycol caprylate/caprate, sorbitan monolaurate, sorbitan monopalmitate, sorbitan monooleate, sorbitan monostearate, sorbitan sesquioleate, sorbitan sesquistearate, and combinations thereof.

In some embodiments, the carrier of the current invention can include a control release agent. In a particular embodiment, the control release agent can be selected from the group consisting of the said hydrophilic additives or lipophilic additives or a mixture thereof. In another particular embodiment, the compositions or dosage forms of the present invention can be free of lipophilic surfactant. In another particular embodiment, the compositions or dosage form of the present invention can be free of lipophilic additive.

As discussed above, in some embodiments, the pharmaceutical compositions and the oral dosage forms of the present disclosure can include at least one hydrophilic additive and at least one lipophilic additive. In one embodiment, when both a hydrophilic additive and a lipophilic additive are present, they can be present at a lipophilic additive to hydrophilic additive ratio of about 99:1 to about 1:99. In one embodiment, the lipophilic additive to hydrophilic additive ratio can be about 95:5 to about 5:95. In another embodiment, the lipophilic additive to hydrophilic additive ratio can be about 90:10 to about 10:90. In one embodiment, the lipophilic additive to hydrophilic additive ratio can be of about 90:10 to about 1:99. In another specific embodiment, the lipophilic additive to hydrophilic additive ratio can be of about 80:20 to about 20:80. In another specific embodiment, the lipophilic additive to hydrophilic additive ratio can be of about 70:30 to about 30:70. In another specific embodiment, the lipophilic additive to hydrophilic additive ratio can be of about 60:40 to about 40:60. In another specific embodiment, the lipophilic additive to hydrophilic additive ratio can be about 50:50.

In an additional embodiment, when both a hydrophilic surfactant and a lipophilic additive are present, they can be present in amounts such that when 1 part by weight of the mixture of the hydrophilic surfactant and lipophilic additive is mixed 99 parts of an aqueous diluent, the dispersion so obtained so obtained can be colloidal, hazy or unclear. For example, the aqueous diluent used for dispersion is either water or 0.5% w/v sodium lauryl sulfate in water. In a specific embodiment, the dispersion can exhibit an absorbance greater than 0.1 when determined using a spectrophotometer at 400 nm. In another specific embodiment, the absorbance is greater than 0.3 at 400 nm. In another embodiment, the mean particle size of the dispersion is about 60 nm or more. In another specific embodiment, the mean particle size of the dispersion is about 100 nm or more. In another specific embodiment, the mean particle size of the dispersion is about 150 nm or more. In yet another specific embodiment, the mean particle size of the dispersion is about 200 nm or more. In yet another specific embodiment, the mean particle size of the dispersion is about 250 nm or more. For example, the aqueous diluent used for dispersion is either water or 0.5% w/v sodium lauryl sulfate in water. For the purpose of this invention, the dispersion is deemed clear if it appears clear to the naked eye. In one embodiment, the dispersion can be clear.

In one embodiment, the carrier can be present in an amount sufficient to solubilize the ester of 17 hydroxyprogesterone. In some aspects, the carrier of the present invention aids in solubilizing a significant amount of the ester of 17-hydroxyprogesterone in the composition. In one embodiment, the carrier can solubilize 20 wt % or more of the amount of the ester of 17-hydrxoyprogesterone. In another embodiment, the carrier can aid loading of greater than about 10% w/w of the ester in the composition and/or dosage form. In another embodiment, the loading achieved by the carrier can be greater than about 12% w/w of the composition and/or dosage form. In another embodiment, the loading achieved by the carrier can be greater than about 15% w/w of the composition and/or dosage form. In another embodiment, the loading attained by inclusion of the carrier can be greater than about 18% w/w of the composition and/or dosage form. In further embodiments, the loading attained by inclusion of the carrier can be greater than about 20%; greater than about 25%, greater than about 30%, greater than about 35%, greater than about 40%, greater than about 50%, greater than about 60%, greater than about 75%, or greater than about 90%, with each percentage based on w/w of the composition and/or dosage form.

In one embodiment, the carrier can include benzyl alcohol, benzyl benzoate, mixtures thereof. In another embodiment, the carrier can include benzyl alcohol, benzyl benzoate, or mixtures thereof and the amount of the ester of 17-hydroxyprogesterone can be between about 5 to about 80% w/w of the total composition. In one embodiment, when the carrier includes benzyl alcohol, benzyl benzoate, or mixtures thereof, the amount of the ester of 17-hydroxyprogesterone can be between about 5 to about 80% w/w of the total composition. In one embodiment, the amount of the ester of 17-hydroxyprogesterone can be between 5% to about 60% w/w of the total composition. In another specific embodiment, when the carrier includes benzyl alcohol, benzyl benzoate, or mixtures thereof, the amount of the ester of 17-hydroxyprogesterone can be between about 5 to about 40% w/w of the total composition. In another specific embodiment, when the carrier includes benzyl alcohol, benzyl benzoate, or mixtures thereof, the amount of the ester of 17-hydroxyprogesterone can be between about 5 to about 30% w/w of the total composition. In another specific embodiment, when the carrier includes benzyl alcohol, benzyl benzoate, or mixtures thereof, the amount of the ester of 17-hydroxyprogesterone can be between about 5 to about 25% w/w of the total composition. In one specific embodiment, when the carrier includes benzyl alcohol, benzyl benzoate, or mixtures thereof, the ester of 17-hydroxyprogesterone can be fully solubilized in the composition and/or the dosage form. In another specific embodiment, the ester of 17-hydroxyprogesterone can be partially solubilized in the dosage form. In another specific embodiment, the ester of 17-hydroxyprogesterone can be 17-hydroxyprogesterone caproate.

In one embodiment the ratio of the amount of the ester of 17-hydroxyprogesterone to the sum of the amounts of benzyl alcohol and benzyl benzoate present in the composition or oral dosage form can be about 1:0.01 (W/W) to about 1:5 (W/W). In another embodiment, the ratio can be about 1:0.01 (W/W) to about 1:3.5 (W/W). In another embodiment, the ratio of the amount of the ester of 17-hydroxyprogesterone to the sum of the amounts of benzyl alcohol and benzyl benzoate present in the composition or oral dosage form can be about 1:0.01 (W/W) to about 1:2.5 (W/W). In another embodiment, the ratio of the amount of the ester of 17-hydroxyprogesterone to the sum of the amounts of benzyl alcohol and benzyl benzoate present in the composition or oral dosage form can be about 1:0.01 to about 1:2 (W/W).

In one embodiment, the pharmaceutical composition or unit dosage form described herein having an ester of 17-alpha-hydroxyprogesterone is particle size physically stable. The term "particle size physically stable" means that, on storage, there is no evidence of substantial particle growth or agglomeration of the API particles. Substantial particle growth or agglomeration refers to an increase in particle size of greater than 10%, 20%, 30%, 40%, 50%, 75%, 100%, 150%, 200%, or 300%. One particular apparatus that can be used is the Sympatec Dry Dispersion Size Analyser. The term "particle agglomeration inhibitor" refers to agents, which are used to stabilize an API in order to reduce or prevent the API from agglomerating or aggregating. A stabilizing agent generally reduces the cohesion between particles and prevents fine particles becoming attached to each other. Stabilizing agents include metal stearates such as magnesium stearate and calcium stearate, ionic and non-ionic surfactants, and polymers such as cellulose ethers, PVP or PVA. Typically, a particle agglomeration inhibitor can be included in an amount to provide particle size stability.

Other particle agglomeration inhibitors, include, but are not limited to, povidone, crosslinked PVP (crospovidone), cross linked carmellose (croscarmellose), sodium starch glycolate, Povidone (PVP), Povidone K12, Povidone K17, Povidone K25, Povidone K29/32 and Povidone K30, stearic acid, magnesium stearate, calcium stearate, sodium stearyl fumarate, sodium stearyl lactylate, zinc stearate, sodium stearate or lithium stearate, other solid state fatty acids such as oleic acid, lauric acid, palmitic acid, erucic acid, behenic acid, or derivatives (such as esters and salts), Amino acids such as leucine, isoleucine, lysine, valine, methionine, phenylalanine, aspartame or acesulfame K.

In one embodiment, the pharmaceutical composition or unit dosage form described herein having an ester of 17-alpha-hydroxyprogesterone is crystallization stable. The term "crystallization stable" means that, on storage, there is no evidence of substantial crystallization of the API particles. Substantial crystallization refers to an increase in crystalline particle size of greater than 10%, 20%, 30%, 40%, 50%, 75%, 100%, 150%, 200%, or 300%. In one aspect, the pharmaceutical composition or unit dosage form described herein having an ester of 17-alpha-hydroxyprogesterone (e.g., 17-hydroxyprogesterone caproate) has a crystallization inhibitor. The term "crystallization inhibitor," as used herein, means an agent that facilitates prevention of crystallization of the API. Examples of crystallization inhibitors include, but are not limited to polyvinylpyrrolidone (PVP or povidone), including homo- and copolymers of polyvinylpyrrolidone and homopolymers or copolymers of N-vinylpyrrolidone; crospovidone; gums; cellulose derivatives (e.g., HPMC polymers, hydroxypropyl cellulose, ethyl cellulose, hydroxyethylcellulose, sodium carboxymethyl cellulose, calcium carboxymethyl cellulose, sodium carboxymethyl cellulose); dextran; acacia; homo- and copolymers of vinyllactam, and mixtures thereof; cyclodextrins; gelatins; hypromellose phthalate; sugars; sugar alcohols including mannitol; polyhydric alcohols; polyethylene glycol (PEG); polyethylene oxides; polyoxyethylene derivatives; polyvinyl alcohol; propylene glycol derivatives and the like, SLS, Tweens, Eudragits (methacrylic acid copolymers); and combinations thereof; amino acids such as prolin. Included herein are methods of manufacturing pharmaceutical composition that reduce API particle agglomeration or crystallization. Such methods include co-milling, co-micronization, co-nanosizing, and/or solid solution.

The pharmaceutical compositions and oral dosage forms can be formulated and delivered in a variety of solid or liquid dosage forms. Non-limiting examples of such dosage forms include powder, granulate, particulate, bead, pellet, sprinkle, suspension, solution, tablet, capsule, and combinations thereof. In one embodiment, the pharmaceutical composition or oral dosage form can be in the form of a capsule. In another embodiment, the pharmaceutical composition or oral dosage form can be in the form of a tablet. In one embodiment, the dosage form is a hard or a soft capsule. The capsule can be made of conventional capsule shell materials known in the art; such materials can include, but are not limited to gelatins, celluloses, starches, methacrylates, carrageenans, polyvinyl alcohols, and the like. In another embodiment, the capsule is an immediate release dosage form. In yet another embodiment, the capsule is a controlled release dosage form. In another embodiment, the tablet is an immediate release dosage form. In another embodiment, the tablet is a controlled release dosage form.

In one embodiment, the volume of the capsule can be about 1.5 mL or less. In another embodiment, the volume of capsule can be about 1.2 mL or less. In one particular embodiment, the volume of the capsule can be about 0.8 mL or less. In another embodiment, the ratio of the weight of fill material encapsulated within the capsule to the capsule volume can be between about 0.3 g/mL to about 3.5 g/mL. In a particular embodiment, the ratio can be between 0.6 g/mL to about 2.5 g/mL. In another particular embodiment, the ratio can be between 0.6 g/mL to about 1.2 g/mL.

In another embodiment, the pharmaceutical capsule oral dosage form of the current invention can have a ratio of the amount of the ester of 17-hydroxyprogesterone in the composition to the fill volume of the capsule between about 0.02 g/mL to about 0.8 g/mL. In another embodiment, the ratio can be between about 0.02 g/mL to about 0.7 g/mL. In a specific embodiment, the ratio can be between about 0.02 g/mL to about 0.5 g/mL. In another specific embodiment, the ratio can be between about 0.05 g/mL to about 0.5 g/mL. In another specific embodiment, the ratio can be between about 0.05 g/mL to about 0.35 g/mL. In another specific embodiment, the ratio can be between about 0.05 g/mL to about 0.3 g/mL. In another specific embodiment, the ratio can be between about 0.1 g/mL to about 0.25 g/mL.

The oral dosage forms of the present invention can be formulated to include an amount of an ester of 17-hydroxyprogesterone equivalent to about 10 mg to about 800 mg of 17-hydroxyprogesterone. In one embodiment, the oral dosage form can be formulated to include an amount of ester of 17-hydroxyprogesterone equivalent to 20 mg to about 400 mg of 17-hydroxyprogesterone. The pharmaceutical composition and oral dosage forms of the present invention can be formulated to be administered to a subject in order to provide a daily dose of the ester of 17-hydroxyprogesterone that is equivalent to about 40 mg to about 3200 mg of 17-hydroxyprogesterone. In one embodiment, the oral dosage form can be a capsule and the capsule includes from about 10 mg to about 300 mg 17-hydroxyprogesterone caproate. In another embodiment, the oral dosage form can be a tablet and the tablet includes from about 20 mg to about 800 mg of 17-hydroxyprogesterone caproate. In another embodiment, the oral dosage form includes from about 20 mg to about 1200 mg of 17-hydroxyprogesterone caproate. In another embodiment, the oral dosage form can be a tablet and the tablet includes from about 100 mg to about 1000 mg of 17-hydroxyprogesterone caproate. In another embodiment, the oral dosage form includes from about 200 mg to about 900 mg of 17-hydroxyprogesterone caproate. In another embodiment, the oral dosage form includes from about 300 mg to about 900 mg of 17-hydroxyprogesterone caproate. In another embodiment, the oral dosage form includes from about 350 mg to about 800 mg of 17-hydroxyprogesterone caproate. In another embodiment, the oral dosage form includes from about 400 mg to about 800 mg of 17-hydroxyprogesterone caproate. In another embodiment, the oral dosage form includes from about 100 mg to about 400 mg of 17-hydroxyprogesterone caproate. In another embodiment, the oral dosage form includes from about 150 mg to about 350 mg of 17-hydroxyprogesterone caproate. In another embodiment, the oral dosage form includes from about 200 mg to about 375 mg of 17-hydroxyprogesterone caproate. In another embodiment, the oral dosage form includes from about 200 mg to about 475 mg of 17-hydroxyprogesterone caproate. In another embodiment, the oral dosage form includes from about 525 mg to about 850 mg of 17-hydroxyprogesterone caproate. In order to provide a desired daily dose, the pharmaceutical compositions and oral dosage forms can be formulated to be administered at various dosing intervals. In one embodiment, the compositions or oral dosage forms can be formulated for administration about once every 8 hours. In one embodiment, the compositions or oral dosage forms can be formulated for administration about three times a day. In another embodiment, the compositions or oral dosage forms can be formulated for administration to a subject, such as a human subject, once every 6 hours. In one embodiment, the compositions or oral dosage forms can be formulated for administration about four times a day. In another embodiment, the compositions or oral dosage forms can be formulated for administration about once every 12 hours. In one embodiment, the compositions or oral dosage forms can be formulated for administration about two times a day. In yet a further embodiment, the compositions or oral dosage forms can be formulated for administration about once every 24 hours. In one embodiment, the compositions or oral dosage forms can be formulated for administration about once a day. The amount of 17HPC per dosage form are as provided in the previous paragraph which can be administered as one, two, three, or four unit dosage forms per dose (e.g., each time).

In one embodiment, the oral pharmaceutical compositions comprising 17HPC and a pharmaceutically acceptable carrier when used to treat a female for one or more of the conditions described herein yields improved efficacy as compared to administration of placebo.

In one aspect, the oral dosage forms of the present invention can be used to treat pregnant female subjects who are at risk of preterm birth. The methods of treatment include the step of orally administering to the female subject the oral pharmaceutical composition. In another embodiment, the oral dosage forms can be administered to subjects in need thereof. The administration of the oral dosage form can treat at least one condition selected from preterm labor, preterm birth, infertility and miscarriage. In one embodiment, the subject receiving administration of the pharmaceutical composition or oral dosage form can be experiencing or be at risk of at least two of: singleton pregnancy, history of preterm labor and/or preterm birth, history of preterm delivery, shortened cervix, and effaced cervix, history of more at least one miscarriage, and history of multifetal gestation. The conditions and the relative treatment can be based on their primary and secondary outcome measurements associated with the administration of the ester of 17-hydroxyprogesterone.

In one embodiment, upon single administration to a human subject, the pharmaceutical compositions or oral dosage forms of the present invention comprising an ester of 17-hydroxyprogesterone can provide a 17-hydroxyprogesterone equivalent $C_{avg\text{-}24h}$ greater than about 0.7 ng/mL. In another embodiment, the oral dosage form or the composition can provide a $C_{avg\text{-}24h}$ of 17-hydroxyprogesterone equivalent greater than about 10 ng/mL. In another embodiment, the oral dosage form or the composition can provide a $C_{avg\text{-}24h}$ of 17-hydroxyprogesterone equivalent greater than about 30 ng/mL. In another embodiment, the oral dosage form or the composition can provide a $C_{avg\text{-}24h}$ of 17-hydroxyprogesterone equivalent greater than about 50 ng/mL. In yet a further embodiment, the oral dosage form or the composition can provide a $C_{avg\text{-}24h}$ of 17-hydroxyprogesterone equivalent greater than about 100 ng/mL. In one embodiment, the said 17-hydroxyprogesterone equivalent $C_{avg\text{-}24h}$ is determined by an HPLC-MS/MS method of analysis of the plasma, serum or blood samples collected following the oral administration.

In one embodiment, upon single administration to a human subject, the pharmaceutical compositions or oral dosage forms of the present invention comprising an ester of 17-hydroxyprogesterone can provide a 17-hydroxyprogesterone equivalent $C_{avg\text{-}24h}$ greater than about 0.05, 0.1, 0.5, 0.7, 1.0, 1.5, 1, 2.0, 3.0, 5.0, 10.0, 15.0, 20.0, 25.0, 30.0, 35.0, 40.0, 45.0, 50.0 60.0 or 75.0 ng/mL (or within a range defined by any two of these values). In one embodiment, the said 17-hydroxyprogesterone equivalent $C_{avg\text{-}24h}$ is determined by an HPLC-MS/MS method of analysis of the plasma, serum or blood samples collected following the oral administration.

In one embodiment, upon single administration to a human subject the pharmaceutical compositions or oral dosage forms of the present invention comprising 17-hydroxyprogesterone caproate, can provide a 17-hydroxyprogesterone caproate $C_{avg\text{-}24h}$ equal to about 1.0 ng/mL or more. In another embodiment, the oral dosage form or the composition can provide a 17-hydroxyprogesterone caproate $C_{avg\text{-}24h}$ equal to about 20 ng/mL or more. In another embodiment, the oral dosage form or the composition can provide a 17-hydroxyprogesterone caproate $C_{avg\text{-}24h}$ equal to about 50 ng/mL or more. In another embodiment, the oral dosage form or the composition can provide a 17-hydroxyprogesterone caproate $C_{avg\text{-}24h}$ equal to about 100 ng/mL or more. In one embodiment, the said 17-hydroxyprogesterone caproate $C_{avg\text{-}24h}$ is determined by an HPLC-MS/MS method of analysis of the plasma, serum or blood samples collected following the oral administration.

In one embodiment, upon single administration to a human subject the pharmaceutical compositions or oral dosage forms of the present invention comprising 17-hydroxyprogesterone caproate, can provide a 17-hydroxyprogesterone caproate $C_{avg\text{-}24h}$ greater than about 0.05, 0.1, 0.5, 0.7, 1.0, 1.5, 2.0, 3.0, 5.0, 10.0, 15.0, 20.0, 25.0, 30.0, 35.0, 40.0, 45.0, 50.0 60.0 or 75.0 ng/mL (or within a range defined by any two of these values). In one embodiment, the said 17-hydroxyprogesterone caproate $C_{avg\text{-}24h}$ is determined by an HPLC-MS/MS method of analysis of the plasma, serum or blood samples collected following the oral administration.

It was surprisingly found that the compositions and/or dosage forms of this invention provided significantly enhanced bioavailability of 17-hydroxyprogesterone caproate as a function of the oral dose of the 17 hydroxyprogesterone caproate administered to a subject. Accordingly, the compositions or dosage forms of this invention provide, upon single dose oral administration, an $AUC_{(0\text{-}24h)}$ to dose ratio of about 10 or less, wherein the dose is the amount in mg of the 17-hydroxyprogesterone caproate administered. In one embodiment, the ratio of the 17-hydroxyprogesterone caproate $AUC_{(0\text{-}24h)}$ to dose of the 17-hydroxyprogesterone caproate administered can be about 0.2 ng*h mL$^{-1}$mg$^{-1}$ to about 10 ng*h mL$^{-1}$mg$^{-1}$. In another embodiment, the ratio of the 17-hydroxyprogesterone caproate $AUC_{(0\text{-}24h)}$ to dose of the 17-hydroxyprogesterone caproate administered can be about 0.3 ng*h mL$^{-1}$mg$^{-1}$ to about 7 ng*h mL$^{-1}$mg$^1$. In a specific embodiment, the $AUC_{(0\text{-}24h)}$ to dose ratio is between about 0.5 and about 6 ng*h mL$^{-1}$mg$^{-1}$.

In another embodiment, in one aspect the compositions or dosage forms of this invention provide, upon single dose oral administration, an $AUC_{(0\text{-}24h)}$ to dose ratio of less than 10, 9, 8, 7, 6, 5, 4, 3, 2, or 1, wherein the dose is the amount in mg of the 17-hydroxyprogesterone caproate administered. In another aspect the compositions or dosage forms of this invention provide, upon single dose oral administration, an $AUC_{(0\text{-}24h)}$ to dose ratio of greater than 10, 9, 8, 7, 6, 5, 4, 3, 2, 1.75, 1.5, 1.25, 1 or 0.5, wherein the dose is the amount in mg of the 17-hydroxyprogesterone caproate administered. In one embodiment, the ratio of the 17-hydroxyprogesterone caproate $AUC_{(0\text{-}24h)}$ to dose of the 17-hydroxyprogesterone caproate administered can be about 0.01 ng*h mL$^{-1}$mg$^{-1}$ to about 5.0 ng*h mL$^{-1}$mg$^{-1}$. In another embodiment, the ratio of the 17-hydroxyprogesterone caproate $AUC_{(0\text{-}24h)}$ to dose of the 17-hydroxyprogesterone caproate administered can be about 0.05 ng*h mL$^{-1}$mg$^{-1}$ to about 3.0 ng*h mL$^{-1}$mg$^{-1}$. In a specific embodiment, the $AUC_{(0\text{-}24h)}$ to dose ratio is between about 0.1 and about 2.0 ng*h mL$^{-1}$ mg$^{-1}$. In a specific embodiment, the $AUC_{(0\text{-}24h)}$ to dose ratio is between about 0.1 and about 1.5 ng*h mL$^{-1}$mg$^{-1}$. In a specific embodiment, the $AUC_{(0\text{-}24h)}$ to dose ratio is between about 0.1 and about 1.0 ng*h mL$^{-1}$mg$^{-1}$. In a specific embodiment, the $AUC_{(0\text{-}24h)}$ to dose ratio is between about 1.5 and about 10.0 ng*h mL$^{-1}$mg$^{-1}$. In a specific embodiment, the $AUC_{(0\text{-}24h)}$ to dose ratio is between about 2.0 and about 10.0 ng*h mL$^{-1}$mg$^{-1}$. In a specific embodiment, the $AUC_{(0\text{-}24h)}$ to dose ratio is between about 3.0 and about 10.0 ng*h mL$^{-1}$mg$^{-1}$. In a specific embodiment, the $AUC_{(0\text{-}24h)}$ to dose ratio is between about 4.0 and about 10.0 ng*h mL$^{-1}$mg$^{-1}$. In a specific embodiment, the $AUC_{(0\text{-}24h)}$ to dose ratio is between about 5.0 and about 10.0 ng*h mL$^{-1}$mg$^{-1}$. In a specific embodiment, the $AUC_{(0\text{-}24h)}$ to dose ratio is between about 6.0 and about 10.0 ng*h mL$^{-1}$mg$^{-1}$. In a specific embodiment, the $AUC_{(0\text{-}24h)}$ to dose ratio is between about 7.0 and about 10.0 ng*h mL$^{-1}$mg$^{-1}$.

In one embodiment, an oral dosage form having 17-hydroxyprogesterone caproate, upon single dose administration to a human provides at least 10% of the bioavailability of an intramuscular injection of 17-hydroxyprogesterone caproate (e.g., 250 mg of 17-hydroxyprogesterone caproate in castor oil (1 or 5 mL) with or without benzyl alcohol or benzyl benzoate.)

In a specific embodiment, upon single administration of the pharmaceutical compositions or oral dosage forms containing 17-hydroxyprogesterone caproate of the present invention to a human subject under fed conditions, the oral dosage form or pharmaceutical composition can provide a 17-hydroxyprogesterone caproate $C_{avg\text{-}24h}$ of greater than about 1.0 ng/mL. In another specific embodiment, the pharmaceutical compositions or oral dosage forms containing 17-hydroxyprogesterone of the present invention can provide a steady state 17-hydroxyprogesterone caproate $C_{avg\text{-}24h}$ of greater than about 1.0 ng/mL, when administered to a human subject under fed condition. In one embodiment, the said $C_{avg\text{-}24h}$ is determined by an HPLC-MS/MS method of analysis of the plasma, serum or blood samples collected following the administration. In another embodiment, the compositions and oral dosage forms disclosed herein can be orally administered with food or without regards to the food or food content. In a specific embodiment, the compositions and oral dosage forms containing caproate ester of 17-hydroxyprogesterone as disclosed herein can be orally administered with food or without regards to the food or food content.

In another specific embodiment, the pharmaceutical compositions or oral dosage forms containing 17-hydroxyprogesterone of the present invention can provide a steady state 17-hydroxyprogesterone caproate $C_{avg\text{-}24h}$ of greater than about 0.05, 0.1, 0.5, 0.7, 1.0, 1.5, 2.0, 3.0, 5.0, 10.0, 15.0, 20.0, 25.0, 30.0, 35.0, 40.0, 45.0, 50.0, 60.0 or 75.0 ng/mL, when administered to a human subject under fed conditions (or within a range defined by any two of these values).

In one embodiment, the oral dosage form can be orally administered with food or under fed condition. In another embodiment, the composition or oral dosage form can be administered with a normal or standard meal. In a specific embodiment, the composition or oral dosage form can be administered with a food or meal, such as a meal that provides about 200 calories to about 1000 calories of energy. In another specific embodiment, the composition or oral dosage form can be administered with a meal that provides about 50% of the calories from the fat. In another embodiment, the composition or oral dosage form can be administered with a high-fat, high calorie meal. In another embodiment, the composition or oral dosage form can be administered with a standard meal that provides about 500 calories to about 1000 calories of energy. The compositional make-up of the meals that are administered can vary depending on the tastes and dietary needs of a subject. However, in some situations, it may be beneficial to administer the compositions and oral dosage forms with meals that provide no fat to about 50 g of fat. In one embodiment, the meal can provide about 3 g to about 50 g of fat. In yet a further embodiment, the meal can provide 10 g to about 50 g of fat. In yet another embodiment, the meal can provide about 15 g to about 35 g of fat. In one embodiment, when the oral dosage form is administered to a human female, it can be done without regard to the presence of or nutritional make-up of a meal. In another embodiment, when administering the oral dosage form, the total daily dose of the ester of 17 HP administered to human female subject with food or under fed condition is from about 20% to about 80% of the total daily dose administered without meals, for a similar therapeutic benefit. In a specific embodiment, the daily dose under fed condition is from about 20% to about 60% of the total daily dose administered without meals, for a similar therapeutic benefit. In another embodiment, the composition or oral dosage form can be administered without food or under fasted condition.

The oral bioavailability of the ester of 17-hydroxyprogesterone can be enhanced by using the said ester in the form of fine particulate, for example milled, micronized or nano-sized etc, in the composition and/or the dosage form of the current invention. Further, the oral bioavailability can be enhanced by using the ester along with a carrier that aids the release of at least 20% more of the ester from the composition or dosage form when exposed to an aqueous medium compared to an equivalent dose of the ester without the carrier of the current invention. In a specific embodiment the oral bioavailability of the caproate ester of 17-hydroxyprogesterone can be enhanced by using the said ester in the form of fine particulate, for example milled, micronized or nano-sized or combinations thereof in the composition and/or the dosage form of the current invention.

Accordingly, in one embodiment, the oral bioavailability of the ester of 17-hydroxyprogesterone is at least 10% more for the compositions or a dosage forms of the current invention that releases at least 20% of the ester in an aqueous medium compared to an equivalent dose of the ester present in an "untreated" particulate form such as for example as unmilled or unmicronized particulate forms. In another embodiment, the oral bioavailability of the ester of 17-hydroxyprogesterone is at least 10% more for the compositions or a dosage forms of the current invention that releases at least 20% more of the ester from the composition or dosage form when exposed to an aqueous medium compared to an equivalent dose of the ester without the carrier of the current invention. In a specific embodiment, the said ester is 17-hydroxyprogesterone caproate.

The ester of 17-hydroxyprogesterone can be a substrate to the P-glycoproteins (P-gp) the efflux transporter systems. Hence, in one embodiment, the oral bioavailability can be enhanced by at least 10% by co-administering the ester of 17-hydroxyprogesterone of the current invention with an effective amount of P-gp and/or CYP3A4 inhibiting agents e.g., star fruit, grape fruit juice, bergamottin, cafestol (as in unfiltered coffee), ketoconazole, erythromycin, mibefradil, loperamide etc.

In a further aspect, the oral pharmaceutical compositions or the oral dosage forms of the ester of 17-hydroxyprogesterone according to the current invention can be used for providing luteal support for a subject in need thereof. In one embodiment, the oral composition or the oral dosage form can be formulated to enable modulation or titration of the dose and/or dosing regimen of the ester of 17-hydroxyprogesterone for providing effective luteal support to a subject in need thereof. In one particular embodiment, the dose of the ester of 17-hydroxyprogesterone in the form of oral compositions or dosage forms of the present invention may be modulated or titrated to provide effective luteal support as needed at the during early pregnancy. In another particular embodiment, the dose of the ester of 17-hydroxyprogesterone in the form of oral compositions or dosage forms of the present invention may be modulated or titrated to provide effective luteal support as needed based on the body mass index (BMI) of the subject. In another particular embodiment, the dose of the ester of 17-hydroxyprogesterone in the form of oral compositions or dosage forms of the present invention may be modulated or titrated to provide effective luteal support as needed based on the race or ethnicity of the subject.

An example of the dose modulation or titration can be based on the total dose per day, and can include administration of a higher initial loading dose or bolus dose, followed by a lower effective standard dose. Similarly, the dose modulation or titration can be based on the total dose per week and can include administration of a higher initial loading dose or bolus dose in the initial days of the week followed by a lower effective standard dose in the later days of the week. The dosing regimen can include ramping up of (i.e. progressive increments) the daily dose in accordance with the progression of pregnancy. In a specific embodiment the ester is 17-hydroxyprogesterone caproate.

In another embodiment, the daily oral dose administered with food of 17-hydroxyprogesterone caproate is from about 40 mg to about 5000 mg. In another embodiment, the daily oral dose is from about 40 mg to about 4000 mg. In another embodiment, the daily oral dose is from about 80 mg to about 4000 mg. In another embodiment, the daily oral dose is from about 150 mg to about 4000 mg. In another embodiment, the daily oral dose is from about 250 mg to about 4000 mg. In another embodiment, the daily oral dose of is from about 500 mg to about 4000 mg. In another embodiment, the daily oral dose is from about 750 mg to about 4000 mg. In another embodiment, the daily oral dose is from about 1000 mg to about 4000 mg. In another embodiment, the daily oral dose is from about 1200 mg to about 4000 mg. In another embodiment, the daily oral dose is from about 1500 mg to about 4000 mg. In another embodiment, the daily oral dose is from about 1500 mg to about 3000 mg. In another embodiment, the daily oral dose is from about 1000 mg to about 2000 mg. In another embodiment, the daily oral dose is from about 200 mg to about 2000 mg. In another embodiment, the daily oral dose is from about 400 mg to about 2000 mg. In another embodiment, the daily oral dose is from about 800 mg to about 2000 mg.

In yet another embodiment, the total daily dose of 17HPC administered to a human subject in milligrams is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, or 1400 (or within a range defined by any two of these values). According to one aspect of this embodiment, the 17HPC is administered one, two or three times a day as one, two, three or four unit dosage forms (e.g., up to 12 unit dosage forms per day) to yield the total daily dose provided in this paragraph. In some aspects, the total daily dose can provide a 17-hydroxyprogesterone caproate $C_{avg-24h}$ of greater than about 0.1, 0.5 or 1.0 ng/mL when administered to a human subject (female or pregnant female) once, twice or three times daily as 1, 2, 3, 4, 5, 6, 7, 8, 9, or 10 unit dosage forms. In one aspect, the daily dose is from 525 mg per day to about 1400 mg per day. In one aspect, the daily dose is from 800 mg per day to about 1400 mg per day. In one aspect, the daily dose is from 900 mg per day to about 1200 mg per day. According to one aspect of this embodiment, the daily dose is provided by one or more unit dosage form, which is a tablet, capsule, solution, suspension, or sprinkle for oral administration. According to one aspect of this embodiment, the unit dosage form has a surfactant e.g., at least 1, 2, 3, 4, 5, 10, 15, 20, 30, 40, or 50 mg of a non-ionic or ionic surfactant. According to another aspect of this embodiment, the unit dosage form has one or more of (1) a lipophilic additive, (2) a diluent (3) a binder (4) a disintegrant, (5) a lubricant and (6) one or more other pharmaceutically acceptable excipients. According to one aspect of this embodiment, the unit dosage form has a lipophilic additive, binder, a diluent, a disintegrant or a combination thereof individually or together in an amount of e.g., at least 10, 20, 30, 40, 50, 100, 150, 200, 300, 400, or 500 mg (or within a range defined by any two of these values.)

In yet another embodiment, the total daily dose of 17HPC administered to a human subject in milligrams is about 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, or 1400 (or within a range defined by any two of these values). According to one aspect of this embodiment, the 17HPC is administered one, two or three times a day as one, two, three or four unit dosage forms (e.g., up to 12 unit dosage forms per day) to yield the total daily dose provided in this paragraph. In some aspects, the total daily dose can provide a 17-hydroxyprogesterone caproate $C_{avg-24h}$ of greater than about 0.1, 0.5 or 1.0 ng/mL when adminstered to a human subject (female or pregnant female) once, twice or three times daily as 1, 2, 3, 4, 5, 6, 7, 8, 9, or 10 unit dosage forms. In one aspect, the daily dose is from 525 mg per day to about 1400 mg per day. In one aspect, the daily dose is from 800 mg per day to about 1400 mg per day. In one aspect, the daily dose is from 900 mg per day to about 1200 mg per day. According to one aspect of this embodiment, the daily dose is provided by one or more unit dosage form, which is a tablet, capsule, solution, suspension, or sprinkle for oral administration. According to one aspect of this embodiment, the unit dosage form has a surfactant e.g., at least 1, 2, 3, 4, 5, 10, 15, 20, 30, 40, or 50 mg of a non-ionic or ionic surfactant. According to another aspect of this embodiment, the unit dosage form has one or more of (1) a lipophilic additive, (2) a diluent (3) a binder (4) a disintegrant, (5) a lubricant and (6) one or more other pharmaceutically acceptable excipients. According to one aspect of this embodiment, the unit dosage form has a lipophilic additive, binder, a diluent, a disintegrant or a combination thereof individually or together in an amount of e.g., at least 10, 20, 30, 40, 50, 100, 150, 200, 300, 400, or 500 mg (or within a range defined by any two of these values.)

In yet another embodiment, the total daily dose of 17HPC administered to a human subject in milligrams is about 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, or 1400 (or within a range defined by any two of these values). According to one aspect of this embodiment, the 17HPC is administered one, two or three times a day as one, two, three or four unit dosage forms (e.g., up to 12 unit dosage forms per day) to yield the total daily dose provided in this paragraph. In some aspects, the total daily dose can provide a 17-hydroxyprogesterone caproate $C_{avg\text{-}24h}$ of greater than about 0.1, 0.5 or 1.0 ng/mL when adminstered to a human subject (female or pregnant female) once, twice or three times daily as 1, 2, 3, 4, 5, 6, 7, 8, 9, or 10 unit dosage forms. In one aspect, the daily dose is from 525 mg per day to about 1400 mg per day. In one aspect, the daily dose is from 800 mg per day to about 1400 mg per day. In one aspect, the daily dose is from 900 mg per day to about 1200 mg per day. According to one aspect of this embodiment, the daily dose is provided by one or more unit dosage form, which is a tablet, capsule, solution, suspension, or sprinkle for oral administration. According to one aspect of this embodiment, the unit dosage form has a surfactant e.g., at least 1, 2, 3, 4, 5, 10, 15, 20, 30, 40, or 50 mg of a non-ionic or ionic surfactant. According to another aspect of this embodiment, the unit dosage form has one or more of (1) a lipophilic additive, (2) a diluent (3) a binder (4) a disintegrant, (5) a lubricant and (6) one or more other pharmaceutically acceptable excipients. According to one aspect of this embodiment, the unit dosage form has a lipophilic additive, binder, a diluent, a disintegrant or a combination thereof individually or together in an amount of e.g., at least 10, 20, 30, 40, 50, 100, 150, 200, 300, 400, or 500 mg (or within a range defined by any two of these values.)

In again another embodiment, a unit dosage form (e.g., tablet, capsule, caplet etc.) is provided having a milligram amount of 17HPC of about 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, or 900 (or within a range defined by any two of these values). In some aspects, the oral dosage form or pharmaceutical composition can provide a 17-hydroxyprogesterone caproate $C_{avg\text{-}24h}$ of greater than about 0.1, 0.5 or 1.0 ng/mL when adminstered to a human subject (female or pregnant female) once or twice daily as 1, 2, 3, 4, 5, 6, 7, 8, 9, or 10 unit dosage forms. In one aspect, the release of 17HPC from the unit dosage form is tested using a USP Type II apparatus at 50 or 100 rpm in about 1000 mL of from about 2% to about 16% (e.g., 2%, 4%, 6%, 8%, 10%, 12%, 14% or 16%) Triton X-100 solution in water at a specific temperature e.g., 20.0, 37.0 or 40.0° C. (±0.5). In a specific aspect, the unit dosage form release greater than 5%, 10%, 15%, 20%, 25%, 30%, 35%, 40%, 45%, or 50% at one hour. According to one aspect of this embodiment, the unit dosage form has a surfactant e.g., at least 1, 2, 3, 4, 5, 10, 15, 20, 30, 40, or 50 mg of a non-ionic or ionic surfactant. According to another aspect of this embodiment, the unit dosage form has one or more of (1) a lipophilic additive, (2) a diluent (3) a binder (4) a disintegrant, (5) a lubricant and (6) one or more other pharmaceutically acceptable excipients. According to one aspect of this embodiment, the unit dosage form has a lipophilic additive, binder, a diluent, a disintegrant or a combination thereof individually or together in an amount of e.g., at least 10, 20, 30, 40, 50, 100, 150, 200, 300, 400, or 500 mg (or within a range defined by any two of these values.)

In again another embodiment, a unit dosage form (e.g., tablet, capsule, caplet etc.) is provided having a milligram amount of 17HPC of about 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799 or 800 (or within a range defined by any two of these values). In some aspects, the oral dosage form or pharmaceutical composition can provide a 17-hydroxyprogesterone caproate $C_{avg\text{-}24h}$ of greater than about 0.1, 0.5 or 1.0 ng/mL when adminstered to a human subject (female or pregnant female) once or twice daily as 1, 2, 3, 4, 5, 6, 7, 8, 9, or 10 unit dosage forms. In one aspect, the release of of 17HPC from the unit dosage form is tested using a USP Type II apparatus at 50 or 100 rpm in about 1000 mL of from about 2% to about 16% (e.g., 2%, 4%, 6%, 8%, 10%, 12%, 14% or 16%) Triton X-100 solution in water at a specific temperature e.g., 20.0, 37.0 or 40.0° C. (±0.5). In a specific aspect, the unit dosage form release greater than 5%, 10%, 15%, 20%, 25%, 30%, 35%, 40%, 45%, or 50% at one hour. According to one aspect of this embodiment, the unit dosage form has a surfactant e.g., at least 1, 2, 3, 4, 5, 10, 15, 20, 30, 40, or 50 mg of a non-ionic or ionic surfactant. According to another aspect of this embodiment, the unit dosage form has one or more of (1) a lipophilic additive, (2) a diluent (3) a binder (4) a disintegrant, (5) a lubricant and (6) one or more other pharmaceutically acceptable excipients. According to one aspect of this embodiment, the unit dosage form has a lipophilic additive, binder, a diluent, a disintegrant or a combination thereof individually or together in an amount of e.g., at least 10, 20, 30, 40, 50, 100, 150, 200, 300, 400, or 500 mg (or within a range defined by any two of these values.)

In again another embodiment, a unit dosage form (e.g., tablet, capsule, caplet etc.) is provided having a milligram amount of 17HPC of about 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, or 700. In some aspects, the oral dosage form or pharmaceutical composition can provide a 17-hydroxyprogesterone caproate $C_{avg\text{-}24h}$ of greater than about 0.1, 0.5 or 1.0 ng/mL when adminstered to a human subject (female or pregnant female) once or twice daily as 1, 2, 3, 4, 5, 6, 7, 8, 9, or 10 unit dosage forms. In one aspect, the release of 17HPC from the unit dosage form is tested using a USP Type II apparatus at 50 or 100 rpm in about 1000 mL of from about 2% to about 16% (e.g., 2%, 4%, 6%, 8%, 10%, 12%, 14% or 16%) Triton X-100 solution in water at a specific temperature e.g., 20.0, 37.0 or 40.0° C. (±0.5). In a specific aspect, the unit dosage form release greater than 5%, 10%, 15%, 20%, 25%, 30%, 35%, 40%, 45%, or 50% at one hour. According to one aspect of this embodiment, the unit dosage form has a surfactant e.g., at least 1, 2, 3, 4, 5, 10, 15, 20, 30, 40, or 50 mg of a non-ionic or ionic surfactant. According to another aspect of this embodiment, the unit dosage form has one or more of (1) a lipophilic additive, (2) a diluent (3) a binder (4) a disintegrant, (5) a lubricant and (6) one or more other pharmaceutically acceptable excipients. According to one aspect of this embodiment, the unit dosage form has a lipophilic additive, binder, a diluent, a disintegrant or a combination thereof individually or together in an amount of e.g., at least 10, 20, 30, 40, 50, 100, 150, 200, 300, 400, or 500 mg (or within a range defined by any two of these values.) In one particular embodiment the oral dosage form of the current invention comprises a therapeutically effective amount of an ester of 17-hydroxyprogesterone, wherein, when measured using a USP Type-II dissolution apparatus in 900 mL of deionized water with 0.5% (w/v) of sodium lauryl sulfate at 50 RPM at 37° C., the oral dosage form releases at least 20 wt % of the dose of the ester of 17-hydroxyprogesterone after 60 minutes, In another particular embodiment, the dosage form releases at least about 40 wt % of the dose of the ester of 17-hydroxyprogesterone after 60 minutes. In another particular embodiment, the dosage form releases at least about 50 wt % of the dose of the ester of 17-hydroxyprogesterone after 60 minutes. In another particular embodiment, the dosage form releases at least about 70 wt % of the dose of the ester of 17-hydroxyprogesterone after 60 minutes. In a specific embodiment the ester is 17-hydroxyprogesterone caproate. In another embodiment, the dosage form is administered with food.

Following oral administration of the ester of 17-hydroxyprogesterone (e.g., 17-hydroxyprogesterone caproate) in the form of the composition or dosage form the present invention, its concentration in the serum, plasma or blood of the subject may be determined by analytical techniques based on radio-immunoassay (MA), high performance liquid chromatography-Mass Spectroscopy (HPLC-MS/MS) and the like. Accordingly, the plasma or blood levels for the ester may be different. It has to be understood that any relative comparisons of blood plasma levels of any compound should be made with the same assay methodology, or corrections must be made to adjust for discrepancy for assay specificity.

Accordingly, in one embodiment, the 17-hydroxyprogesterone caproate compositions or dosage forms of the present invention can provide a mean steady state 17-hydroxyprogesterone caproate mean $C_{max}$ from about 10 ng/mL to about 800 ng/mL, wherein the plasma 17-hydroxyprogesterone caproate is determined by HPLC-MS/MS method. In a particular embodiment, the compositions or dosage forms provides a mean steady state 17-hydroxyprogesterone caproate mean $C_{max}$ from about 10 ng/mL to about 400 ng/mL.

In further embodiment, the 17-hydroxyprogesterone caproate compositions or oral dosage forms of the present invention can provide a 17-hydroxyprogesterone caproate mean steady state $C_{min}$ of about 1 ng/mL or more. The plasma concentrations of the 17-hydroxyprogesterone caproate can be determined by HPLC-MS/MS method. In one embodiment, the compositions or oral dosage forms can provide a 17-hydroxyprogesterone caproate mean steady state $C_{min}$ greater than about 10 ng/mL. In another embodiment, the composition or oral dosage forms can provide a 17-hydroxyprogesterone caproate mean steady state $C_{min}$ greater than about 20 ng/mL, or greater than about 40 ng/ml, greater than about 60 ng/mL, or greater than about 80 ng/mL. In one specific embodiment, the composition or oral dosage form can provide a mean steady state $C_{min}$ of about 1 to about 60 ng/mL. In another specific embodiment, the composition or dosage form can provide a mean steady state $C_{min}$ of about 1 ng/mL to about 20 ng/mL.

In further embodiment, the 17-hydroxyprogesterone caproate compositions or oral dosage forms or method described herein can provide a 17-hydroxyprogesterone caproate mean steady state $C_{min}$ of greater than about 0.001, 0.01, 0.05, 0.1, 0.5, 1, 2, 3, 4, 5, 6, 7, 8, 9 or 10 ng/mL (or within a range defined by any two of these values). The plasma concentrations of the 17-hydroxyprogesterone caproate can be determined by HPLC-MS/MS method. In one aspect, the $C_{min}$ range occurs for less than 4 hours, 3, hours, 2 hours or 0.5 hours per day. In one aspect, the $C_{min}$ values in this paragraph are threshold values for which the patient does not have values lower than these values or ranges for more than 4 hours, 3, hours, 2 hours, 0.5 hours or 0.25 hours per day.

Accordingly, the oral dosage form of 17-hydroxyprogesterone caproate of the present invention can be an immediate release dosage form. In a separate embodiment, the oral dosage form of the 17-hydroxyprogesterone caproate of the present invention can be a controlled release dosage form. In another specific embodiment, dosage form can include 17-hydroxyprogesterone caproate in the form of both immediate release and controlled release fractions, preferably extended or delayed release.

Consequently, the controlled release 17-hydroxyprogesterone caproate compositions or dosage forms of the present invention can provide a fluctuation in the 17-hydroxyprogesterone caproate levels less than about 795 ng/mL, wherein the fluctuation is determined by the difference of the mean steady state $C_{max}$ and the mean steady state $C_{min}$ of 17-hydroxyprogesterone caproate in plasma or serum or blood, upon oral administration.

In another embodiment, 17-hydroxyprogesterone caproate compositions or dosage forms of the present invention can provide a fluctuation in the 17-hydroxyprogesterone caproate levels less than about 2000, 1500, 1000, 900, 800, 700, 600, 500, 400, 300, 200, 175, 150, 140, 130, 120, 110 or 100 ng/mL, wherein the fluctuation is determined by the difference of the mean steady state $C_{max}$ and the mean steady state $C_{min}$ of 17-hydroxyprogesterone caproate in plasma or serum or blood, upon oral administration.

In another embodiment, 17-hydroxyprogesterone caproate compositions or dosage forms of the present invention can provide a fluctuation in the 17-hydroxyprogesterone caproate levels greater than about 1, 10, 15, 25, 50, 75, 100, 200, 300 or 400 ng/mL, wherein the fluctuation is determined by the difference of the mean steady state $C_{max}$ and the mean steady state $C_{min}$ of 17-hydroxyprogesterone caproate in plasma or serum or blood, upon oral administration. In an aspect of the fluctuation embodiments, the fluctuation falls within a range defined by any two of the values in the greater than and less than embodiments.

In a another particular aspect, the oral pharmaceutical compositions and/or dosage forms of 17-hydroxyprogesterone caproate of the current invention can be used for the treatment of one or more of the conditions selected from the group consisting of habitual abortion, recurrent abortion, threatened abortion, post-partum after pains, endometrial cancer, management of primary and secondary amenorrhea, infertility due to corpus *luteum* insufficiency, deficiency of progestogen, cervical insufficiency, cervical incompetency, and abnormal uterine bleeding. In a further embodiment, the oral pharmaceutical compositions and/or dosage forms of 17-hydroxyprogesterone caproate of the current invention can be used for testing endogenous estrogen production, and for the production of secretory endometrium and desquamation.

In another embodiment, the oral pharmaceutical compositions and/or dosage forms of 17-hydroxyprogesterone caproate of the current invention can be used along with omega-3 fatty acid supplementation to treat symptomatic preterm labor patients. In a particular embodiment, the current invention compositions and/or dosage forms may include at least one omega fatty acid. In another particular embodiment, the current invention compositions and/or dosage form may include omega-3, omega-6 or omega-9 fatty acid or mixtures thereof.

In one embodiment, a method is provided for treating a pregnant female based on gestational age. The method involves treating a pregnant female with a pharmaceutically composition formulated for oral administration comprising 17HPC and a pharmaceutically acceptable carrier with an initial gestational age daily dose of 17HPC. The initial gestational age daily dose of 17HPC is selected or determined based on gestational age. For example, initiation of treatment of a pregnant female with a gestational age of 20 weeks involves a daily dose of 17HPC appropriate for this gestational age. Initiation of treatment of a pregnant female with a gestational age of 26 weeks involves a daily dose appropriate for this gestational age. The initial gestational age daily dose for 20 weeks gestational age and 26 weeks gestational age can be the same or differ (a non-limiting example is that a 20 week initial gestational age daily dose can be e.g., 550 mg 17HPC per day orally whereas a 20 week initial gestational age daily dose can be e.g., 750 mg 17 HPC per day orally). Gestational age can be determined by any appropriate method including directly calculating the days since the beginning of the last menstrual period, early obstetric ultrasound, and the like. A pregnant female being treated with an initial gestational age daily dose of 17HPC can be maintained on the same daily dose of 17HPC throughout the pregnancy or have a daily dose alteration based on a later gestational age. For example, the initial gestational age daily dose can be between 10 mg to 1500 mg per day orally and after 1 day, 2 days, 3, days, 5 days, 7 days, 10 days, 14 days, 18 days, 21 days or more on the initial gestational age daily dose, the dose can be adjusted within plus/minus 5 mg to 1495 mg per day orally which is a referred to as a second gestational age daily dose. Likewise, the second gestational age daily dose can be adjusted after 1 day, 2 days, 3, days, 5 days, 7 days, 10 days, 14 days, 18 days, 21 days or more on the second gestational age daily dose, the dose can be adjusted within plus/minus 5 mg to 1495 mg per day orally of the second gestational age daily dose—this new daily dose is referred to as the third gestational age daily dose. Alternatively, the gestational age treatment can be based on IM injection. For example, 17HPC is formulated as an IM injection and the amount of 17HPC administered via the IM route is based on the gestational age. For example, the oil can be castor oil or another suitable vegetable oil (e.g., corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil)). The formulation can include one or more of benzyl benzoate, benzyl alcohol. The formulation can include a surfactant (e.g., non-ionic surfactant) or more or more other optional additives. The initial gestational dose and second gestational age doses of 17 HPC are within the range of about 50 mg to 1000 mg per week (or e.g., 100 mg to 2000 mg every two weeks or 200 mg to 4000 mg per month). The dose is then adjusted based on gestational are as general described above although the dose changes correlate to about 25 mg or less, 50 mg or less, 100 mg or less or 200 mg or less per week of IM 17HPC.

In one embodiment, a method of administering 17HPC to a female is provided. The method involves administering to or treating a female with a pharmaceutical composition formulated for oral administration comprising 17HPC and a pharmaceutically acceptable carrier with an initial daily dose of 17HPC. Typically, the initial daily dose of 17HPC is in the range of 10 mg to 1500 mg per day. After a period of time e.g., 1 day, 2 days, 3, days, 5 days, 7 days, 10 days, 14 days, 18 days, 21 days or more, a biomarker from the female being treated is measured or the level of the biomarker is determined. If the biomarker is within a maintenance target range, then the female continues to receive the same daily dose. If the biomarker is within an up-titration target range, then the female is administered a second daily dose that is greater than the initial daily dose. If the biomarker is within a down-titration target range, then the female is administered a second daily dose that is less than the initial daily dose. Typically, the daily dose changes between the initial and second daily doses are within plus/minus 10%, 20%, 30%, 40%, 50%, 60%, 70%, 80%, or 90% of each other. Alternatively, an up-titration or down titration can be a change from the initial daily dose of about 10-20 mg, 20-30 mg, 30-40 mg, 40-50 mg, 50-60 mg, 60-70 mg, 70-80 mg 80-90 mg, 90-100 mg, 100-125 mg, 125-150 mg, 150-175 mg or 175-200 mg (or 200-225 mg, 225-250 mg, 250-300 mg, 300-325 mg, 325-350 mg, 350-400 mg, 400-425 mg, 425-450 mg, or 450-500 mg). The biomarker used to determine titration can be any appropriate biomarker. For example, the biomarker can be an efficacy biomarker, a safety biomarker or a combination thereof. The biomarker can be 17HPC or a metabolite thereof. 17HPC or a metabolite thereof can be serum 17HPC or metabolite thereof, urinary 17HPC or a metabolite thereof, salivary 17HPC or a metabolite thereof. The biomarker can be a steroid e.g., progesterone or a metabolite thereof (serum, salivary, urinary). The biomarker can be any biomarker specified in this application or otherwise useful for determining titrations. In one specific example, the titration biomarker is serum 17HPC (a pharmacokinetic parameter). For example, if the serum 17HPC (e.g., $C_{avg}$, $C_{min}$, $C_{max}$ or any other pharmacokinetic parameter and particularly described herein) is below a minimum target threshold, the daily dose of 17HPC daily dose can be increased, if the serum 17HPC is above a maximum target threshold, then the 17HPC daily dose can be decreased, or if the serum 17HPC is within a target range that is deemed sufficient, then the daily dose can be maintained. In one aspect, the target is can provide a 17-hydroxyprogesterone caproate $C_{avg\text{-}24h}$ greater than about 0.05, 0.1, 0.5, 0.7, 1.0, 1.5, 2.0, 3.0, 5.0, 10.0, 15.0, 20.0, 25.0, 30.0, 35.0, 40.0, 45.0, 50.0 60.0, 75.0 or 100 ng/mL (or alternatively less than any of these values or alternatively within a range defined by any two of these values). In one aspect, the said 17-hydroxyprogesterone caproate $C_{avg\text{-}24h}$ is determined by an HPLC-MS/MS method of analysis of the plasma, serum or blood samples collected following the oral administration. In one aspect, the oral pharmaceutical composition comprises 17-hydroxyprogesterone caproate and a pharmaceutically acceptable carrier, wherein, when measured using a USP Type-II dissolution apparatus in 900 mL of simulated intestinal fluid having 0.5% w/w sodium lauryl sulfate at 50 RPM at 37° C., at least 20% of the 17-hydroxyprogesterone caproate is released from the oral composition at 60 minutes. In one aspect, the oral pharmaceutical composition comprises: 17-hydroxyprogesterone caproate, and a pharmaceutically acceptable carrier including at least a hydrophilic surfactant. In one aspect, the oral pharmaceutical composition, comprises: 17-hydroxyprogesterone caproate having a mean particulate diameter of about 50 micron or less, and a pharmaceutically acceptable carrier including at least a hydrophilic surfactant. In one aspect, the oral pharmaceutical composition comprises: 17-hydroxyprogesterone caproate having a mean particulate diameter of about 50 micron or less, and a pharmaceutically acceptable carrier including at least a hydrophilic surfactant wherein, when measured using a USP Type-II dissolution apparatus in 900 mL of simulated intestinal fluid having 0.5% w/w sodium lauryl sulfate at 50 RPM at 37° C., at least 20% of the 17-hydroxyprogesterone caproate is released from the oral composition at 60 minutes. In one aspect, the oral pharmaceutical composition comprises: 17-hydroxyprogesterone caproate having a mean particulate diameter of about 50 micron or less, and a pharmaceutically acceptable carrier including at least a hydrophilic surfactant; wherein the amount of the 17-hydroxyprogesterone caproate is from about 5% to about 80% w/w of the total composition; and wherein, when measured using a USP Type-II dissolution apparatus in 900 mL of simulated intestinal fluid having 0.5% w/w sodium lauryl sulfate at 50 RPM at 37° C., at least 20% of the 17-hydroxyprogesterone caproate is released from the oral composition at 60 minutes. In one aspect, the oral pharmaceutical composition comprises a hydrophilic surfactant, which is an ionic hydrophilic surfactant. In one aspect, the oral pharmaceutical composition comprises a hydrophilic surfactant, which is a non-ionic hydrophilic surfactant. In one aspect, the oral pharmaceutical composition comprises a hydrophilic surfactant, which is a poloxamer, a polyethylene glycol sorbitan fatty acid ester, a sorbitan fatty acid ester, a polyethylene glycol glycerol fatty acid ester or a combination thereof. In one aspect, the oral pharmaceutical composition comprises a hydrophilic surfactant, which is sodium lauryl sulfate, sodium dioctyl sulfosuccinate, a lecithin, a bile salt or a combination thereof. In one aspect, the oral pharmaceutical composition further comprises polyvinylpyrrolidone, croscarmellose, microcrystalline cellulose, magnesium stearate, silicon dioxide, stearic acid, mannitol, a polyvinyl alcohol copolymer, a polyvinylpyrrolidone copolymer, a polyethylene glycol copolymer, a methacrylic acid copolymer, or a combination thereof. In one aspect, the oral pharmaceutical composition is formulated as a powder, granulate, particulate, bead, pellet, sprinkle, suspension, solution, tablet, capsule, or a combination thereof. In one aspect, the oral pharmaceutical composition is formulated as a capsule. In one aspect, the oral pharmaceutical composition is formulated as a tablet. In one aspect, the oral pharmaceutical composition comprises an amount of 17-hydroxyprogesterone caproate equivalent to from about 20 mg to about 400 mg of 17-hydroxyprogesterone. In one aspect, the oral pharmaceutical composition has from about 20 mg to about 800 mg 17-hydroxyprogesterone caproate. In one aspect, the oral pharmaceutical composition has from about 10 mg to about 300 mg 17-hydroxyprogesterone caproate. As shown in Example 58, There was a good correlation of $C_{max}$ to $C_{avg}$ and $C_{avg}$ to pre-dose C value which enables single point titration (e.g., based on serum or plasma 17HPC levels at a single time point with 0-12 hours after single dose administration at steady state (e.g., at 0.5, 1, 1.5, 2, 2.5, 3, 3.5, 4, 4.5, 5, 5.5, 6, 6.5, 7, 7.5, 8, 8.5, 9, 9.5, 10, 10.5, 11, or 11.5 hours after single dose administration (or within a range defined by any two of these values, or within a range of within 0.5 h or 1 h of any one of these values))). For example, a pregnant female at risk for preterm birth is administered orally, a pharmaceutical composition (e.g., as described herein), in an initial dosing regimen, until steady state is achieved (e.g., 5 or more days, 6 or more days, 7 or more days). The initial dosing regimen (or alternatively after titration can be) can be e.g., 400 mg per day, 450 mg per day, 500 mg per day, 550 mg per day, 600 mg per day, 650 mg per day, 700 mg per day, 750 mg per day, 800 mg per day, 850 mg per day, 900 mg per day, 950 mg per day, 1000 mg per day, 1150 mg per day, 1200 mg per day, 1250 mg per day, 1300 mg per day, 1350 mg per day, 1400 mg per day, 1450 mg per day, 1500 mg per day, 1550 mg per day, 1600 mg per day, 1650 mg per day, 1700 mg per day, 1750 mg per day, 1800 mg per day, 1850 mg per day, 1900 mg per day, 1950 mg per day or 2000 mg per day (or within a range defined by any two of these values, or within a range of within 50 mg or 100 mg of any one of these values) e.g., on a once, twice, thrice, or four times a day dosing regime. After single dose administration at steady state, the plasma or serum 17HPC in the subject is determined and if the levels are too low, the daily dose is increased, if the levels are too high, the daily dose is increased or if they levels are appropriate, the daily dose is maintained. The pharmaceutical composition can delivery the daily dose in e.g., 1, 2, 3, 4, 5, 6, 7, 8, 9, 10, 11, 12, 13, 14, 15 or 16 unit dosage forms per day.

In one embodiment, the pharmaceutical compositions containing 17HPC are for use in conditions associated with preterm labor. Thus, in some aspects, a method for treating preterm labor or a condition associated with preterm labor is provided. The method involves orally administering a pharmaceutical composition comprising 17HPC and a pharmaceutically acceptable carrier to a pregnant female experiencing preterm labor, at risk for preterm labor or after preterm labor. The method and oral pharmaceutical composition can reduce the risk of preterm labor, reduce the risk of preterm birth as a result of preterm labor, provide tocolytic effect, improve tocolysis, provide maintenance tocolysis, reduce preterm birth, reduce the risk of miscarriage, improve neonatal outcome, prolong gestation, improve postnatal outcome, improve maternal outcome, improve Bayley Scales of Infant Development Scores (including one or more of motor (fine, gross or both), language (receptive, expressive or both), and cognitive development), improve scores on Social-Emotional Adaptive Behavior Questionnaire, or a combination thereof. The pharmaceutical composition and method of this embodiment can improve neonatal outcomes including birth weight gestational age or both. The pharmaceutical composition and method of this embodiment can improve maternal, infant and child outcomes as described elsewhere herein.

Preterm labor refers to regular contractions of the uterus that result in changes in the cervix that occur before 37 weeks of pregnancy. Changes in the cervix include effacement (e.g., the cervix thins out) and dilation (e.g., the cervix opens so that the fetus can enter the birth canal). In one aspect, preterm labor is diagnosed by transvaginal ultrasound, fetal fibronectin in vaginal discharge or both. Accordingly, in one aspect, a pregnant female experiencing preterm labor is administered an oral pharmaceutical composition having 17HPC and a pharmaceutically acceptable carrier. In another aspect, a method for improving one or more of maternal, infant and child outcomes is provided. The method involves administering to a female that recently experienced preterm labor e.g., within 3 weeks, 2 weeks, 1 week, 6 days, 5 days, 4 days, 3 days, 2 days, or 1 day an oral pharmaceutical composition having 17 HPC and a pharmaceutically acceptable carrier. The pregnant female can have had the preterm labor stop, subside or lessen without pharmaceutical intervention or alternatively the preterm labor was treated medically with a pharmaceutical intervention. In one aspect, the pharmaceutical intervention is magnesium sulfate or a tocolytic. The daily dose of 17HPC and per unit dosage are as described herein. In a specific aspect, the daily dose of 17HPC ranges from about 550 mg to about 1600 mg. In another specific aspect, the unit dosage forms comprise from about 250 mg to about 800 mg of 17HPC.

In one embodiment, a combination therapy is provided, comprising oral 17HPC and a second agent. The second agent can be a pharmaceutical agent, a vitamin, a mineral, supplement, etc.

In one aspect, a combination therapy is provided, comprising oral 17HPC and a compound chosen from a progestogen, a corticosteroid, a tocolytic, an antibiotic, a vitamin D compound or a combination thereof. The combination therapy, in some aspects, involves a co-formulation of oral 17HPC and a compound chosen from a progestogen, a corticosteroid, a tocolytic, an antibiotic, a vitamin D compound or a combination thereof. According to this aspect, the co-formulation is orally administered to a subject in need thereof. For example, a co-formulation of (1) 17HPC, (2) one or more of a progestogen, a corticosteroid, a tocolytic, an antibiotic, a vitamin D compound and (3) a pharmaceutically acceptable carrier is administered to a pregnant female. The combination therapy, in some aspects, involves a co-administration of oral 17HPC and a compound chosen from a progestogen, a corticosteroid, a tocolytic, an antibiotic, a vitamin D compound or a combination thereof. Co-administration refers to oral administration of 17HPC and enteral, parenteral or topical administration of one or more of a progestogen, a corticosteroid, a tocolytic, an antibiotic and a vitamin D compound.

In one aspect, a combination therapy is provided, comprising oral 17HPC and a compound chosen from an antenatal corticosteroid, beta-adrenergic receptor agonist, a calcium channel blocker, magnesium sulfate, an NSAID, an oxytocin antagonist or a combination thereof. The pharmaceutical compositions and methods of this embodiment can improve maternal, infant and child outcomes as described elsewhere herein.

The pharmaceutical compositions comprising 17HPC and a pharmaceutically acceptable carrier can be co-formulated or co-administered with prenatal vitamins or supplements and the like. For example, the pharmaceutical compositions described herein can be co-administered or co-formulated with A, B3, B6, C, D, folic acid, calcium, iron, magnesium, manganese, phosphorus, potassium, sodium, zinc, omega-3, eicosapentaenoic acid (EPA), docosahexaenoic (DHA) or a combination thereof. For example one or more of, 400 micrograms (mcg) of folic acid, 400 IU of vitamin D, 200 to 300 mg of calcium, 65-75 mg of vitamin C, 2-4 mg of thiamine, 1-3 mg of riboflavin, 14-25 mg of niacin, 4-8 mcg of vitamin B12, 8-12 mg of vitamin E, 13-17 mg of zinc, 15-19 mg of iron, 140-160 micrograms of iodine can be co-administered with the pharmaceutical compositions comprising 17HPC and a pharmaceutically acceptable carrier described herein. Co-administration does not necessarily mean that the compositions are administered at the same time. For example, the prenatal vitamins can be administered once-a-day (or more) and a different time of day than the 17HPC containing compositions (which could be administered e.g., two time or three times daily).

In one embodiment, compositions and methods for treating a pregnant female is provided. According to this embodiment, a therapy comprising vitamin D and oral 17HPC is provided. In one aspect, the therapy comprises administration of oral 17HPC and oral vitamin D to a pregnant female. The daily dose of 17HPC and per unit dosage are as described herein. In a specific aspect, the daily dose of 17HPC ranges from about 550 mg to about 1600 mg. In another specific aspect, the unit dosage forms comprise from about 250 mg to about 800 mg of 17HPC. In one aspect, the daily dose of vitamin D is 200 IU per day or more. In another aspect, the daily dose of vitamin D is 400 IU per day or more. In another aspect, the daily dose of vitamin D is 600 IU per day or more. In another aspect, the daily dose of vitamin D is 800 IU per day or more. In another aspect, the daily dose of vitamin D is 1000 IU per day or more. In another aspect, the daily dose of vitamin D is 1500 IU per day or more. In another aspect, the daily dose of vitamin D is 2000 IU per day or more. In another aspect, the daily dose of vitamin D is 3000 IU per day or more. In another aspect, the daily dose of vitamin D is 4000 IU per day or more. In another aspect, the daily dose of vitamin D is 5000 IU per day or more. In another aspect, the daily dose of vitamin D is 4000 IU per day or more. In another aspect, the daily dose of vitamin D is 6000 IU per day or more. In another aspect, the daily dose of vitamin D is from 450 to 8000 IU per day or more. In another aspect, the daily dose of vitamin D is from 450 to 3000 IU per day or more. In another aspect, the daily dose of vitamin D is from 450 to 2000 IU per day or more. In another aspect, the daily dose of vitamin D is from 450 to 2000 IU per day or more. In one aspect, the daily dose of vitamin D is based at least in part on first, second, or third trimester serum vitamin D levels of the pregnant female. For example, in one aspect, the dose of vitamin D is chosen such that the level of serum vitamin D falls within the range of about 50 to about 75 nmol/L. In another aspect, the dose of vitamin D is chosen such that the level of serum vitamin D is greater than about 50 nmol/L. In another aspect, the dose of vitamin D is chosen such that the level of serum vitamin D falls is greater than about 75 nmol/L. In another aspect, the dose of vitamin D is chosen such that the level of serum vitamin D is greater than about 100 nmol/L. In another aspect, the dose of vitamin D is chosen such that the level of serum vitamin D is greater than about 125 nmol/L. In another aspect, the dose of vitamin D is chosen such that the level of serum vitamin D is greater than about 150 nmol/L. In another aspect, the dose of vitamin D is chosen such that the level of serum vitamin D is greater than about 175 nmol/L. In one aspect, the daily dose of vitamin D is chosen such that the level of serum vitamin D falls within a range of about 50 nmol/L to about 200 nmol/L. In another aspect, the dose of vitamin D is chosen such that the level of serum vitamin D is greater than about 500, 400, 300 or 200 nmol/L. In one aspect, the serum level of the pregnant female is titrated into a selected range or value. For example, the pregnant female is administered a dose of vitamin D, e.g., 200 IU per day and it is determined that this daily dose has not provided her with sufficient vitamin D. The dose can then be increased, e.g., by 50 IU or more, 100 IU or more, 200 IU or more, 300 IU or more, until the desired target vitamin D level is reached. Alternatively, the vitamin D daily dose can be down-titrated into the target range in a similar manner. In one aspect, the serum vitamin D is 25-hydroxyvitamin D (the target serum vitamin D levels or ranges are for 25-hydroxyvitamin D). In one aspect, the pharmaceutical composition that is administered comprises cholecalciferol or ergocalciferol. In one aspect, the pharmaceutical composition that is administered comprises alfacalcidol, calcifediol, calcitriol, dihydrotachysterol or combination thereof. In one aspect, the pharmaceutical composition that is administered comprises cholecalciferol, alfacalcidol, calcifediol, calcitriol, dihydrotachysterol or a combination thereof and 17HPC. In one aspect, the amount of vitamin D administered is in addition to that being provided by prenatal vitamins or supplements to the pregnant female. In one aspect, the pharmaceutical composition that is administered comprises at least 50 IU cholecalciferol and at least 50 mg 17HPC. In one aspect, the pharmaceutical composition that is administered comprises 50 IU to 400 IU cholecalciferol and 100 mg to 450 mg 17HPC. In one aspect, the combination composition is formulated for parenteral administration. In another aspect, the combination composition is formulated for oral administration. In one aspect, the daily comprises at least 200 IU cholecalciferol and at least 200 mg 17HPC. In one aspect, the daily dose comprises 200 IU to 4000 IU cholecalciferol and 400 mg to 1600 mg 17HPC. In one aspect, the daily dose comprises 200 IU to 4000 IU cholecalciferol and 550 mg to 1600 mg 17HPC. The method and composition according to this embodiment provide one or more of an improvement in maternal, infant and child outcomes with respect to a pregnant female. In one aspect, pregnant female is at risk for preterm birth due to previous low birth weight or preterm delivery, multiple 2nd trimester spontaneous abortion, exposure to tobacco smoke or tobacco smoke residue, use of smokeless tobacco, substance use or abuse or dependence, alcohol use or abuse or dependence, stress, anxiety, depression, short stature, poor nutritional status, insufficient weight gain during pregnancy, low prepregnancy weight/low body mass index, advanced maternal age, low socio-economic status, prior first trimester induced abortion, familial and intergenerational factors, history of infertility, nulliparity, placental abnormalities, cervical and uterine anomalies, gestational bleeding, intrauterine growth restriction, in utero diethylstilbestrol exposure, multiple gestations, infant sex (e.g., fetal male), urogenital infections, preeclampsia or a combination thereof.

In one embodiment, a therapy is provided comprising intramuscular injection of vitamin D and 17HPC to a pregnant female. According to one aspect of this embodiment, a pregnant female is administered from 100 mg/mL to 500 mg/mL of 17HPC per week and from 10,000 IU to 300000 IU cholecalciferol per week. According to one aspect of this embodiment, a pregnant female is administered from 100 mg/mL to 500 mg/mL of 17HPC per week and from 10,000 IU to 100000 IU cholecalciferol per week. According to one aspect of this embodiment, a pregnant female is administered from 100 mg to 500 mg of 17HPC per week and from 10,000 IU to 50000 IU cholecalciferol per week. In one aspect, the vitamin D and 17HPC are coformulated for IM injection. In another aspect, the vitamin D and 17HPC are formulated separately. The values described in this embodiment can be for one week, two weeks, three weeks or more. For example, a two week dose can be provides which would be twice the dose of the one week dose. According to one aspect of this embodiment, a pregnant female is administered from a dose of about 200 mg to 300 mg (e.g., 1 mL of 250 mg/mL 17 HPC) of 17HPC per week and a dose of from 10,000 IU to 50000 IU cholecalciferol per week. The 17HPC, cholecalciferol, or both can be formulated for IM injection in a vehicle having an oil suitable for IM injection and optionally a solubilizer. For example, the oil can be castor oil or another suitable vegetable oil (e.g., corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil)). The formulation can include one or more of benzyl benzoate, benzyl alcohol. The formulation can include a surfactant (e.g., non-ionic surfactant) or more or more other optional additives.

Examples of beta-adrenergic receptor agonist include, but are not limited to, fenoterol, terbutaline, salbutamol, and nifedipine. Examples of NSAIDs include, but are not limited to, indomethacin, ketorolac and sulindac. An example of a calcium channel blocker includes, but is not limited to, nifedipine. An example of an oxytocin antagonist includes, but is not limited to, atosiban. Examples of antenatal corticosteroids include, but are not limited to, betamethasone and dexamethasone. Examples of antibiotics include, but are not limited to ampicillin and penicillin. Examples of vitamin D compounds include, but are not limited to, cholecalciferol and ergocalciferol. Examples of progestogens include, but are not limited to, progesterone and dydrogesterone.

Nifedipine can be administered at e.g., an initial oral dose of 20 mg followed by 10-20 mg three to four times daily, adjusted according to uterine activity for up to 48 hours. Total doses above 60 mg appear to be associated with increased adverse events. Atosiban can be administered e.g., as an initial bolus dose of 6.75 mg over 1 minute, followed by an infusion of 18 mg/hour for 3 hours, then 6 mg/hour for up to 45 hours (to a maximum of 330 mg).

In one embodiment, a method of treatment is provided that involves orally administering to a pregnant female a pharmaceutical composition having 17HPC and a pharmaceutically acceptable carrier where the preganant female is at risk for preterm birth due to previous low birth weight or preterm delivery, multiple 2nd trimester spontaneous abortion, exposure to tobacco smoke or tobacco smoke residue, use of smokeless tobacco, substance use or abuse or dependence, alcohol use or abuse or dependence, stress, anxiety, depression, short stature, poor nutritional status, insufficient weight gain during pregnancy, low prepregnancy weight/ low body mass index, advanced maternal age, low socio-economic status, prior first trimester induced abortion, familial and intergenerational factors, history of infertility, nulliparity, placental abnormalities, cervical and uterine anomalies, gestational bleeding, intrauterine growth restriction, in utero diethylstilbestrol exposure, multiple gestations, infant sex, urogenital infections, preeclampsia or a combination thereof.

The ester of 17-hydroxyprogesterone (e.g., 17-hydroxyprogesterone caproate) is provided herein which is crystalline. The crystalline ester of 17-hydroxyprogesterone (e.g., 17-hydroxyprogesterone caproate) can be a particular crystal form, a solvate of a crystal form, a polymorph, a pseudopolymorph, a pharmaceutically acceptable solvate, or a hydrate. In a specific aspect, the crystalline ester of 17-hydroxyprogesterone (e.g., 17-hydroxyprogesterone caproate) is a crystal form substantially free of other crystal forms of ester of 17-hydroxyprogesterone (e.g., 17-hydroxyprogesterone caproate). In another specific aspect, the crystalline ester of 17-hydroxyprogesterone (e.g., 17-hydroxyprogesterone caproate) is substantially free of amorphous ester of 17-hydroxyprogesterone (e.g., 17-hydroxyprogesterone caproate).

In a related aspect, amorphous ester of 17-hydroxyprogesterone (e.g., 17-hydroxyprogesterone caproate) is provided which is substantially free of crystalline ester of 17-hydroxyprogesterone (e.g., 17-hydroxyprogesterone caproate).

Ester of 17-hydroxyprogesterone (e.g., 17-hydroxyprogesterone caproate) is provided herein having a particular size characteristic. For example provided herein is ester of 17-hydroxyprogesterone (e.g., 17-hydroxyprogesterone caproate) which is not-milled or is milled, micronized or nanosized. In specific aspects, ester of 17-hydroxyprogesterone (e.g., 17-hydroxyprogesterone caproate) is provided wherein the particle size is less than 200 nm ("nanometer"), from 200 to 500 nm, from 500 to 1000 nm, from 1 to 50 µm ("micrometer"), from 50 to 250 µm, from 250 to 500 µm, from 500 to 1000 µm, or greater than 1000 µm. In another aspect, the ester of 17-hydroxyprogesterone (e.g., 17-hydroxyprogesterone caproate) having a $d_{50}$ of greater than 1000 µm, from 355 to 1000 µm, from 180 to 355 µm, from 125 to 180 µm, 90 to 125 µm 1 to 90 µm, or less than 1 µm. In one specific aspect, the mean particle size of ester of 17-hydroxyprogesterone (e.g., 17-hydroxyprogesterone caproate) is from 1 to 40 µm, from 1 to 30 µm, or from 1 to 25 µm. In another related aspect, the ester of 17-hydroxyprogesterone (e.g., 17-hydroxyprogesterone caproate has a $D_{10}$, $D_{50}$, or $D_{90}$ that is less than 200 nm, from 200 to 500 nm, from 500 to 1000 nm, from 1 to 50 µm, from 50 to 250 µm, from 250 to 500 µm, from 500 to 1000 µm, or greater than 1000 µm. In one particular aspect, the ester of 17-hydroxyprogesterone (e.g., 17-hydroxyprogesterone caproate) having a particular size or size characteristics is crystalline ester of 17-hydroxyprogesterone (e.g. 17-hydroxyprogesterone caproate). In another particular aspect, the ester of 17-hydroxyprogesterone (e.g., 17-hydroxyprogesterone caproate) having a particular size or size characteristics is a crystal form of the ester of 17-hydroxyprogesterone (e.g. 17-hydroxyprogesterone caproate) substantially free of other crystal forms of the ester of 17-hydroxyprogesterone (e.g., 17-hydroxyprogesterone caproate). In yet another, the ester of 17-hydroxyprogesterone (e.g., 17-hydroxyprogesterone caproate) having a particular size or size characteristics is amorphous ester of 17-hydroxyprogesterone (e.g., 17-hydroxyprogesterone caproate). In yet another, the ester of 17-hydroxyprogesterone (e.g., 17-hydroxyprogesterone caproate) having a particular size or size characteristics is amorphous ester of 17-hydroxyprogesterone (e.g., 17-hydroxyprogesterone caproate) substantially free of crystalline ester of 17-hydroxyprogesterone (e.g., 17-hydroxyprogesterone caproate).

Pharmaceutical compositions are provided herein having or prepared from ester of 17-hydroxyprogesterone (e.g., 17-hydroxyprogesterone caproate) as described in the paragraphs above. For example, the pharmaceutical composition is prepared from or has ester of 17-hydroxyprogesterone (e.g., 17-hydroxyprogesterone caproate) and one or more pharmaceutically acceptable excipients or carriers. The pharmaceutical composition described herein can comprise or be prepared from crystalline ester of 17-hydroxyprogesterone (e.g., 17-hydroxyprogesterone caproate), amorphous ester of 17-hydroxyprogesterone (e.g., 17-hydroxyprogesterone caproate), or a combination thereof. The pharmaceutical composition comprises or is prepared from a particular crystal form, a solvate of a crystal form, a polymorph, a pseudopolymorph, a pharmaceutically acceptable solvate, or a hydrate of crystalline ester of 17-hydroxyprogesterone (e.g., 17-hydroxyprogesterone caproate). Alternatively, the pharmaceutical composition is prepared from or comprises amorphous ester of 17-hydroxyprogesterone (e.g., 17-hydroxyprogesterone caproate). In some aspects, the pharmaceutical composition comprises or is prepared ester of 17-hydroxyprogesterone (e.g. 17-hydroxyprogesterone caproate) where the ester of 17-hydroxyprogesterone (e.g., 17-hydroxyprogesterone caproate) is not-milled or is milled, micronized or nanosized. Is specific aspects, the pharmaceutical composition comprises or is prepared from an ester of 17-hydroxyprogesterone (e.g., 17-hydroxyprogesterone caproate) wherein the mean particle size of the API is less than 200 nm, from 200 to 500 nm, from 500 to 1000 nm, from 1 to 50 µm, from 50 µm to 250 µm, from 250 µm to 500 µm, from 500 µm to 1000 µm, or greater than 1000 µm. In one specific aspect, the mean particle size of ester of 17-hydroxyprogesterone (e.g., 17-hydroxyprogesterone caproate) is from 1 to 40 µm, from 1 to 30 µm, from 1 to 25 µm, from 1 to 20 µm, from 1 to 15 µm, or from 1 to 10 µm. In another aspect, the pharmaceutical composition comprises or is prepared from an ester of 17-hydroxyprogesterone (e.g., 17-hydroxyprogesterone caproate) having a $d_{50}$ of greater than 1000 µm, from 355 to 1000 µm, from 180 to 355 µm, from 125 to 180 µm, from 90 to 125 µm, from 1 to 90 µm, from 1 to 40 µm, from 1 to 30 µm, or from 1 to 25 µm, or less than 1 µm. In another related aspect, the pharmaceutical composition comprises or is prepared from ester of 17-hydroxyprogesterone (e.g., 17-hydroxyprogesterone caproate) having a $D_{10}$, $D_{50}$, or $D_{90}$ that is less than 200 nm, from 200 to 500 nm, from 500 to 1000 nm, from 1 to 50 µm, from 50 to 250 µm, from 250 to 500 µm, from 500 to 1000 µm, or greater than 1000 µm. In some specific aspects, the pharmaceutical composition of this paragraph is formulated for topical, enteral or parenteral administration. In some aspects, the pharmaceutical composition of this paragraph is formulated for buccal, sublingual, or sublabial administration. In some specific aspects, the pharmaceutical composition of this paragraph is formulated for nasal, rectal or vaginal administration. In some specific aspects, the pharmaceutical composition of this paragraph is formulated for intravenous, subcutaneous, intramuscular, intradermal, intraspinal, intrathecal, or intra-arterial administration. In some specific aspects, the pharmaceutical composition of this paragraph is formulated as a sprinkle liquid, solution, suspension, dispersion, solid, semi-solid, a gel, a lotion, paste, foam, spray, suspension, dispersion, syrup, or ointment. In some specific aspects, the pharmaceutical composition of this paragraph is formulated as a tincture, patch, injectable, or oral dosage form. In some aspects, the pharmaceutical composition of this paragraph comprises solubilized or partially solubilized ester of 17-hydroxyprogesterone (e.g. 17-hydroxyprogesterone caproate). In one aspect, the pharmaceutical composition or unit dosage forms is suitable for oral administration (e.g., capsule or tablet).

D values like D10, D50 or D90 refer the size of particles e.g., a D10 of 5 micron refers to 10% of the particles having a size of 5 micron or less; a D90 of 17 micron refers to 90% of the particles having a particle size of less than 17 micron.

Solid state API, e.g., solid state ester of 17-hydroxyprogesterone (e.g. 17-hydroxyprogesterone caproate) described herein, can exist in different crystalline forms as well as in non-crystalline forms. A non-crystalline solid API is referred to herein as an "amorphous form," which is a disordered arrangement of API molecules. Different crystalline forms of the API, e.g., of a specific ester of 17-hydroxyprogesterone (e.g., 17-hydroxyprogesterone caproate), arise from different packing of the ester of 17-hydroxyprogesterone (e.g., 17-hydroxyprogesterone caproate) molecules in the solid state, resulting in different crystal symmetries and/or unit cell parameters. Crystalline forms are identified or characterized by any suitable methods e.g., x-ray diffraction (see, e.g., Remington's Pharmaceutical Sciences, 18th ed., Mack Publishing, Easton Pa., p 173 (1990); The United States Pharmacopeia, 23rd ed., pp. 1843-1844 (1995)). Such different crystalline forms are referred to herein as "polymorphic forms" or "non-solvated forms," which means that they are essentially free of residual solvents e.g., organic solvents. If the substances incorporate stoichiometric or non-stoichiometric amounts of water ("hydrate" as used herein), or any other solvent ("solvate" as used herein), in the crystal structure, these are referred to herein as a "pseudopolymorphic form."

The term "amorphous form" as used herein in connection with ester of 17-hydroxyprogesterone (e.g., 17-hydroxyprogesterone caproate) that is a non-crystalline solid (i.e., not in a crystalline form), which is a disordered arrangements of ester of 17-hydroxyprogesterone (e.g., 17-hydroxyprogesterone caproate) molecules. Typically, amorphous ester of 17-hydroxyprogesterone (e.g., 17-hydroxyprogesterone caproate) has no long-range periodic atomic structure as determined by X-ray powder diffraction (XRPD or XRD). The XRPD pattern of amorphous ester of 17-hydroxyprogesterone (e.g., 17-hydroxyprogesterone caproate) appears as a halo with no distinctive peaks. Amorphous material for some compounds can be obtained by a number of methods known in the art, including, but not limited to, heating, melt cooling, rapid melt cooling, solvent evaporation, rapid solvent evaporation, desolvation, sublimation, grinding, cryogrinding or freeze-drying.

The term "crystal" as used herein refers to a solid structure, typically formed by a solidification of an API, that generally has a regular atomic structure (characteristic shapes and cleavage planes formed by the arrangement of molecules in a pattern referred to as a "lattice").

The term "seeding" as used herein refers to starting or promoting a crystallization event using a small amount of material.

Crystalline forms of a substance can be obtained by a number of techniques, as is known in the art. Exemplary techniques for obtaining, producing, or manufacturing crystalline forms of ester of 17-hydroxyprogesterone (e.g., 17-hydroxyprogesterone caproate) include e.g., melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding and solvent-drop grinding. In some aspect, the crystalline form of ester of 17-hydroxyprogesterone (e.g. 17-hydroxyprogesterone caproate) is generated from recrystallization of solid API from a solvent. In one aspect, the solvent (for crystallization or recrystallization) is an alcohol (e.g., ethanol, methanol, or propanol), fatty acid (e.g., oleic acid, linoleic acid, or linoleic acid), alkane (e.g., hexane, heptane, pentane, or halogenated alkane), oil (e.g., vegetable oil, castor oil, or hydrogeneated oil), an ester, or any other suitable solvent (e.g., pyridine, benzene, or toluene). In one aspect, the crystalline form of ester of 17-hydroxyprogesterone (e.g., 17-hydroxyprogesterone caproate) is generated from recrystallization of solid API from a solvent in the presence of a seeding agent. In one aspect, the seeding agent is a steroid. In one aspect, the seeding agent is a derivative of 17HPC. In one aspect, the seeding agent is an ester of 17-hydroxyprogesterone that is not the caproate ester.

Typically, crystalline forms of a specific ester of 17-hydroxyprogesterone (e.g. 17-hydroxyprogesterone caproate) can be distinguished from each other by one or more physical or analytical properties such as rate of dissolution, infrared or raman spectroscopy, x-ray diffraction techniques such as single crystal and powder diffraction techniques, solid state-NMR (SS-NMR), thermal techniques such as melting point, differential thermal analysis (DTA), differential scanning calorimetry (DSC), thermal gravimetric analysis (TGA) and other methods as disclosed elsewhere in the specification or available to the skilled artisan. Other methods to characterize or distinguish a pseudopolymorph from another isostructural polymorph, pseudopolymorph, desolvate or anhydrate include elemental analysis, Karl-Fisher titration, dynamic vapor sorption analysis, thermogravimetric-infrared spectroscopic analysis (TG-IR), residual solvent gas chromatography, 1H-NMR etc.

Thus, in one embodiment, an ester of 17-hydroxyprogesterone (e.g., 17-hydroxyprogesterone caproate) is provided which has one or more advantageous properties compared to other forms such as chemical, crystalline, or polymorphic purity, increased crystallinity, flowability, solubility, dissolution rate, bioavailability, morphology or crystal habit, specific surface and pycnometric density, bulk/tap density, stability (e.g., such as chemical stability as well as thermal and mechanical stability with respect to polymorphic conversion), stability towards hydration and/or storage stability, a lower degree of hygroscopicity, low content of residual solvent(s) and advantageous processing and handling characteristics such as compressibility and bulk density. The ester of 17-hydroxyprogesterone (e.g., 17-hydroxyprogesterone caproate) is crystalline, non-crystalline, or a mixture thereof. In specific aspects of this embodiment, the ester of 17-hydroxyprogesterone (e.g., 17-hydroxyprogesterone caproate) in solid state form has unexpectedly improved dissolution, solubility, bioavailability, bioactivity, fluctuation index, processing, manufacturing, storage, taste, color, aggregates or granules.

In one embodiment, solid state ester of 17-hydroxyprogesterone (e.g., 17-hydroxyprogesterone caproate) is provided. In one aspect of this embodiment, the ester of 17-hydroxyprogesterone (e.g., 17-hydroxyprogesterone caproate) is crystalline or non-crystalline ester of 17-hydroxyprogesterone (e.g., 17-hydroxyprogesterone caproate), or a mixture thereof. In a specific aspect, the solid state API is amorphous ester of 17-hydroxyprogesterone (e.g., 17-hydroxyprogesterone caproate). The solid state API is particularly suitable for administration to a human. In one aspect, the solid state API is a specific crystalline ester of 17-hydroxyprogesterone (e.g., 17-hydroxyprogesterone caproate) form (e.g., substantially similar to that characterized in the Examples and figures by XRD. In a specific aspect, the solid state API is crystalline ester of 17-hydroxyprogesterone (e.g., 17-hydroxyprogesterone caproate) having 50%, 40%, 30%, 20%, 10%, 5%, 2%, or 1% or less by total weight amorphous ester of 17-hydroxyprogesterone (e.g., 17-hydroxyprogesterone caproate). In another aspect, the solid state API is a solvate or a pseudopolymorph of ester of 17-hydroxyprogesterone (e.g. 17-hydroxyprogesterone caproate). In another aspect, the solid state API is a polymorph of ester of 17-hydroxyprogesterone (e.g., 17-hydroxyprogesterone caproate). In another aspect, the solid state API is a hydrate of ester of 17-hydroxyprogesterone (e.g., 17-hydroxyprogesterone caproate). In yet another aspect, the solid state API is crystalline ester of 17-hydroxyprogesterone (e.g., 17-hydroxyprogesterone caproate) form having 50%, 40%, 30%, 20%, 10%, 5%, 2%, or 1% or less by total weight of API of other crystalline forms of ester of 17-hydroxyprogesterone (e.g. 17-hydroxyprogesterone caproate). In one aspect, the solid state API is a crystalline ester of 17-hydroxyprogesterone (e.g., 17-hydroxyprogesterone caproate) having a melting point in the range of 110 to 130° C., 115 to 125° C., 117 to 124° C., as determined by differential scanning calorimetry. In one aspect, the solid state API has a melting point as determined by differential scanning calorimetry characteristic of a single crystal form or non-amorphous ester of 17-hydroxyprogesterone (e.g., 17-hydroxyprogesterone caproate). In one aspect, the solid state API is crystalline ester of 17-hydroxyprogesterone (e.g. 17-hydroxyprogesterone caproate) having 1, 2, 3, 4, 5, 6, 7, 8, 9, 10, 11, 12, 13, 14, 15, 16, 17, 18 or more peaks as determined by XRD corresponding to those in FIG. 5 (one aspect, the peaks are chosen from the 7 tallest peaks in the reference spectrum). In again yet another aspect, the solid state API is ester of 17-hydroxyprogesterone (e.g. 17-hydroxyprogesterone caproate) having 50%, 40%, 30%, 20%, 10%, 5%, 2%, or 1% or less by total weight of crystalline ester of 17-hydroxyprogesterone (e.g., 17-hydroxyprogesterone caproate). In one aspect, the solid state API is crystalline ester of 17-hydroxyprogesterone (e.g., 17-hydroxyprogesterone caproate) which is not milled or is milled, micronized, or nanosized. In one aspect, the solid state API is ester of 17-hydroxyprogesterone (e.g., 17-hydroxyprogesterone caproate) having a $D_{50}$ of greater than 1000 µm, from 355 to 1000 µm, from 180 to 355 µm, from 125 to 180 µm, from 90 to 125 µm, from 1 to 90 µm, or less than 1 µm. In one aspect, the solid state API is ester of 17-hydroxyprogesterone (e.g., 17-hydroxyprogesterone caproate) having a particle size of less than 200 nm, from 200 to 500 nm, from 500 to 1000 nm, from 1 to 50 µm, from 50 µm to 250 µm, from 250 µm to 500 µm, from 500 µm to 1000 µm, or greater than 1000 µm. In one aspect, the solid state API is ester of 17-hydroxyprogesterone (e.g., 17-hydroxyprogesterone caproate) having a $D_{10}$, $D_{50}$, or $D_{90}$ that is less than 200 nm, from 200 to 500 nm, from 500 to 1000 nm, from 1 to 50 µm, from 50 to 250 µm, from 250 to 500 µm, from 500 to 1000 µm, or greater than 1000 µm. In one aspect, the solid state ester of 17-hydroxyprogesterone (e.g., 17-hydroxyprogesterone caproate) is a composition having greater than 1 g, 2 g, 50 g, 500 g, 1 kg, 10 kg, 50 kg, 100 kg, 200 kg, 500 kg, 1000 kg, 2000 kg, 5000 kg, or 10,000 kg solid state ester of 17-hydroxyprogesterone (e.g., 17-hydroxyprogesterone caproate). In one aspect, the release profile of the ester of 17-hydroxyprogesterone (e.g., 17-hydroxyprogesterone caproate) does not change substantially as a function of time.

Production of Amorphous API or Different Crystal Forms of Solid State API

Described herein are different forms of API, particularly ester of 17-hydroxyprogesterone (e.g., 17-hydroxyprogesterone caproate). The identification of different forms of API yields new, improved properties related to the use of the API.

A number of different forms, including crystalline forms of ester of 17-hydroxyprogesterone (e.g., 17-hydroxyprogesterone caproate) may exist. Crystalline ester of 17-hydroxyprogesterone (e.g., 17-hydroxyprogesterone caproate) may be produced according to the Figures and as described herein or by other methods available to the ordinary skilled artisan in view of this disclosure to obtain solid state forms having desirable properties.

Amorphous ester of 17-hydroxyprogesterone (e.g., 17-hydroxyprogesterone caproate) is another solid state API form. A number of techniques are available for preparing amorphous ester of 17-hydroxyprogesterone (e.g., 17-hydroxyprogesterone caproate). For example, flash evaporation, lyophilization, quench cooling of the melt, spray drying, grinding, supercritical fluids are non-limiting techniques that can be used to make amorphous API. In some aspects, the amorphous ester of 17-hydroxyprogesterone (e.g., 17-hydroxyprogesterone caproate) is metastable.

Experimental Instrumentation and Conditions for Analyzing Solid State API

A variety of techniques may be used to identify or characterize solid state API, particularly solid state ester of 17-hydroxyprogesterone (e.g. 17-hydroxyprogesterone caproate). Fourier Transform-Raman Spectroscopy ("FT-Raman") is useful for characterizing and identify solid state forms of (ester of 17-hydroxyprogesterone (e.g., 17-hydroxyprogesterone caproate). For example, different solid API forms may be characterized using a Bruker RFS100 instrument, with Nd:YAG 1064 nm excitation, 300 mW laser power, Ge detector, using 64 scans over the range of 25-3500 cm', and with 2 cm' resolution. As is understood by the ordinary skilled artisan, the parameters and instrumentation for FT-Raman may be modified depending on the instrument, the solid state API and goal(s) of the analysis.

Another useful technique for characterization is Power X-ray Diffraction ("XRD"). XRD can be performed with a Bruker D8 Advance X-ray diffractometer with CuKα-radiation. The standard measuring conditions are e.g., tube power 35 kV/45 mA; step size 0.017° (2θ); step time 105±5 sec; scanning range 2°-50° (2θ); divergence slit equal to variable V12; sample rotation; a Vantec1 detector; the opening angle 3°; channel number 360±10; the y-axis shows the value intensity/number of active detector channels/sec; silicon single crystal sample holders; and the sample dimensions depth/diameter was 0.1 mm/~12 mm. As is understood by the ordinary skilled artisan, the parameters and instrumentation for PDXR may be modified depending on the instrument, the solid state API and goal(s) of the analysis. In one embodiment, the solid state ester of 17-hydroxyprogesterone (e.g., 17-hydroxyprogesterone caproate) is crystalline or substantially crystalline as indicated by XRD. An example of an XRD spectra is shown in FIG. 6 for crystalline or substantially crystalline ester of 17-hydroxyprogesterone (e.g., 17-hydroxyprogesterone caproate). FIG. 5 shows well defined peaks corresponding to crystalline or substantially crystalline ester of 17-hydroxyprogesterone (e.g., 17-hydroxyprogesterone caproate) with little or no amorphous API (as indicated by the absence of an "amorphous halo" in the spectra in the 20-40 degree 2θ range). In one aspect, the solid state API described herein has 1, 2, 3, 4, 5, 6, 7, 8, 9, 10, 11, or 12 or more of the peaks that corresponds to those in FIG. 5 (in one aspect these peaks are chosen from the 7 tallest peaks in the reference spectrum). Thermogravimetric-Fourier transform Infrared Spectroscopy ("TG-FTIR") can also be used to characterize or analyze solid state API. For example, TG-FTIR can be performed with a Netzsch Thermo-Microbalance TG 209 coupled with a Bruker FT-IR Spectrometer Vector 22, using an aluminum crucible (open or with a microhole), under a nitrogen atmosphere, and e.g., at a heating rate of 10° C./min over the range of 25° C. to 350° C. As is understood by the ordinary skilled artisan, the parameters and instrumentation for TG-FITR may be modified depending on the instrument, the solid state API and goal(s) of the analysis.

Characterization/Analysis of API can also be performed using Differential Scanning calorimetry ("DSC"). For example, DSC can be performed with a Perkin Elmer Differential Scanning calorimeter, using closed gold crucibles, a heating rate of 10° C. $\min^{-1}$ or 20° C. over a range from 0° C. to 300° C. (or e.g., over a range from 5° C. to 250° C.). As is understood by the ordinary skilled artisan, the parameters and instrumentation for DSC may be modified depending on the instrument, the solid state API and goal(s) of the analysis.

Thus, in yet another embodiment, a solid state API, e.g., ester of 17-hydroxyprogesterone (e.g., 17-hydroxyprogesterone caproate), is provided which has a melting point in the range of about 50 to 300° C., as determined by DSC. In a more specific embodiment, a solid state API is provided which has a melting point in the range of about 50 to 200° C., as determined by DSC. In another specific embodiment, a solid state API is provided which has a melting point in the range of about 100 to 150° C., as determined by DSC. In one aspect of this embodiment, the melting point of the solid state API is characteristic of a single physical form of API e.g., a single crystalline form or amorphous API.

In yet another embodiment, a pharmaceutical composition or unit dosage form having a solid state API (e.g., ester of 17-hydroxyprogesterone (e.g., 17-hydroxyprogesterone caproate) is provided where the API in the pharmaceutical composition has a melting point in the range of about 50 to 150° C., as determined by DSC. The pharmaceutical composition or unit dosage form of this embodiment comprises or is prepared from solid state API and one or more pharmaceutically acceptable carriers. In a more specific embodiment, a pharmaceutical composition is provided having or prepared from solid state API where the solid state API starting material has a melting point in the range of about 85 to 145° C., as determined by DSC. In a more specific embodiment, a pharmaceutical composition is provided having or prepared from solid state API where the solid state starting material has a melting point in the range of about 110 to 130° C., 115 to 125° C., 117 to 124° C., as determined by DSC. In a specific embodiment, a pharmaceutical composition is provided having or prepared from solid state which has a melting point of API in the range of about 115 to 125° C., as determined by DSC. In one aspect of this embodiment, the melting point of the pharmaceutical composition or unit dosage form does not have a peak corresponding to the melting point peak of the API from which it was prepared as determined by DSC. For example, the melting point of the starting solid state API is in the range of 115 to 125° C. and when the melting point of the pharmaceutical composition comprising the API is determined the melting point peak in the range of 115 to 125° C. disappears, is diminished or substantially diminished.

Dynamic Vapor Sorption (DVS) analysis is another technique for characterizing and analyzing API. For example, DVS can be performed with a Surface Measurement Systems DVS-1 water vapor sorption analyzer. The experiments can be run by placing the sample on a quartz holder on top of a microbalance, and allowing the sample to equilibrate at 50% relative humidity (r.h.) before starting the pre-defined humidity program. The program can proceed e.g., in the following steps: 1 hour at 50% r.h.; 50% to 0% r.h. at a rate of 5% r.h. change per hour; 5 hours at 0% r.h; 0% r.h to 96% r.h. at 5% r.h change per hour; 5 hours at 95% r.h.; 95% r.h. to 50% r.h. at a rate of 5% r.h. change per hour, and followed by one hour at 50% r.h. As is understood by the ordinary skilled artisan, the parameters and instrumentation for DVS may be modified depending on the instrument, the solid state API and goal(s) of the analysis.

High performance liquid chromatography (HPLC) is also useful for analyzing or characterizing API. In some of the embodiments, the purity of the amorphous form of ester of 17-hydroxyprogesterone (e.g., 17-hydroxyprogesterone caproate) as measured by high pressure liquid chromatography is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at a suitable wavelength e.g., about 240 nm or about 242 nm. In some embodiments, the amorphous form of ester of 17-hydroxyprogesterone (e.g., 17-hydroxyprogesterone caproate) is about 100.0% pure as measured by HPLC as area under the curve as observed at a suitable wavelength, e.g., at a wavelength of from about 200 nm to about 300 nm, e.g., about 240 nm or 242 nm.

In some of the embodiments, the purity of a crystalline form of ester of 17-hydroxyprogesterone (e.g., 17-hydroxyprogesterone caproate) as measured by HPLC is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at a suitable wavelength e.g., about 240 nm or about 242 nm. In some embodiments of the invention, a crystalline form of ester of 17-hydroxyprogesterone (e.g., 17-hydroxyprogesterone caproate) is about 100.0% pure as measured by HPLC as area under the curve as observed at a suitable wavelength, e.g., at a wavelength of from about 200 nm to about 300 nm, e.g., about 240 nm or 242 nm.

As is understood by the ordinary skilled artisan, solid state NMR and other techniques can be used to analyze or characterize solid API and forms thereof in view of this disclosure.

Production of Different Sizes of Solid State API

Composition having different particles sizes or distributions of particles sizes can be produced by any suitable method. Micronization techniques can be based on friction to reduce particle size; such methods include milling, bashing and grinding. Another technique of producing different sized API particles involves supercritical fluids where the API is dissolved in a solvent at high temperature and pressure and they sprayed out of a nozzle, causing the formation of API particles of particular sizes or within particular size ranges/distributions. Some basic supercritical fluid techniques are RESS process (Rapid Expansion of Supercritical Solutions), the SAS method (Supercritical Anti-Solvent) and the PGSS method (Particles from Gas Saturated Solutions).

Particle Size and Morphology Analysis

Solid state API particles can be analyzed by a number of techniques. For example, Particle size can analyzed by photon correlation spectroscopy (PCS) using a Malvern ZetaSizer 2000 HS (Malvern Instruments, Malvern, UK). The measuring mode applied can be e.g., Contin-Auto mode. PCS yields the mean diameter of the bulk population (z-average) and a polydispersity index (PI) ranging from 0 (monodisperse) through 0.10-0.20 (relatively monodisperse) to >0.5 for a broad size distribution. The measuring range of PCS is approximately 3 nm-3 μm. As is understood by the ordinary skilled artisan, the parameters and instrumentation for PCS may be modified depending on the instrument, the solid state API and goal(s) of the analysis.

Solid state API can also be analyzed by electron microscopy. Solid particles are deposited on metallic stubs then placed in liquid nitrogen and dried under vacuum. The freeze-dried particles are coated uniformly with gold. All samples are examined for morphology and surface properties using a scanning electron microscope (e.g., Joel, SEM, JSM-25 SII, Tokyo, Japan). Particle size, polydispersity index and zeta potential were initially measured by a laser particle size analyser (Submicron Particle Size Analyser 90 plus, Brookhaven Instrument Co., Holtsville, N.Y., USA). An aliquot of solid state API particles can be diluted with e.g., 3 ml of deionized water. The diluted API samples are loaded into a 4 ml cuvette and the particle size and zeta potential measurement can be conducted at e.g., ambient temperature. As is understood by the ordinary skilled artisan, the parameters and instrumentation for electron microscopy may be modified depending on the instrument, the solid state API and goal(s) of the analysis.

The particle size can also be estimated by XRD e.g., by applying the Sherrer equation which relates the size particles (e.g., crystal particles or crystallites), in a solid to the broadening of a peak in a diffraction pattern.

Release Profile of Solid State API

In one embodiment, the release profile (e.g., a profile comprising 2, 3, 4, 5, or 6 or more time points each at least 5, 10, or 15 minutes apart or a single time point) of solid state ester of 17-hydroxyprogesterone (e.g. 17-hydroxyprogesterone caproate) API does not change substantially as a function of storage time. In one aspect, the release profile of solid state 17-HPC does not substantially change over a period of 1, 2, 3, 4, 5, 6, 7, 8, 9, 10, 11, 12, 13, 14, 15, or 16 weeks. In one aspect, the release profile of solid state 17-HPC does not substantially change over a period of 1, 2, 3, 4, 5, 6, 7, 8, 9, 10, 11, 12, 13, 14, 15, or 16 months. In one aspect, the release profiles is tested using a USP type 2 apparatus at 100 rpm in about 1000 mL 8%, 12% or 16% Triton X-100 solution in water at a specific temperature e.g., 20.0, 37.0 or 40.0° C. (±0.5). In one aspect, a release profile that does not substantially change over a period of time refers to a release profile that changes by less than plus/minus 50%, 40%, 30%, 20%, or 10% or less of amount ester of 17-hydroxyprogesterone (e.g., 17-hydroxyprogesterone caproate) released at one or more specific time point under specific conditions.

Exemplary Pharmaceutical Compositions and Unit Dosage Forms

The pharmaceutical compositions and oral dosage forms (e.g., capsule or tablet) described herein prepared from or comprising solid ester of 17-hydroxyprogesterone (e.g., 17-hydroxyprogesterone caproate) API can include a variety of pharmaceutically acceptable carriers or excipeints known in the art. Exemplary pharmaceutical compositions and unit dosage forms are given below in Tables A-E. These Tables describe various formulations containing 17HPC. In one embodiment, the pharmaceutical composition or oral dosage form includes 17HPC and a carrier. According to one aspect of this embodiment, the carrier can include a surfactant. In one aspect, the surfactant is a lipophilic or hydrophilic surfactant. In one aspect, the surfactant is an ionic or non-ionic surfactant. In yet another aspect, the pharmaceutical composition includes 17HPC and one or more of: a diluent, filler, binder, adhesive, disintegrant, lubricant, antioxidant, surfactant, colorant, flavorant, coating agent, solvent, and water. In another aspect, the pharmaceutical composition or unit dosage form includes (1) 17HPC, (2) a diluent and (3) one or more other pharmaceutically acceptable excipients. In another aspect, the pharmaceutical composition or unit dosage form includes (1) 17HPC, (2) a binder and (3) one or more other pharmaceutically acceptable excipients. In another aspect, the pharmaceutical composition or unit dosage form includes (1) 17HPC, (2) a disintegrant and (3) one or more other pharmaceutically acceptable excipients. In another aspect, the pharmaceutical composition or unit dosage form includes (1) 17HPC, (2) a lubricant and (3) one or more other pharmaceutically acceptable excipients. In another aspect, the pharmaceutical composition or unit dosage form includes (1) 17HPC, (2) a diluent (3) a binder and (4) one or more other pharmaceutically acceptable excipients. In another aspect, the pharmaceutical composition or unit dosage form includes (1) 17HPC, (2) a diluent (3) a disintegrant and (4) one or more other pharmaceutically acceptable excipients. In another aspect, the pharmaceutical composition or unit dosage form includes (1) 17HPC, (2) a diluent (3) a lubricant and (4) one or more other pharmaceutically acceptable excipients. In another aspect, the pharmaceutical composition or unit dosage form includes (1) 17HPC, (2) a binder (3) a disintegrant and (4) one or more other pharmaceutically acceptable excipients. In another aspect, the pharmaceutical composition or unit dosage form includes (1) 17HPC, (2) a binder (3) a lubricant and (4) one or more other pharmaceutically acceptable excipients. In another aspect, the pharmaceutical composition or unit dosage form includes (1) 17HPC, (2) a disintegrant (3) a lubricant and (4) one or more other pharmaceutically acceptable excipients. In another aspect, the pharmaceutical composition or unit dosage form includes (1) 17HPC, (2) a diluent (3) a binder (4) a disintegrant and (5) one or more other pharmaceutically acceptable excipients. In another aspect, the pharmaceutical composition or unit dosage form includes (1) 17HPC, (2) a diluent (3) a binder (4) a lubricant and (5) one or more other pharmaceutically acceptable excipients. In another aspect, the pharmaceutical composition or unit dosage form includes (1) 17HPC, (2) a diluent (3) a disintegrant (4) a lubricant and (5) one or more other pharmaceutically acceptable excipients. In another aspect, the pharmaceutical composition or unit dosage form includes (1) 17HPC, (2) a binder (3) a disintegrant (4) a lubricant and (5) one or more other pharmaceutically acceptable excipients. In another aspect, the pharmaceutical composition or unit dosage form includes (1) 17HPC, (2) a diluent (3) a binder (4) a disintegrant, (5) a lubricant and (5) one or more other pharmaceutically acceptable excipients. In some aspects of this embodiment, the pharmaceutical composition or oral dosage forms are as described below in Tables A-E. In some aspects, the 17HPC is present in the pharmaceutical composition or unit dosage form in an amount ranging from about 1 mg to about 1200 mg, In some aspects, the 17HPC is present in the pharmaceutical composition or unit dosage form in an amount ranging from about 10 mg to about 1000 mg, In some aspects, the 17HPC is present in the pharmaceutical composition or unit dosage form in an amount ranging from about 100 mg to about 900 mg, In some aspects, the 17HPC is present in the pharmaceutical composition or unit dosage form in an amount ranging from about 200 mg to about 800 mg, In some aspects, the 17HPC is present in the pharmaceutical composition or unit dosage form in an amount ranging from about 300 mg to about 700 mg, In some aspects, the 17HPC is present in the pharmaceutical composition or unit dosage form in an amount ranging from about 350 mg to about 700 mg, In some aspects, the 17HPC is present in the pharmaceutical composition or unit dosage form in an amount ranging from about 400 mg to about 700 mg, In some aspects, the 17HPC is present in the pharmaceutical composition or unit dosage form in an amount ranging from about 450 mg to about 650 mg, In some aspects, the 17HPC is present in the pharmaceutical composition or unit dosage form in an amount ranging from about 500 mg to about 600 mg, Typically, the total weight of the unit dosage forms described in the following Tables (or elsewhere in the specification) is greater than 10 mg and less than 2000 mg. In some aspects, the unit dosage forms (e.g., tablet, caplet, capsule, etc.) as described in the Tables below have a total weight of from 10-100 mg, 100-200 mg, 200-300 mg, 300-400 mg, 500-600 mg, 600-700 mg, 700-800 mg, 800-900 mg, 900-1000 mg, 1000-1100 mg, 1100-1200 mg, 1200-1300 mg, 1300-1400 mg, 1400-1500 mg, 1500-1600 mg 1600-1700 mg, 1700-1800 mg, 1800-1900 mg, or 1900-2000 mg. In some aspects, the loading of the 17HPC in the pharmaceutical compositions and unit dosage forms described in the Tables below is greater than 10%, 15%, 20%, 25%, 30%, 35%, 40%, 45%, 50%, 55%, 60%, 75%, 80%, 85%, 90%, or 95% (or within any range defined by any two of these value (e.g., 30%-75% or 45%-65%, etc.)). Loading is the mg amount of 17HPC/total mg amount of the unit dosage form or pharmaceutical composition multiplied by 100. In one aspect, the 17HPC is present in particulate form, partially solubilized, fully solubilized, or amorphous form. In one aspect, the 1 HPC is present as crystalline particulate form. In one aspect, the crystalline particulate form of 17HPC has a $D_{50}$ of from 1000-750, 750-500, 500-250, 250-200, 200-150, 150-100, or 100-50 microns. In one aspect, the crystalline particulate form of 17HPC has a $D_{50}$ of from 50-40, 40-30, 30-20, 20-10, or 10-1 microns. In one aspect, the crystalline particulate form of 17HPC has a $D_{50}$ of from 1000-750, 750-500, 500-250, 250-200, 200-150, 150-100, or 100-50 nanometers. In some aspects of this embodiment, the pharmaceutical composition or unit dosage form is a powder, granulate, particulate, bead, pellet, sprinkle, suspension, solution, tablet, caplet, capsule, or a combination thereof. In some aspects of this embodiment, the pharmaceutical composition or unit dosage form is a matrix tablet. In some aspects of this embodiment, the pharmaceutical composition or unit dosage form is a coated or uncoated tablet. In some aspects of this embodiment, the pharmaceutical composition or unit dosage form is immediate release or controlled release. In some aspects, the controlled release selected can be, intermediate, delayed, extended, sustained, pulsatile, gastric, enteric or colonic. In some aspects of this embodiment, the pharmaceutical composition of unit dosage form is administered once, twice or three time a day to an individual in need of treatment (e.g., a pregnant female). In yet another aspect, the pharmaceutical composition or dosage form is administered with food. In some aspects, the oral dosage form or pharmaceutical composition can provide a 17-hydroxyprogesterone caproate $C_{avg\text{-}24h}$ of greater than about 0.1, 0.5 or 1.0 ng/mL when adminstered to a human subject (female or pregnant female) once or twice daily as 1, 2, 3, 4, 5, 6, 7, 8, 9, or 10 unit dosage forms. In some aspects of this embodiment, the 17-hydroxyprogesterone caproate compositions or dosage forms can provide a fluctuation in the 17-hydroxyprogesterone caproate levels less than about 2000, 1500, 1000, 900, 800, 700, 600, 500, 400, 300, 200, 175, 150, 140, 130, 120, 110 or 100 ng/mL, or greater than about 1, 10, 15, 25, 50, 75, 100, 200, 300 or 400 ng/mL (or within a range as defined by any two of these values) wherein the fluctuation is determined by the difference of the mean steady state $C_{max}$ and the mean steady state $C_{min}$ of 17-hydroxyprogesterone caproate in plasma or serum or blood, upon oral administration. In a specific aspect, the $AUC_{(0\text{-}24h)}$ to dose ratio is between about 1.5 and about 10.0 ng*h mL$^{-1}$mg$^{-1}$. In a specific aspect, the $AUC_{(0\text{-}24h)}$ to dose ratio is between about 2.0 and about 10.0 ng*h mL$^{-1}$mg$^{-1}$. In a specific aspect, the $AUC_{(0\text{-}24h)}$ to dose ratio is between about 3.0 and about 10.0 ng*h mL$^{-1}$mg$^{-1}$. In a specific aspect, the $AUC_{(0\text{-}24h)}$ to dose ratio is between about 4.0 and about 10.0 ng*h mL$^{-1}$mg$^{-1}$. In a specific aspect, the $AUC_{(0\text{-}24h)}$ to dose ratio is between about 5.0 and about 10.0 ng*h mL$^{-1}$mg$^{-1}$. In a specific aspect, the $AUC_{(0\text{-}24h)}$ to dose ratio is between about 6.0 and about 10.0 ng*h mL$^{-1}$mg$^{-1}$. In a specific aspect, the $AUC_{(0\text{-}24h)}$ to dose ratio is between about 7.0 and about 10.0 ng*h mL$^{-1}$mg$^{-1}$.

TABLE A

17HPC + Carrier

| Ingredients | Composition (% w/w) | | |
|---|---|---|---|
| | A | B | C |
| 17-a-Hydroxyprogesterone Caproate (particle size >50 µm) | 1-99 | — | — |
| 17-a-Hydroxyprogesterone Caproate (micronized: <15 µm or nanosized: <1 µm) | — | 1-99 | — |
| 17-a-Hydroxyprogesterone Caproate (milled, <50 µm) | — | — | 1-99 |
| Carrier | 1-99 | 1-99 | 1-99 |
| Granulating solvent | qs | qs | qs |
| % Release in 1 hrs | ≥20 | ≥20 | ≥20 |

TABLE A1

Exemplary Composition of Surfactants, When Present, in Carriers

| Surfactant | Composition in Carriers (% w/w) | | | | | | | | |
|---|---|---|---|---|---|---|---|---|---|
| | AS1 | AS2 | AS3 | BS1 | BS2 | BS3 | CS1 | CS2 | CS3 |
| Lipophilic additive (e.g. lipophilic surfactant) | 100 | — | 5-95 | 100 | — | 5-95 | 100 | — | 5-95 |
| Hydrophilic additive (e.g. hydrophilic surfactant) | — | 100 | 5-95 | — | 100 | 5-95 | — | 100 | 5-95 |

AS: A composition in Table A + Surfactant
BS: B composition in Table A + Surfactant
CS: C composition in Table A + Surfactant According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE A2

Exemplary Composition of Carrier

| Carrier component | Composition in carriers (% w/w) |
| --- | --- |
| Diluent/filler (e.g. lactose, starch, glucose, magnesium salt, potassium chloride) | 1-50 |
| Binder/adhesive (e.g. cellulose derivatives, starch, gelatin) | 1-50 |
| Disintegrant (e.g. cellulose derivatives, crospovidone, starch) | 1-20 |
| Lubricant/glidant (e.g. magnesium stearate, colloidal silicon dioxide) | 0-5 |
| Anti-oxidant | 0-50 |
| Surfactant | 0-95 |
| Colorant | 0-5 |
| Flavor | 0-5 |
| Coating agent | 0-5 |
| Solvent | 0-60 |
| Water | 0-40 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE B1

Drug + Diluent + Carriers Except Diluents

| Ingredients | Composition (% w/w) | | |
| --- | --- | --- | --- |
| | A2A | B2A | C2A |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Diluent/filler (e.g. lactose, starch, glucose, magnesium salt, potassium chloride) | 1-50 | 1-50 | 1-50 |
| Carriers except diluents | 1-50 | 1-50 | 1-50 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE B2

Drug + Binder + Carriers Except Binders

| Ingredients | Composition (% w/w) | | |
| --- | --- | --- | --- |
| | A2B | B2B | C2B |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Binder/adhesive (e.g. cellulose derivatives, starch, gelatin) | 1-50 | 1-50 | 1-50 |
| Carriers except binders | 1-50 | 1-50 | 1-50 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE B3

Drug + Disintegrant + Carriers Except Disintegrants

| Ingredients | Composition (% w/w) | | |
| --- | --- | --- | --- |
| | A2C | B2C | C2C |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Disintegrant (e.g. cellulose derivatives, crospovidone, starch) | 1-20 | 1-20 | 1-20 |
| Carriers except disintegrants | 1-80 | 1-80 | 1-80 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE B4

Drug + Lubricant + Carriers Except Lubricants

| Ingredients | Composition (% w/w) | | |
|---|---|---|---|
| | A2D | B2D | C2D |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Lubricant/glidant (e.g. magnesium stearate, colloidal silicon dioxide) | 0-5 | 0-5 | 0-5 |
| Carriers except lubricants | 1-95 | 1-95 | 1-95 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE C1

Drug + Diluent + Binder + Carriers

| Ingredients | Composition (% w/w) | | |
|---|---|---|---|
| | A3A | B3A | C3A |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Diluent/filler (e.g. lactose, starch, glucose, magnesium salt, potassium chloride) | 1-50 | 1-50 | 1-50 |
| Binder/adhesive (e.g. cellulose derivatives, starch, gelatin) | 1-50 | 1-50 | 1-50 |
| Carriers | 1-50 | 1-50 | 1-50 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE C2

Drug + Diluent + Disintegrant + Carriers

| Ingredients | Composition (% w/w) | | |
|---|---|---|---|
| | A3B | B3B | C3B |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Diluent/filler (e.g. lactose, starch, glucose, magnesium salt, potassium chloride) | 1-50 | 1-50 | 1-50 |
| Disintegrant (e.g. cellulose derivatives, crospovidone, starch) | 1-20 | 1-20 | 1-20 |
| Carriers | 1-50 | 1-50 | 1-50 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE C3

Drug + Diluent + Lubricant + Carriers

| Ingredients | Composition (% w/w) | | |
|---|---|---|---|
| | A3C | B3C | C3C |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Diluent/filler (e.g. lactose, starch, glucose, magnesium salt, potassium chloride) | 1-50 | 1-50 | 1-50 |
| Lubricant/glidant (e.g. magnesium stearate, colloidal silicon dioxide) | 0-5 | 0-5 | 0-5 |
| Carriers | 1-50 | 1-50 | 1-50 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE C4

Drug + Binder + Disintegrant + Carriers

| Ingredients | Composition (% w/w) | | |
|---|---|---|---|
| | A3D | B3D | C3D |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Binder/adhesive (e.g. cellulose derivatives, starch, gelatin) | 1-50 | 1-50 | 1-50 |
| Disintegrant (e.g. cellulose derivatives, crospovidone, starch) | 1-20 | 1-20 | 1-20 |
| Carriers | 1-50 | 1-50 | 1-50 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE C5

Drug + Binder + Lubricant + Carriers

| Ingredients | Composition (% w/w) | | |
|---|---|---|---|
| | A3E | B3E | C3E |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Binder/adhesive (e.g. cellulose derivatives, starch, gelatin) | 1-50 | 1-50 | 1-50 |
| Lubricant/Glidant (e.g. magnesium stearate, colloidal silicon dioxide) | 1-5 | 1-5 | 1-5 |
| Carriers | 1-50 | 1-50 | 1-50 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE C6

Drug + Disintegrant + Lubricant + Carriers

| Ingredients | Composition (% w/w) | | |
|---|---|---|---|
| | A3F | B3F | C3F |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Disintegrant (e.g. cellulose derivatives, crospovidone, starch) | 1-20 | 1-20 | 1-20 |
| Lubricant/Glidant (e.g. magnesium stearate, colloidal silicon dioxide) | 1-5 | 1-5 | 1-5 |
| Carriers | 1-75 | 1-75 | 1-75 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE D1

Drug + Diluent + Binder + Disintegrant + Carriers

| Ingredients | Composition (% w/w) | | |
|---|---|---|---|
| | A4A | B4A | C4A |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Diluent/filler (e.g. lactose, starch, glucose, magnesium salt, potassium chloride) | 1-50 | 1-50 | 1-50 |
| Binder/adhesive (e.g. cellulose derivatives, starch, gelatin) | 1-50 | 1-50 | 1-50 |
| Disintegrant (e.g. cellulose derivatives, crospovidone, starch) | 1-20 | 1-20 | 1-20 |
| Carriers | 1-50 | 1-50 | 1-50 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE D2

Drug + Diluent + Binder + Lubricant + Carriers

| Ingredients | Composition (% w/w) | | |
|---|---|---|---|
| | A4B | B4B | C4B |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Diluent/filler (e.g. lactose, starch, glucose, magnesium salt, potassium chloride) | 1-50 | 1-50 | 1-50 |
| Binder/adhesive (e.g. cellulose derivatives, starch, gelatin) | 1-50 | 1-50 | 1-50 |
| Lubricant/Glidant (e.g. magnesium stearate, colloidal silicon dioxide) | 0-5 | 0-5 | 0-5 |
| Carriers | 1-50 | 1-50 | 1-50 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE D3

Drug + Diluent + Disintegrant + Lubricant + Carriers

| Ingredients | Composition (% w/w) | | |
|---|---|---|---|
| | A4C | B4C | C4C |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Diluent/filler (e.g. lactose, starch, glucose, magnesium salt, potassium chloride) | 1-50 | 1-50 | 1-50 |
| Disintegrant (e.g. cellulose derivatives, crospovidone, starch) | 1-20 | 1-20 | 1-20 |
| Lubricant/Glidant (e.g. magnesium stearate, colloidal silicon dioxide) | 0-5 | 0-5 | 0-5 |
| Carriers | 1-50 | 1-50 | 1-50 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE D4

Drug + Binder + Disintegrant + Lubricant + Carriers

| Ingredients | Composition (% w/w) | | |
|---|---|---|---|
| | A4D | B4D | C4D |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Binder/adhesive (e.g. cellulose derivatives, starch, gelatin) | 1-50 | 1-50 | 1-50 |
| Disintegrant (e.g. cellulose derivatives, crospovidone, starch) | 1-20 | 1-20 | 1-20 |
| Lubricant/Glidant (e.g. magnesium stearate, colloidal silicon dioxide) | 0-5 | 0-5 | 0-5 |
| Carriers | 1-50 | 1-50 | 1-50 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE E

Drug + Diluent + Binder + Disintegrant + Lubricant + Carriers

| Ingredients | Composition (% w/w) | | |
|---|---|---|---|
| | A5A | B5A | C5A |
| 17-a-Hydroxyprogesterone Caproate (particle size >50 μm) | 1-99 | — | — |
| 17-a-Hydroxyprogesterone Caproate (micronized: <15 μm or nanosized: <1 μm) | — | 1-99 | — |
| 17-a-Hydroxyprogesterone Caproate (milled, <50 μm) | — | — | 1-99 |
| Diluent/filler (e.g. lactose, starch, glucose, magnesium salt, potassium chloride) | 1-50 | 1-50 | 1-50 |
| Binder/adhesive (e.g. cellulose derivatives, starch, gelatin) | 1-50 | 1-50 | 1-50 |
| Disintegrant (e.g. cellulose derivatives, crospovidone, starch) | 1-20 | 1-20 | 1-20 |
| Lubricant/Glidant (e.g. magnesium stearate, colloidal silicon dioxide) | 0-5 | 0-5 | 0-5 |
| Carriers | 1-50 | 1-50 | 1-50 |
| Granulating solvent | qs | qs | qs |
| % Release in 1 hrs | ≥20 | ≥20 | ≥20 |

According to one aspect, the formulations (e.g., unit dosage forms) in the above table have from about 100 to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

As indicated in the Tables above, pharmaceutical compositions or unit dosage forms described herein can release greater than 20% of the 17 HPC at one hour when tested under appropriate conditions. The selection of conditions depends on a number of factors that the skilled artisan is aware of. In one aspect, the release of 17HPC is tested with a USP Type II Dissolution Apparatus using a specific aqueous media. In one aspect, the specific aqueous media is one in which provides sink conditions for the amount of 17HPC in the pharmaceutical composition or unit dosage form. Sink conditions refers to the ability of the aqueous media to completely dissolve all of the 17HPC and is determined by the solubility of 17HPC in that particular aqueous media. In one specific aspect, the release is determined in 2×, 3×, 4×, 5×, 6×, 7×, 8×, or 10× or more sink conditions. For example, 2× refers to the ability of the media to dissolve twice the total amount of the 17HPC in the pharmaceutical composition or unit dosage form (if the solubility of 17HPC was 1 mg/mL in a particular aqueous media and 1000 mL than that would be 2× for 500 mg of 17HPC; 4× for 250 mg 17HPC, etc.). In one aspect, the aqueous media has 0.5% (w/w) sodium lauryl sulfate. In another aspect, the aqueous media is simulated intestinal fluid having 0.5% w/w sodium lauryl sulfate. In another aspect, the aqueous media is 900 mL simulated intestinal fluid having 0.5% w/w sodium lauryl sulfate. In one aspect, the release is tested using a USP Type II apparatus at 50 or 100 rpm in about 1000 mL 8%, 12% or 16% Triton X-100 solution in water at a specific temperature e.g., 20.0, 37.0 or 40.0° C. (±0.5).

EXAMPLES

The following examples are provided to promote a more clear understanding of certain embodiments of the present invention, and are in no way meant as a limitation thereon. Unless otherwise specified or mentioned, all the compositions provided in the examples are with respect to % w/w of the final composition. Note that with the exception of the compositions listed in Examples 1, 7, 10, 17 and 36, the 17-hydroxyprogesterone caproate of all other example compositions can be in either treated (milled, micronized, or nanosized) or untreated form. The 17-hydroxyprogesterone Caproate in compositions 1, 7, 10, 17 and 36 are untreated for size reduction (i.e., unmilled, non-micronized, un-micronized or non-nanosized), and have an average particle size greater than 50 micrometers. The dosage forms of corresponding Examples were tested for release of the 17-hydroxyprogesterone caproate using a USP Type II apparatus, 50 rpm in 900 mL of simulated intestinal fluid having 0.5% w/w sodium lauryl sulfate at 37° C. The percent of the 17-hydroxyprogesterone caproate released from each composition was analyzed using HPLC.

Examples 1-6—17-hydroxyprogesterone Caproate Compositions 17-hydroxyprogesterone caproate compositions as recited in Examples 1 through 6 are prepared by using the respective components shown in Table I. Example 1 is the untreated crystalline form of 17-hydroxyprogesterone caproate filled into hard gelatin capsule. Example 2 is micronized 17-hydroxyprogesterone caproate without a carrier filled into hard gelatin capsule. Examples 3-6, are prepared as follows: The required quantities of each of the components of the respective composition, except 17-hydroxyprogesterone caproate are taken in a clean stainless steel container and mixed at about 50° C. to 70° C. using a stirrer. A molten clear-to-hazy mixture is obtained. The required amount of the 17-hydroxyprogesterone caproate is added to the clear-to-hazy mixture and stirred to form a homogenous liquid mixture. A predetermined weight of the resulting liquid mixture is disposed into appropriate size capsules according to the 17-hydroxyprogesterone caproate dose required. The capsules are allowed to solidify at room temperature and then banded, and packaged into HDPE bottles and sealed with a lid.

The 17-hydroxyprogesterone caproate released within 60 minutes from each of the compositions using the aforementioned dissolution testing parameters are shown in Table I. Moreover, FIG. 1 shows the comparative release of Examples 1 and 2 over a duration of 2 hours. It should be noted that the Examples 1 & 2 (17-hydroxyprogesterone caproate without a carrier) and Examples 3 to 6 (17-hydroxyprogesterone caproate admixed with at least one carrier) can be used for comparison purposes to help illustrate the advantages of the compositions and dosage forms of the current invention.

TABLE I

| Example No. Ingredients | 1 | 2 | 3 | 4 | 5 | 6 |
|---|---|---|---|---|---|---|
| | Composition in % w/w. | | | | | |
| 17-hydroxyprogesterone caproate | 100 | 100* | 12 | 15 | 11 | 18 |
| Lipophilic additive: Ex: Castor Oil NF | — | — | 53 | — | 48 | — |
| Lipophilic additive: Ex: Lauroglycol FCC | — | — | 35 | — | 32 | — |

TABLE I-continued

| Example No. Ingredients | 1 | 2 | 3 | 4 | 5 | 6 |
|---|---|---|---|---|---|---|
| | Composition in % w/w. | | | | | |
| Lipophilic additive: Glyceryl Monolinoleate, NF | — | — | — | 63 | — | 75 |
| Hydrophilic additive: Polyoxyl 40 Hydrogenated Castor Oil, NF | — | — | — | 16 | — | — |
| Hydrophilic additive: PEG 8000 USP | — | — | — | 6 | 9 | 7 |
| % release in 60 mins | <10 | >70 | >70 | >70 | >70 | >70 |

*micronized 17-hydroxyprogesterone caproate (approximate particle size distribution: d100% < 25 μm; d50% < 15 μm)

According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

The aqueous dispersion of the mixture that includes a lipophilic additive and a hydrophilic surfactant, if present, of the Examples 3 to 6 of Table-I can be hazy to non-clear when viewed with a naked eye. Their absorbance at 400 nm can be greater than 0.1, or greater than 0.3, and/or the particle size of the dispersion can be greater than 100 nm. In some aspects, the average particle size of the dispersion may be greater than 250 nm. Each of the aqueous dispersions is prepared by mixing 1 part of the mixture of the additives of the corresponding example and 99 parts of an aqueous diluent. The compositions of Example 3-6 may be prepared by mixing the additives the 17 hydroxyprogesterone caproate to get a homogenous solution or suspension. If required, the mixture may be heated (for example, to about 40° C. to about 80° C.) to get a solution or to achieve a homogenous suspension. The mixture can be disposed into a capsule. The dosage form of Example 1 and 2 has 17-hydroxyprogesterone caproate in the solid unmicronized and micronized particulate form respectively. The 17-hydroxyprogesterone caproate can be fully solubilized (as in case of Example 3) or partially solubilized (as in case of Examples 5 and 6). The formulations of Table I, if liquid, can be also formulated to be a solid dosage form by filling either as is, or admixed with a solidification aid, into a capsule. Alternatively, they can be formulated into tablets by using appropriate tableting aids.

Examples 7-10—17-hydroxyprogesterone Caproate Compositions 17-hydroxyprogesterone caproate compositions of Examples 7 through 10 can be prepared by using the ingredients shown in Table II and attain the release performance indicated.

TABLE II

| Ingredients | Example No. | | | |
|---|---|---|---|---|
| | 7 | 8 | 9 | 10 |
| | Composition in % w/w. | | | |
| 17-hydroxyprogesterone caproate (particle size >50 μm) | 90-99 | — | — | 90-99 |

TABLE II-continued

| Ingredients | Example No. | | | |
|---|---|---|---|---|
| | 7 | 8 | 9 | 10 |
| | Composition in % w/w. | | | |
| 17-hydroxyprogesterone caproate micronized* | — | 70-80 | — | — |
| 17-hydroxyprogesterone caproate (milled) | — | — | 70-80 | — |
| Lactose | 1-10 | 1-20 | 1-20 | 30 |
| Povidone K30 | 3-6 | 3-6 | 3-6 | 3-6 |
| Organic granulating solvent (example, alcohol)** | — | 0 or q.s*** | 0 or q.s*** | q.s*** |
| % release in 60 mins | <15 | >50 | >50- | >30 |

*may be substituted with nanomilled or nanosized 17-hydroxyprogesterone caproate.
**removed substantially during drying process
***Quantity sufficient for wet granulation process or for in situ formation/precipitation of fast releasing solid 17-hydroxyprogesterone caproate According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

It should be noted that the compositions of Examples 7 to 10 can be formulated to provide granules for compression into a tablet or filling in a capsule, sachet etc., with the inclusion of appropriate pharmaceutical aids such as diluents, binder, disintegrant, lubricants, flavor, etc.

Unlike Example 1 and 7, the 17-hydroxyprogesterone caproate release profile of Examples 8, 9 and 10, shown in Table II, illustrate the advantages of the smaller particle size of 17-hydroxyprogesterone caproate. These Examples further illustrate the advantages of various manufacturing processes, such as granulation, which yield solid compositions with appropriate 17-hydroxygprogesterone caproate release profiles. In some embodiments, the caproate ester in the compositions of examples in Table II can be substituted with other esters of 17-hydroxyprogesterone, such as acetate or undecanoate.

Example 11—17-hydroxyprogesterone Caproate Coated Tablets 17-hydroxyprogesterone caproate tablets of Example 7 through 10 can be further coated with a coating solution having typical composition set forth in Table III, using conventional tablet coating procedures known in the art to a weight gain of about 3 to 6%.

TABLE III

| Ingredients | Composition in % w/w |
|---|---|
| Polymer (for e.g. Hypromellose, Methocel E 5) | 8.0 |
| Plasticizer (e.g. Polyethylene glycol, NF 8000) | 0.6 |
| Coating Solvent (e.g. Ethanol) | 54.8 |
| Coating Solvent Water | 36.6 |

The coating polymer can be selected based on the need for a specific functionality to be imparted to the dosage form. For example film coating, taste masking, enteric coating protective coating, sustained release coating and so on can all be used. Unlimited examples of the polymers for use in such coatings include hypromellose, polyethylene glycol, povidone, sugars, ethyl celluloses, methacrylates, cellulose phthalates etc. Many conventional coating aids such as talc, starch, plasticizers, opacifiers, colors, flavors etc. can also be used along with coating polymers or sugars. The coating solvents can be suitably varied based on the coating polymer or sugar being applied.

Examples 12-17—17-hydroxyprogesterone Caproate Compositions

Table IV shows the 17-hydroxyprogesterone caproate compositions of Examples 12-17 that can be prepared by using the components set forth therein and the method similar to that described for Examples 3-6. The release of 17-hydroxyprogesterone caproate from the dosage form is also shown in Table IV.

TABLE IV

| Example No. Ingredients | 12 | 13 | 14 | 15 | 16 | 17 |
|---|---|---|---|---|---|---|
| | Composition % w/w | | | | | |
| 17-hydroxyprogesterone caproate | 15 | 15 | 14 | 15 | 22 | 25 |
| Lipophilic Additive . . . (example Glyceryl Caprylate/Caprate (Capmul ® MCM) | — | 85 | — | — | — | — |
| Lipophilic Additive (e.g . . . Capric Acid) | 85 | — | — | — | — | — |
| Lipophilic Additive (e.g Glyceryl Monolinoleate) | — | — | 73 | 65 | 3 | 5 |
| Hydrophilic Additive (e.g. Polyoxyl 40 Hydrogenated Castor Oil) | — | — | 13 | 15 | — | — |
| Hydrophilic Additive (e.g. Polyoxyl 35 Castor Oil) | — | — | — | — | — | 22 |
| Lipophilic Additive (e.g Glyceryl Palmitostearate; Glyceryl distearate, Precirol ® ATO 5) | — | — | — | 5 | — | — |
| Hydrophilic Additive (e.g. Tocopherol Polyethylene Glycol Succinate) | — | — | — | — | 22 | — |
| Lipophilic Additive (e.g Vitamin E; d,l-α-tocopherol) | — | — | — | — | 35 | 48 |
| Hydrophilic Additive (e.g. Hypromellose (4,000 cPs) | — | — | — | — | 18 | — |
| % release in 60 mins | >40 | >40 | >40 | >40 | >30 | >40 |

According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

The aqueous dispersion of the mixture of lipophilic additive and the hydrophilic surfactant, if present, in the examples shown in Table-IV can be hazy to non-clear when viewed with the naked eye. Their absorbance at 400 nm can be greater than 0.1, or greater than 0.3, and/or the particle size of the dispersion can be greater than 100 nm. In some aspects, the mean particle size of the dispersion may be greater than 250 nm. Each of the aqueous dispersions is prepared by mixing 1 part of the mixture of the additives of the corresponding example and 99 parts of an aqueous diluent.

The compositions of Table IV, if liquid, can be formulated to be solid dosage forms by filling into a capsule either as is, or admixed with a solidification aid such as polyethylene glycol, glyceryl distearate, wax and the like. It should be noted that these compositions can also be formulated to obtain granules for compression into a tablet or filling into a capsule, sachet etc., with the inclusion of appropriate pharmaceutical aids such as diluents, binders, disintegrants, lubricants, flavors, etc.

The 17-hydroxyprogesterone caproate in the compositions of examples in Table IV can in some embodiments be substituted with other esters of 17-hydroxyprogesterone, such as 17-hydroxyprogesterone acetate or 17-hydroxyprogesterone undecanoate.

Examples 18-23—17-hydroxyprogesterone Caproate Compositions

Table V shows various 17-hydroxyprogesterone caproate compositions as recited in Examples 18-23 that can be prepared using the components set forth therein.

TABLE V

| Example No. INGREDIENT | 18 | 19 | 20 | 21 | 22 | 23 |
|---|---|---|---|---|---|---|
| | Composition % w/w | | | | | |
| 17-hydroxyprogesterone caproate | 9 | 7 | 6 | 8 | 8 | 6 |
| Hydrophilic Surfactant (e.g. Tween 80) | 1 | 1 | 1 | 4 | 1 | 1 |
| Hydrophilic Surfactant (e.g. Sodium Lauryl Sulfate) | 4 | 4 | 3 | 1 | 4 | 3 |
| Hydrophilic Polymer (e.g. HPMC) | — | 15 | 26 | 5 | — | 25 |

TABLE V-continued

| Example No. INGREDIENT | 18 | 19 | 20 | 21 | 22 | 23 |
|---|---|---|---|---|---|---|
| | Composition % w/w | | | | | |
| Enteric Polymer (e.g. Eudragit) | — | — | — | — | — | 4 |
| Hydrophobic Polymer (e.g. Ethyl Cellulose) | — | — | — | — | 5 | — |
| Diluents/Processing Aids | 86 | 73 | 64 | 82 | 82 | 61 |
| Total | 100 | 100 | 100 | 100 | 100 | 100 |

Table VI shows various specific embodiments of different dosage forms (DF-1 to DF-9) containing 17-hydroxyprogesterone caproate that can be achieved by various combinations of the compositions shown in Table V.

According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

TABLE VI

| | Dosage Form | | | | | | | | |
|---|---|---|---|---|---|---|---|---|---|
| Composition Example No. | DF-1 | DF-2 | DF-3 | DF-4 | DF-5 | DF-6 | DF-7 | DF-8 | DF-9 |
| | Composition % w/w | | | | | | | | |
| 18 | 100 | 50 | 50 | 50 | 30 | — | — | 30 | 50 |
| 19 | — | 50 | — | — | — | — | — | — | — |
| 20 | — | — | 50 | — | — | 100 | — | 30 | — |
| 21 | — | — | — | 50 | — | — | — | 40 | 50 |
| 22 | — | — | — | — | — | — | 100 | — | — |
| 23 | — | — | — | — | 70 | — | — | — | — |
| Total | 100 | 100 | 100 | 100 | 100 | 100 | 100 | 100 | 100 |

Additional tableting methods known in the art can be used can be applied to the above exemplified compositions.
Excipients shown are exemplary of classes of excipients that can be used
The form of the drug can be interchanged with other forms such as micronized, sieved, milled, amorphous, nano, etc.

The above dosage forms DF-1 to DF-9 can be single or multiple particulate units in a capsule or as single or multiple particulate units compressed into a single tablet or multi-layer tablets. According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

Examples 24-28—17-hydroxyprogesterone Caproate Compositions

Table VII shows 17-hydroxyprogesterone caproate compositions as recited in Examples 24-28 that can be prepared using the components set forth therein, and their release performance.

TABLE VII

| | Example No. | | | | |
|---|---|---|---|---|---|
| INGREDIENT | 24 | 25 | 26 | 27 | 28 |
| | Composition (mg per dosage form) | | | | |
| 17-hydroxyprogesterone | 50 | 50 | 50 | 50 | 50 |
| Hydrophilic Surfactant (e.g. Tween 80) | 2.5 | 2.5 | 2.5 | 2.5 | 2.5 |
| Hydrophilic Surfactant (e.g. Sodium Lauryl Sulfate) | 12.5 | 12.5 | 12.5 | 12.5 | 12.5 |
| Hydrophilic Polymer (e.g. HPMC) | 125 | 65 | 90 | — | 3 |
| Enteric Polymer (e.g. Eudragit) | — | — | — | — | 5 |
| Coating Processing Aids (e.g. Plasticizer, Anti-sticking agent) | — | — | — | — | 2 |
| Diluents/Processing Aids (e.g. binder, disintegrant, diluent, glidant, lubricant) | 25 | 25 | 35 | 35 | 35 |
| Total | 215 | 155 | 190 | 100 | 110 |
| % Release in 60 minutes | >25 | >40 | >40 | 100 | >30 |

Additional tableting methods known in the art can be used can be applied to the above exemplified compositions.
Excipients shown are exemplary of classes of excipients that can be used, processing aids like binders, disintegrants, diluents, glidants, lubricants and coating aids commonly known in the art can be used.
The form of the drug can be interchanged with other forms such as micronized, sieved, milled, amorphous, nano, etc.
The above dosage forms can be single or multiple particulate units in a capsule or as single or multiple particulate units compressed as a monolithic/matrix tablet or multi-layer tablets For Example 28 the dosage form is first exposed to about 250 mL simulated gastric fluid (SGF) without enzyme for the first 30 minutes, followed by exposure to 900 mL of 0.5 wt % SLS in water at having pH about 6.8.

According to another aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

Examples 29-35—17-hydroxyprogesterone Caproate Compositions

Table VIII shows 17-hydroxyprogesterone caproate compositions and release data within 60 min for Examples 29-35 that can be prepared by using components set forth therein and the method similar to that described for Examples 12-17. Furthermore, FIGS. 2 and 3 show the release profile over the course of two hours for Examples 31 and 34 in comparison to Example 1 respectively.

TABLE VIII

| Example No. | 29 | 30 | 31 | 32 | 33 | 34 | 35 |
|---|---|---|---|---|---|---|---|
| Ingredients | Composition % w/w | | | | | | |
| 17-hydroxyprogesterone caproate | 25 | 20 | 7 | 7 | 8 | 16 | 25 |
| Lipophilic Additive (e.g. Benzyl benzoate) | 48 | 45 | — | — | — | 29 | 53 |
| Hydrophilic Additive (e.g. Benzyl alcohol) | 2 | 2 | — | — | — | — | 2 |
| Lipophilic Additive (e.g. Castor Oil) | 25 | 23 | — | — | — | — | — |
| Lipophilic Additive (e.g. Corn glycerides) | — | — | — | — | 67 | — | — |
| Lipophilic Additive (e.g. Glyceryl Caprylate/Caprate; Capmul ® MCM) | — | — | 51 | 48 | — | 17 | — |
| Lipophilic Additive (e.g. Capric Acid) | — | — | — | — | — | — | — |
| Hydrophilic Additive (e.g Polyoxyl 40 Hydrogenated Castor Oil) | — | 10 | 42 | 40 | 25 | 38 | 10 |
| Hydrophilic Additive (e.g Polyethylene glycol 8000) | — | — | — | 5 | — | — | 10 |
| % release in 60 mins | >25 | >25 | >90* | >80 | >60 | >60 | >25 |

*% released in 30 minutes

According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

The above compositions can be formulated to exhibit immediate or controlled release profiles. The aqueous dispersion of the mixture of the lipophilic additive and the hydrophilic surfactant, if present, in the examples of Table-VIII can be hazy to non-clear when viewed with the naked eye. Their absorbance at 400 nm are greater than 0.1, in some cases greater than 0.3, and/or the average particle size of the dispersion may be greater than 100 nm in some aspects. In other aspects, the average particle size of the dispersion can be greater than 250 nm. Each of the aqueous dispersions is prepared by mixing 1 part of the mixture of the additives and surfactants of the corresponding example and 99 parts of an aqueous diluent.

As can be seen from the above Examples 29, 30 and 35 by using benzyl benzoate and/or benzyl alcohol, a higher drug loading (e.g. >20% w/w 17-hydroxyprogesterone caproate) with desired release characteristics can be achieved. The 17-hydroxyprogesterone caproate can remain fully solubilized (Examples 29, 30, 31, and 33) or can be partially solubilized (Examples 32, 34 and 35) in the compositions. Further, when viewed with the naked eye the aqueous dispersion of the mixtures having a lipophilic additive and the hydrophilic surfactant, if present, as recited in Examples 29-31 and 33-35 can be hazy to non-clear. In some cases, their absorbance at 400 nm is greater than 0.1, or even greater than 0.3. Further the average particle size of the dispersion can be greater than 100 nm, or even greater than 250 nm. Each of the aqueous dispersions is prepared by mixing 1 part of the mixture of the additives and surfactants of the corresponding example and 99 parts of an aqueous diluent.

The 17-hydroxyprogesterone caproate in the compositions of examples in Table VIII can in some aspects substituted with other esters of 17-hydroxyprogesterone, such as 17-hydroxyprogesterone acetate or 17-hydroxyprogesterone undecanoate.

The compositions of example 3, 31, 32, 33, and 34 can in some aspects, also be administered as oral liquid. These compositions can also be administered orally after appropriate admixture/dilution with diluent such as water, milk, fruit juices, beverages and the like just before administration.

In certain embodiments, the contents of the above compositions can be adsorbed on some diluents and additional excipients and can be compress into tablet.

Example 36—17-hydroxyprogesterone Caproate Tablets 17-hydroxyprogesterone caproate containing granules for tableting having the components set forth in Table IX can be prepared by wet granulation methods. Accordingly, 17-hydroxyprogesterone caproate, microcrystalline cellulose and croscarmellose sodium are passed through an ASTM mesh #40 mesh sieve and mixed in a low shear granulator to form a uniform blend. A binder solution of Starch 1500 in deionized water can be used to granulate the dry powder blend to a typical granulation end-point. The wet granulate dried using a tray dryer or fluid air dryer can be sized/screened, lubricated with Aerosil 200 and magnesium stearate, and compressed into tablets.

TABLE IX

| Ingredients | Composition in % w/w |
|---|---|
| 17-hydroxyprogesterone caproate (untreated) | 28 |
| Microcrystalline Cellulose (Avicel PH 102) | 52.5 |
| Croscarmellose sodium | 10 |
| Pregelatinized starch (Starch1500) | 8 |
| Colloidal silicon dioxide (Aerosil 200) | 0.5 |
| Magnesium stearate | 1 |

The tablets of Example 36 exhibit less than 20% 17-hydroxyprogesterone caproate released in the first 60 minutes when tested using a USP Type II apparatus, 50 rpm in 900 mL of simulated intestinal fluid having 0.5% w/w sodium lauryl sulfate at 37° C. Whereas, when the micronized 17-hydroxyprogesterone caproate (with particle size d100% being about 50 μm or less) with or without surfactant is used in the above formula, at least 40% release of 17-hydroxyprogesterone caproate may be observed after the 60 minute time-point.

Examples 37-42—17-hydroxyprogesterone Caproate Compositions

Examples 37-39 of Table X have hydrophilic additives as carriers. The Examples 37, 38 and 39 therein are prepared by wet granulation process with organic solvent such as ethanol or ethanol-water as the granulating liquid. Partial or full amounts of some of hydrophilic additives therein (e.g. povidones, pluronics, surfactants etc.) can be dissolved in the granulating liquid. Optionally the ester of 17-hydroxyprogesterone (e.g. 17-hydroxyprogesterone caproate) can be solubilized or suspended in the granulating liquid. This granulating liquid can then be poured over the adsorbing hydrophilic carriers (e.g. celluloses, Lactose etc.) with low shear mixing. The granules can be dried under a gentle current of air at room temperature. The dried granules are passed through ASTM #40 mesh and filled into appropriate size capsules or compressed into tablets according to the required 17-hydroxyprogesterone caproate strength per unit dosage form.

17-hydroxyprogesterone caproate compositions of Examples 40-42 can be prepared by using the components set forth in Table X and according to the following method: The required quantities of the respective inactive component and the 17-hydroxyprogesterone caproate, are taken in a clean stainless steel container and mixed gently at about 50° C. to 70° C. using a stirrer, to get a homogenous mixture. A predetermined weight of the resulting mixture is disposed into hard gelatin capsule and allowed to solidify at room temperature.

The dosage forms of each Example 37-42 are tested for release of the 17-hydroxyprogesterone caproate using a USP Type II apparatus, at 50 rpm in 900 mL of simulated intestinal fluid having 0.5% w/w sodium lauryl sulfate at 37° C. The percent of the 17-hydroxyprogesterone caproate released from each composition is analyzed using HPLC. The results of the release testing are also shown in Table X.

It should be noted that the compositions of Examples 37-42 can be formulated to achieve tablet dosage forms with the inclusion of appropriate conventional tableting aids such as diluents, binders, disintegrants, lubricants, etc. as needed.

TABLE X

| Example No. Ingredients | 37 | 38 | 39 | 40 | 41 | 42 |
|---|---|---|---|---|---|---|
| | Composition in % w/w | | | | | |
| 17-hydroxyprogesterone caproate | 45 | 40 | 40 | 75 | 34 | 60 |
| PEG 8000 USP | — | — | — | 10 | 29 | 40 |
| Sodium Lauryl sulfate | 10 | 9 | 9 | 10 | — | — |
| Microcrystalline Cellulose*, | 45 | 40 | 37 | — | — | — |
| Pluronic F 68 | 0 | 11 | 11 | — | — | — |
| Polyvinylpyrrolidone (Povidone K 30) | 0 | 0 | 3 | 5 | 37 | — |
| % release in 60 mins | >40 | >40 | >40 | >40 | >40 | >30 |

*Magnesium alumnometasilicate (Neuslin ®), lactose and other similar substances can be used/calcium silicate According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

The in vitro 17-hydroxyprogesterone caproate release performance of Examples 37 to 42 can be seen to be superior over the release performance of the Example 36. It should be noted that in the above-recited compositions, appropriate amounts of typical pharmaceutical aids such as glidants, lubricants, anti-adherents, disintegrants and the like, can be incorporated as needed. Further, suitable amounts of hydrophilic release modifying agents (e.g. hypromellose, Eudragits etc.) may also be incorporated as needed in the compositions of Examples 37 to 42. Also, in some particular cases, when the dosage form of the Examples 37 to 42 is a tablet, appropriate functional coatings may be applied as required. It should also be noted that in some aspects the example compositions of Table X can be substituted with other esters of 17-hydroxyprogesterone (e.g. 17-hydroxyprogesterone acetate, 17-hydroxyprogesterone undecanoate, etc.)

Examples 43 and 44—17-hydroxyprogesterone Caproate Compositions 17-hydroxyprogesterone caproate compositions as recited in Examples 43 and 44 were prepared by using the components set forth in Table XI. Each of the compositions was prepared by incorporating 17-hydroxyprogesterone caproate in the molten mixture of the corresponding inactive components taken in a stainless steel container at about 35° C. to 70° C. with gentle stirring to get a free-flowing liquid mixture. A predetermined weight of the resulting liquid mixture is disposed into hard or soft gelatin capsule shells and allowed to solidify at room temperature. It should be noted that the liquid mixture can also be allowed to solidify to room temperature to get solid aggregates which may be sized through an ASTM mesh #30 to get granular particulates, which can be further filled in hard gelatin capsules or compressed into tablets.

Each of the compositions is tested for release of the 17-hydroxyprogesterone caproate using a USP Type II apparatus, at 50 rpm in 900 mL of simulated intestinal fluid having 0.5% w/w sodium lauryl sulfate at 37° C. The percent of the 17-hydroxyprogesterone caproate released from each composition is analyzed using HPLC. The results of the release testing are also shown in Table XI.

TABLE XI

| | Example No. | |
|---|---|---|
| | 43 | 44 |
| Ingredients | Composition in % w/w | |
| 17-hydroxyprogesterone caproate | 20 | 80 |
| Lipophilic additive: (e.g., Glycerol esters of $C_{12}$-$C_{18}$ fatty acids) | 80 | 20 |
| % release in 60 mins | >30% | >30% |

According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

Example 45—17-hydroxyprogesterone Caproate Spray Dried Multiparticulates 17-hydroxyprogesterone caproate multiparticulates can be prepared as follows: 15 g of a milled or micronized 17-hydroxyprogesterone caproate and lactose, mixture (95:5 w/w), are passed through ASTM mesh #60 sieve and added under mixing to about 250 mL of a solution of 8% w/v povidone K17 in water. The resulting suspension can be spray dried using a conventional spray drying equipment with settings, for example, at a heat inlet temperature of about 60-75° C. and an outlet temperature of about 30-38° C., aspirator set at 90-100%, the pump set at about 8-12 mL/min, and the flow rate set at about 500-600 L/hr. The final solid multiparticulate 17-hydroxyprogesterone caproate composition can have a compositional makeup of about 53 wt % 17-hydroxyprogesterone caproate, about 2.8 wt % lactose and about 44.2 wt % povidone K17.

According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

Example 46-50—17-hydroxyprogesterone Caproate Compositions

A mixture of 17-hydroxyprogesterone caproate and the corresponding components can be melted together to get thermosetting fill to be disposed into capsule. Alternatively, the mixture can be fed into a melt-extruder apparatus for example, a single-screw extruder (Killion, Model KLB 100) equipped with about 1 inch diameter screw and about 6 inch flex lip die, and the die opening adjusted to about 0.005 inches and the screw speed is set at about 50 rpm. The residence time of the materials within the extruder can be set for about 2 to 8 minutes. The extruded strands can be cooled to room temperature by passing over a chilled roll. The strands can then be sized through an ASTM mesh #40 and the powder disposed into capsules. The exemplary compositions for melt-extrusion are indicated in Table XII. These dosage forms can release 40% or more 17-hydroxyprogesterone caproate in about first 60 minutes. It should be noted that the 17-hydroxyprogesterone caproate compositions of Table XII can be further formulated to include one or more other substances such as lactose, starches, hydroxypropyl methyl cellulose, methacrylate, etc., at varying concentrations from about 12% to about 88% by weight of the total composition either prior to melt-extrusion or after sizing the melt-extruded composition, in order to prepare solid multiparticulates for tablets.

TABLE XII

| | Example No. | | | | |
|---|---|---|---|---|---|
| | 46 | 47 | 48 | 49 | 50 |
| Ingredients | Composition in % w/w | | | | |
| 17-hydroxyprogesterone caproate | 70 | 40 | 50 | 80 | 60 |
| Polyethylene glycol 8000 USP | 10 | — | 20 | 15 | 20 |
| (Glyceryl distearate GDS, Precirol ATO 5) | 10 | 40 | 20 | — | — |
| Stearic acid | 10 | 20 | 10 | — | — |
| Cholesterol | — | — | — | 5 | 20 |

According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

Example 51—17-hydroxyprogesterone Caproate Compositions Produced by Co-Milling

A 17-hydroxyprogesterone caproate containing composition can be prepared by co-milling (or co-grinding) 80 g 17-hydroxyprogesterone caproate along with 15 g PVP K 17 and 5 g of sodium lauryl sulfate for a period from about 12 hours to about 24 hours using a ceramic ball-mill maintained at about 20±5° C. The co-milled composition can provide a superior in vitro drug release profile which could be at least 20% more when compared to the in vitro release profile of Example 1 when tested using a USP Type II apparatus, 50 rpm in 900 mL of simulated intestinal fluid having 0.5% w/w sodium lauryl sulfate at 37° C.

According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

Example 52—17-hydroxyprogesterone Caproate Loaded Pellets 17-hydroxyprogesterone caproate coated pellets are prepared using the ingredients set forth in Table XIII A spraying solution of the coating materials can be prepared by dissolving 25 g of 17-hydroxyprogesterone caproate, 6 g of Pluronic F 68 and 5 g of PVP K 30 in about 250 mL of dehydrated alcohol. The spray solution can be intermittently sprayed on to a rolling bed of 64 g commercially available microcrystalline cellulose spheres (for example, having a mean particle size in the range of about 250 μm to about 600 μm) taken in a conventional coating pan. After all the spray solution is loaded on the spheres, it can be dried under a gentle current of air for at least 1 hour to remove the solvent. Thus, by adjusting the pan speed, spray rate and the inlet air flow and temperature, the 17-hydroxyprogesterone caproate loaded pellets or beads can be obtained which can be disposed into a capsule. Auxiliary pharmaceutical process aids such as talc, starch etc., may be dusted during the spraying process to avoid agglomeration of the pellets.

It should be noted that appropriate similar or equivalent equipment known in the art may be used for the purpose. Also, by varying the quantity of spray solution sprayed on the spheres or by varying the concentration of 17-hydroxyprogesterone caproate in the spray solution, pellets of different drug loading can be achieved.

TABLE XIII

| Ingredients | Composition in % w/w |
| --- | --- |
| 17-hydroxyprogesterone caproate | 25 |
| Pluronic F 68 | 6 |
| Polyvinylpyrrolidone K 30 | 5 |
| Dehydrated Alcohol | 250 mL |
| Microcrystalline cellulose spheres Celsphere ® | 64 |

According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

Example 53—17-hydroxyprogesterone Caproate Suspension Compositions

A homogenous suspension of 17-hydroxyprogesterone caproate prepared in a liquid vehicle having at least one non-solvent can be made by conventional processes known in the art. The suspension can be dosed as a conventional oral liquid or a known volume of the suspension may be encapsulated. Pharmaceutical aids such as suspending agents, thickening agents or viscosity modifiers, wetting agents, etc., known in the art can be used to achieve homogenous suspension of the drug in the liquid vehicle.

According to one aspect, the formulations (e.g., unit dosage forms) in the above table have from about 100 mg to 495 mg of 17HPC. According to another aspect, the formulations (e.g., unit dosage forms) in the above table have from about 150 to 450 mg of 17HPC. According to another aspect, the formulations (e.g., unit dosage forms) in the above table have from about 200 mg to 490 mg of 17HPC. According to another aspect, the formulations (e.g., unit dosage forms) in the above table have from about 505 mg to 850 mg of 17HPC. According to another aspect, the formulations (e.g., unit dosage forms) in the above table have from about 400 mg to 600 mg of 17HPC.

Example 54—17-hydroxyprogesterone Caproate Composition In Vivo Evaluation

A preliminary pharmacokinetic evaluation upon oral administration of 17-hydroxyprogesterone caproate of the current invention was carried out in male dogs. A single oral dose of 30 mg/kg and 5 mg/kg of 17-hydroxyprogesterone caproate formulated in a accordance with exemplary formulations of the present invention were used for relative bioavailability study in a fed state, compared with an intramuscular dose of 6.4 mg/kg (composition similar to commercially available Intramuscular Injection, Makena®) as positive control.

The post-dose blood levels of 17-hydroxyprogesterone caproate were monitored for 24 hours after oral dosing and for 192 hours after intramuscular injection dosing. About 2 mL of blood was drawn from the jugular, cephalic, or saphenous veins immediately before the dose was administered and at pre-determined intervals post-dose. At each time point, the blood sample was collected in a vacutainer tubes and centrifuged at about 3200 rpm for approximately 10 minutes at about 5° C. The serum obtained was analyzed by HPLC-MS/MS for 17-hydroxyprogesterone caproate. The results of the 17-hydroxyprogesterone caproate concentration in the samples are shown in Table-XIV below:

TABLE-XIV

| Dose Administered | Exemplary Oral Dosage formulations of the present invention | | IM Injection |
| --- | --- | --- | --- |
| | 30 mg/kg | 5 mg/kg | 6.4 mg/kg |
| Mean $C_{last}$ (ng/mL) | 4.51 | 0.28 | 2.54 |
| $C_{avg}$ (ng/mL) | 74 | 2.5 | 8 |
| Mean $AUC_{0-last}$ (ng*h/mL) | 1767 | 60 | 1546 |
| $AUC(ng*h\,mL^{-1})_{0-24\,h}$/Dose (mg) Ratio | 5.8 | 1.0 | — |

Contrary to reports in the literature we surprisingly found that oral compositions of the present invention provided significant blood levels ($C_{avg}$) of 17-hydroxyprogesterone caproate upon oral administration.

Example 55: Clinical Trial in Pregnant Women

Formulations (e.g., oral dosage forms like those described herein) were used in a Phase 1b open-label study that enrolled eight healthy; pregnant women at 16 to 18 weeks gestation. All subjects received three treatments in sequence. In period one, subjects received two doses of 400 mg with oral dosage forms like those described herein, administered 12 hours apart. In period two, subjects received two doses of 800 mg oral with dosage forms like those described herein, administered 12 hours apart. In period three, subjects were given 250 mg of HPC via intramuscular injection (marketed product Makena®). Blood samples were collected periodically over 24 hours following oral dosing and over 28 days following the IM dose.

The maximum concentration ("Cmax") and the area under the curve ("AUC") for the oral treatments are shown in Table below.

TABLE

Single Dose Pharmacokinetic Parameters

| Dosing Regimen (BID) (N = 7) | $C_{max}$ (ng/ml) [range] | $AUC_{0-24}$ (ng · h/ml) [range] |
|---|---|---|
| 400 mg | 21.3 [11.5-36.2] | 156 [81-234] |
| 800 mg | 63.2 [37.8-144] | 577 [323-1365] |

Results from this study demonstrate significant HPC absorption following oral administration in healthy pregnant women. Additionally, there was a more than dose proportional increase in exposure with the 800 mg dose.

Steady state pharmacokinetic parameters for oral and IM dosing regimens were simulated based on single dose data and the Cmax and AIX values are shown in the table below.

TABLE

Simulated Steady State Pharmacokinetic Parameters

| Products/ Dosing Regimen (N = 7) | $C_{ss, max}$ (ng/ml) [range] | $AUC_{SS}$ (ng · h/ml)# [range] |
|---|---|---|
| 17HPC/400 mg BID | 21.6 [12.1-36.2] | 1074 [82-229] |
| 17HPC/800 mg BID | 71.1 [43.8-144.1] | 4058 [311-1100] |
| Intramuscular injection/ 250 mg 17HPC weekly | 13.0 [6.5-29.4] | 1817 [805-3904] |

$AUC_{SS}$ calculated for post steady state 1 week duration

Based on the results shown in the Table above, oral dosing between 400 and 800 mg twice a day is expected to be comparable to the marketed 250 mg weekly IM product.

The simulated steady state PK parameters for oral and IM dosing from this were compared to simulated steady state data from previously reported results from Phase 1a study (in non-pregnant women (see Table 3).

TABLE 3

Bioavailability in pregnant and non-pregnant women

| | $AUC_{SS}$ (ng · h/ml)# | | |
|---|---|---|---|
| Study population (N) | LPCN 1107/ 400 mg BID Oral | Intramuscular Injection/250 mg weekly | Relative bioavailability [oral/IM] |
| Pregnant women (7) | 1074 | 1817 | 59% |
| Non-pregnant women (10) | 1348 | 2468 | 55% |

$AUC_{SS}$ calculated for post steady state 1 week duration

Based on the results shown in the table above, relative bioavailability of oral to IM dosing was similar between pregnant and non-pregnant women. Results from these studies are illustrated in FIG. 4.

Example 56: Powder X-Ray Diffraction

The PXRD (Powder X-Ray Diffraction (or XRD)) measurement of 17-HPC products was conducted using a Philips X'Pert X-Ray Diffractometer. The geometry for the measurement was the standard Bragg-Brentano 0-2θ geometry using a Seifert MZ IV goniometer at room temperature. Standard sample holders (22 mm diameter) were carefully filled with the powder samples. The XRPD patterns were recorded using CuKa radiation ($\lambda$=1.5406 Å) and the following measurement conditions.

1. Tube tension: 45 kV
2. Tube current: 40 mA
3. Scan Axis: Gonio
4. Start Position [° 2Th.]: 2.0125
5. End Position [° 2Th.]: 54.9875
6. Step Size [° 2Th.]: 0.0250
7. Scan Step Time [s]: 0.5000
8. Scan Type: Continuous Sample Preparation About 1 g of each micronized powdered 17-HPC API (Active Pharmaceutical Ingredient), placebo tablet and 17-HPC GMP tablet product sample were prepared for the PXRD measurement. The powdered API was used without modification. All tablets (placebo and 17-HPC containing tablet products) were ground to fine powder using a mortar and pestle set. All tablets were stored at 25° C. and 60% RH. The placebo tablet and 17-HPC tablet were stored for 2 and ¾ months after manufactured.

FIG. 5 shows the PXRD spectrograms measured for 17-HPC in Tablet (top), micronized 17-HPC API (middle), and 17-HPC reference peaks (bottom). FIG. 5 shows XRD Spectrograph measured for 17-HPC products. In FIG. 5, the top spectrogram was obtained from 17-HPC in tablet, the middle was from micronized 17-HPC API, and the bottom was from 17-HPC reference XRD Peaks. The top spectrogram (17-HPC in tablet) in FIG. 5 was calibrated by subtracting data obtained from the placebo tablet from data obtained from the 17-HPC GMP tablet. The 17-HPC reference XRD spectrogram was obtained from publically available data or databases. The peak patterns of 17-HPC molecules in the final tablet form (Top spectrogram in FIG. 5) were identical to the patterns of the micronized 17-HPC API (Middle spectrogram in FIG. 5). As a result of comparison with the reference patterns (Bottom spectrogram in FIG. 5), it is concluded that 17-HPC in the final tablet form and API are identical crystalline forms without any polymorphism or phase change.

Example 57: Exemplary Formulations Containing 17HPC

TABLE XVII

| 1. Ingredients | Composition in % w/w or [mg] | | | | | |
|---|---|---|---|---|---|---|
| | A1 | A2 | A3 | A4 | A5 | A6 |
| 17-Hydroxyprogesterone Caproate* | 10 [20] | 7 [50] | 12 [96] | 17 [133] | 19 [150] | 20 [200] |
| Carrier | 90 [180] | 93 [665] | 82 [656] | 83 [667] | 81 [650] | 80 [800] |
| Solvent | | | 6 [48] | | | |
| Total | 100 [200] | 100 [715] | 100 [800] | 100 [800] | 100 [800] | 100 [1000] |

*Can be unmilled (particle size: PS > 50 μm), milled (25 μm < PS < 50 μm, or 15 μm < PS < 25 μm), micronized (1 μm < PS < 15 μm), or nanosized (PS < 1 μm).

or

| | Ingredients | Composition in % w/w or [mg] | | | | | |
|---|---|---|---|---|---|---|---|
| | | A1 | A2 | A3 | A4 | A5 | A6 |
| | 17-Hydroxyprogesterone Caproate* | 10 [20] | 7 [50] | 12 [96] | 17 [133] | 19 [150] | 20 [200] |
| Carrier: | Lipophilic additive (e.g. Glyceryl monolinoleate, Glyceryl caprylate/caprate, etc) | 90 [180] | 51 [365] | 75 [600] | 75 [600] | 69 [555] | 70 [700] |
| | Hydrophilic additive (e.g. Cremophor, PEG) | | 42 [300] | 7 [56] | 6 [51] | 6 [45] | 5 [50] |
| | Flow aid/disintegrant (e.g. Colloidal Silicon Dioxide, Stearic acid, Magnesium stearate) | | | | 2 [16] | | |
| | Non-ionic surfactant (e.g. Tween, Span, etc) | | | | | 6 [50] | |
| | Anionic surfactant (e.g. Sodium Lauryl Sulfate, etc) | | | | | | 5 [50] |
| | Solvent (e.g. Benzyl Benzoate, Benzyl alcohol, water, etc) | | | 6 [48] | | | |
| | Total | 100 [200] | 100 [715] | 100 [800] | 100 [800] | 100 [800] | 100 [1000] |

TABLE XVIII

| Ingredients | Composition in % w/w or [mg] | | | | | |
|---|---|---|---|---|---|---|
| | B1 | B2 | B3 | B4 | B5 | B6 |
| 17-Hydroxyprogesterone Caproate* | 26 [150] | 31 [200] | 33 [250] | 33 [300] | 35 [400] | 40 [450] |
| Carrier | 25 [143] | 69 [450] | 67 [500] | 67 [667] | 65 [750] | 60 [675] |
| Solvent | 49 [282] | | | | | |
| Total | 100 [575] | 100 [650] | 100 [750] | 100 [910] | 100 [1150] | 100 [1125] |

*Can be unmilled (particle size: PS > 50 μm), milled (25 μm < PS < 50 μm, or 15 μm < PS < 25 μm), micronized (1 μm < PS < 15 μm), or nanosized (PS < 1 μm).

or

| Ingredients | Composition in % w/w or [mg] | | | | | |
|---|---|---|---|---|---|---|
| | B1 | B2 | B3 | B4 | B5 | B6 |
| 17-Hydroxyprogesterone Caproate* | 26 [150] | 31 [200] | 33 [250] | 33 [300] | 35 [400] | 40 [450] |

TABLE XVIII-continued

| Carrier: | | | | | | | |
|---|---|---|---|---|---|---|---|
| | Lipophilic additive (e.g. Glyceryl monolinoleate, Glyceryl caprylate/caprate, etc) | 13 [75] | 61 [400] | 27 [200] | | | |
| | Hydrophilic additive (e.g. Cremophor, PEG) | 12 [68] | | 27 [200] | | | |
| | Disintegrant (e.g. Ac-di-sol, Crospovidone, etc) | | | | 16 [140] | 30 [345] | 25 [281] |
| | EASYtab SP** (Binder/flow aid/disintegrant) | | | | 51 [460] | 30 [345] | 30 [338] |
| | Non-ionic Surfactant (e.g. Polysorbate, Span, etc) | | | 13 [100] | | | 5 [56] |
| | Anionic Surfactant (e.g. Sodium Lauryl Sulfate, etc) | | 8 [50] | | | 5 [60] | |
| | Solvent (e.g. Benzyl Benzoate, Benzyl alcohol, water, etc) | 49 [282] | | | | | |
| | Total | 100 [575] | 100 [650] | 100 [750] | 100 [910] | 100 [1150] | 100 [1125] |

**Commercial all-in-one excipient composite consisting of microcrystalline cellulose (95.0-98.0%), colloidal silicon dioxide (1.5-2.5%), sodium starch glycolate (0.5-2.0%), and sodium stearyl fumarate (0.3-1.0%).

TABLE XIX

| | Composition in % w/w or [mg] | | | | | |
|---|---|---|---|---|---|---|
| Ingredients | C1 | C2 | C3 | C4 | C5 | C6 |
| 17-Hydroxyprogesterone Caproate* | 46 [600] | 49 [850] | 55 [800] | 58 [700] | 65 [500] | 75 [150] |
| Carrier | 54 [700] | 51 [900] | 45 [650] | 42 [500] | 35 [265] | 25 [50] |
| Solvent | qs | qs | qs | qs | qs | qs |
| Total | 100 [1300] | 100 [1750] | 100 [1450] | 100 [1200] | 100 [765] | 100 [200] |

*Can be unmilled (particle size: PS > 50 μm), milled (25 μm < PS < 50 μm, or 15 μm < PS < 25 μm), micronized (1 μm < PS < 15 μm), or nanosized (PS < 1 μm).

or

| | | Composition in % w/w or [mg] | | | | | |
|---|---|---|---|---|---|---|---|
| Ingredients | | C1 | C2 | C3 | C4 | C5 | C6 |
| 17-Hydroxyprogesterone Caproate* | | 46 [600] | 49 [850] | 56 [800] | 59 [700] | 65 [500] | 75 [150] |
| Carrier: | Diluent/filler | 25 [325] | 14 [245] | | 15 [180] | | |
| | Binder/adhesive | 20 [260] | 20 [355] | | 7 [82] | | |
| | Disintegrant | 8 [104] | 4 [70] | 16 [228] | 3 [38] | 10 [75] | 1 [2] |
| | Lubricant/glidant | 1 [11] | 1 [15] | | | 1 [8] | |
| | EASYtab SP (Binder/flow aid/disintegrant) | | 6 [105] | 11 [155] | 8 [100] | 10 [75] | |
| | Non-ionic Surfactant (e.g. Polysorbate, Span, etc) | | 6 [110] | | 4 [50] | 14 [107] | |
| | Anionic Surfactant (e.g. Sodium Lauryl Sulfate, etc) | | | 17 [242] | 4 [50] | | 24 [48] |
| | Solvent | qs | qs | qs | qs | qs | qs |
| | Total | 100 [1300] | 100 [1750] | 100 [1425] | 100 [1200] | 100 [765] | 100 [200] |

TABLE XIX-continued and

| | | Composition in % w/w or [mg] | | | | | | |
|---|---|---|---|---|---|---|---|---|
| Ingredients | | C7 | C8 | C9 | C10 | C11 | C12 | C13 | C14 |
| 17-Hydroxyprogesterone Caproate* | | 49 [475] | 44 [500] | 50 [500] | 47 [550] | 52 [550] | 48 [575] | 49 [600] | 54 [600] |
| Carrier | | 51 [500] | 56 [625] | 50 [500] | 53 [675] | 48 [500] | 52 [625] | 51 [625] | 46 [500] |
| Solvent | | qs | qs | qs | qs | qs | qs | qs | qs |
| Total | | 100 [975] | 100 [1125] | 100 [1000] | 100 [1175] | 100 [1050] | 100 [1200] | 100 [1225] | 100 [1100] |

*Can be unmilled (particle size: PS > 50 mm), milled (25 mm < PS < 50 mm, or 15 mm < PS < 25 mm), micronized (1 mm < P5 < 15 mm), or nanosized (PS < 1 mm).

or

| | | Composition in % w/w or [mg] | | | | | | |
|---|---|---|---|---|---|---|---|---|
| Ingredients | | C7 | C8 | C9 | C10 | C11 | C12 | C13 | C14 |
| 17-Hydroxyprogesterone Caproate* | | 49 [475] | 44 [500] | 50 [500] | 47 [550] | 52 [550] | 48 [575] | 49 [600] | 54 [600] |
| Carrier: | Disintegrant | 17 [170] | 20 [228] | 17 [170] | 19 [228] | 16 [170] | 16 [190] | 19 [228] | 10 [115] |
| | Lubricant/glidant | 1 [10] | | | | | 1 [15] | | 1 [10] |
| | EASYtab SP | 28 [270] | 14 [155] | 28 [280] | 13 [155] | 27 [280] | 20 [240] | 12 [147] | 25 [275] |
| | Non-ionic Surfactant (Tween, Span, etc) | 5 [50] | | | | | | | 5 [50] |
| | Anionic Surfactant (Sodium lauryl sulfate, etc) | | 22 [242] | 5 [50] | 21 [242] | 5 [50] | 15 [180] | 20 [240] | 5 [50] |
| | Solvent | qs | qs | qs | qs | qs | qs | qs | qs |
| Total | | 100 [975] | 100 [1125] | 100 [1000] | 100 [1175] | 100 [1050] | 100 [1200] | 100 [1225] | 100 [1100] |

Example 58: Clinical Study

The study was an open-label, four-period, four-treatment, randomized, single and multiple dose, PK study in pregnant women of three dose levels of an oral pharmaceutical composition as described herein (containing 17HPC e.g., as described in the Examples or elsewhere herein) and injectable HPC (Makena®). The study enrolled 12 healthy pregnant women (average age of 27 years) with a gestational age of approximately 16 to 19 weeks. Subjects received three dose levels of the oral pharmaceutical composition having 17HPC (400 mg BID, 600 mg BID, or 800 mg BID) in a randomized, crossover manner during the first three treatment periods and then received five weekly injections of HPC during the fourth treatment period. During each of the treatment periods with the oral pharmaceutical composition having 17HPC, subjects received an oral single dose of 17HPC on Day 1 followed by twice daily administration from Day 2 to Day 8. Following completion of the three treatment periods with the oral pharmaceutical composition having 17HPC, and a washout period, all subjects received five weekly injections of HPC.

Average steady state 17HPC levels (Cavg0-24) were comparable or higher for all three oral doses than for injectable HPC. HPC levels as a function of daily dose were linear for the three doses with the oral pharmaceutical composition having 17HPC. Unlike the injectable HPC, steady state exposure was achieved for all three doses with the oral pharmaceutical composition having 17HPC, within seven days. The approved HPC injectable product is a single fixed dose product that does not allow for dose adjustments.

A previous literature study of 250 mg injectable HPC in pregnant women reported that the lowest preterm birth rates were seen when median HPC concentrations exceeded 6.4 ng/mL and that the plasma concentrations of HPC ranged between 3.7 to 56 ng/mL with the injectable HPC. With all three doses tested with the oral pharmaceutical composition having 17HPC, HPC exposure (Cavg0-24) did not fall below 6.4 ng/ml in any study subject.

The oral pharmaceutical composition having 17HPC was well tolerated across the three dose levels. No adverse drug reactions, serious adverse events, or deaths were reported during the study. There was dose linearity and short duration to steady state demonstrated in this study which unexpectedly allows dose adjustments with the oral pharmaceutical composition having 17HPC, during the course of therapy (e.g., on a sufficient time scale) to improve or modulate outcome. There was good correlation of Cmax to Cavg and Cavg to pre-dose C value which enables single point titration (e.g., based on serum or plasma 17HPC levels at a single time point with 0-12 hours after single dose administration at steady state (e.g., at 0.5, 1, 1.5, 2, 2.5, 3, 3.5, 4, 4.5, 5, 5.5, 6, 6.5, 7, 7.5, 8, 8.5, 9, 9.5, 10, 10.5, 11, or 11.5 hours after single dose administration (or within a range defined by any two of these values, or within a range of within 0.5 h or 1 h of any one of these values))).

For example, a pregnant female at risk for preterm birth is administered orally, a pharmaceutical composition (e.g., as described herein), in an initial dosing regimen, until steady state is achieved (e.g., 5 or more days, 6 or more days, 7 or more days). The initial dosing regimen can be e.g., 400 mg per day, 450 mg per day, 500 mg per day, 550 mg per day, 600 mg per day, 650 mg per day, 700 mg per day, 750 mg per day, 800 mg per day, 850 mg per day, 900 mg per day, 950 mg per day, 1000 mg per day, 1150 mg per day, 1200 mg per day, 1250 mg per day, 1300 mg per day, 1350 mg per day, 1400 mg per day, 1450 mg per day, 1500 mg per day, 1550 mg per day, 1600 mg per day, 1650 mg per day, 1700 mg per day, 1750 mg per day, 1800 mg per day, 1850 mg per day, 1900 mg per day, 1950 mg per day or 2000 mg per day (or within a range defined by any two of these values, or within a range of within 50 mg or 100 mg of any one of these values) e.g., on a once, twice, thrice, or four times a day dosing regime. After single dose administration at steady state, the plasma or serum 17HPC in the subject is determined and if the levels are too low, the daily dose is increased, if the levels are too high, the daily dose is increased or if they levels are appropriate, the daily dose is maintained. The pharmaceutical composition can delivery the daily dose in e.g., 1, 2, 3, 4, 5, 6, 7, 8, 9, 10, 11, 12, 13, 14, 15 or 16 unit dosage forms per day. In one aspect, the oral pharmaceutical composition comprises 17-hydroxyprogesterone caproate and a pharmaceutically acceptable carrier, wherein, when measured using a USP Type-II dissolution apparatus in 900 mL of simulated intestinal fluid having 0.5% w/w sodium lauryl sulfate at 50 RPM at 37° C., at least 20% of the 17-hydroxyprogesterone caproate is released from the oral composition at 60 minutes. In one aspect, the oral pharmaceutical composition, comprises: 17-hydroxyprogesterone caproate, and a pharmaceutically acceptable carrier including at least a hydrophilic surfactant. In one aspect, the oral pharmaceutical composition, comprises: 17-hydroxyprogesterone caproate having a mean particulate diameter of about 50 micron or less, and a pharmaceutically acceptable carrier including at least a hydrophilic surfactant. In one aspect, the oral pharmaceutical composition, comprises: 17-hydroxyprogesterone caproate having a mean particulate diameter of about 50 micron or less, and a pharmaceutically acceptable carrier including at least a hydrophilic surfactant wherein, when measured using a USP Type-II dissolution apparatus in 900 mL of simulated intestinal fluid having 0.5% w/w sodium lauryl sulfate at 50 RPM at 37° C., at least 20% of the 17-hydroxyprogesterone caproate is released from the oral composition at 60 minutes. In one aspect, the oral pharmaceutical composition, comprises: 17-hydroxyprogesterone caproate having a mean particulate diameter of about 50 micron or less, and a pharmaceutically acceptable carrier including at least a hydrophilic surfactant; wherein the amount of the 17-hydroxyprogesterone caproate is from about 5% to about 80% w/w of the total composition; and wherein, when measured using a USP Type-II dissolution apparatus in 900 mL of simulated intestinal fluid having 0.5% w/w sodium lauryl sulfate at 50 RPM at 37° C., at least 20% of the 17-hydroxyprogesterone caproate is released from the oral composition at 60 minutes. In one aspect, the oral pharmaceutical composition comprises a hydrophilic surfactant which is an ionic hydrophilic surfactant. In one aspect, the oral pharmaceutical composition comprises a hydrophilic surfactant which is a non-ionic hydrophilic surfactant. In one aspect, the oral pharmaceutical composition comprises a hydrophilic surfactant which is a poloxamer, a polyethylene glycol sorbitan fatty acid ester, a sorbitan fatty acid ester, a polyethylene glycol glycerol fatty acid ester or a combination thereof. In one aspect, the oral pharmaceutical composition comprises a hydrophilic surfactant, which is sodium lauryl sulfate, sodium dioctyl sulfosuccinate, a lecithin, a bile salt or a combination thereof. In one aspect, the oral pharmaceutical composition further comprises polyvinylpyrrolidone, croscarmellose, microcrystalline cellulose, magnesium stearate, silicon dioxide, stearic acid, mannitol, a polyvinyl alcohol copolymer, a polyvinylpyrrolidone copolymer, a polyethylene glycol copolymer, a methacrylic acid copolymer, or a combination thereof. In one aspect, the oral pharmaceutical composition is formulated as a powder, granulate, particulate, bead, pellet, sprinkle, suspension, solution, tablet, capsule, or a combination thereof. In one aspect, the oral pharmaceutical composition is formulated as a capsule. In one aspect, the oral pharmaceutical composition is formulated as a tablet. In one aspect, the oral pharmaceutical composition comprises an amount of 17-hydroxyprogesterone caproate equivalent to from about 20 mg to about 400 mg of 17-hydroxyprogesterone. In one aspect, the oral pharmaceutical composition has from about 20 mg to about 800 mg 17-hydroxyprogesterone caproate. In one aspect, the oral pharmaceutical composition has from about 10 mg to about 300 mg 17-hydroxyprogesterone caproate.

Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, but not limited to, variations in size, materials, shape, form, function and manner of operation, assembly and use may be made without departing from the principles and concepts set forth herein.

What is claimed is:

1. An oral pharmaceutical composition comprising or prepared from:
    a therapeutically effective amount of particulate form 17HPC, and a pharmaceutically acceptable carrier, said therapeutically effective amount of 17HPC ranging from 150 mg to 750 mg and having a D90 particle diameter of no more than about 200 nm, wherein administration of said composition to a subject results in at least one of a bioavailability ratio of greater than 2.0 when comparing an 800 mg BID dose to a 400 mg BID dose, and a $C_{avg}$ in said subject of greater than 6.4 ng/mL.

2. The oral pharmaceutical composition of claim 1, wherein the composition releases greater than 10% after 1 hour when tested using a USP Type II apparatus at 50 rpm in an aqueous media having 1.5× or greater sink condition at 37.0° C. (±0.5).

3. The oral pharmaceutical composition of claim 1, wherein the composition releases greater than 10% after 1 hour when tested using a USP Type II apparatus at 50 rpm in an aqueous media having 3× or greater sink condition at 37.0° C. (+0.5).

4. The oral pharmaceutical composition of claim 1, wherein the composition has at least 225 mg of 17HPC.

5. The oral pharmaceutical composition of claim 1, wherein said pharmaceutically acceptable carrier comprises one or more of a diluent, binder, disintegrant, lubricant or surfactant.

6. The oral pharmaceutical composition of claim 1, wherein said pharmaceutically acceptable carrier comprises a lipophilic or hydrophilic additive.

7. The oral pharmaceutical composition of claim 1, wherein said pharmaceutically acceptable carrier comprises a lipophilic or hydrophilic surfactant.

8. The oral pharmaceutical composition of claim 1, wherein said pharmaceutically acceptable carrier comprises a lipophilic surfactant and a hydrophilic surfactant.

9. The oral pharmaceutical composition of claim 1, wherein said pharmaceutically acceptable carrier comprises a non-ionic or ionic surfactant.

10. The oral pharmaceutical composition of claim 1, wherein said 17HPC comprises at least one form of fully solubilized, partially solubilized, crystalline particulate, amorphous particulate, and a combination thereof.

11. The oral pharmaceutical composition of claim 1, wherein said particulate form of 17HPC has a mean particle diameter of less than about 60 nm.

12. The oral pharmaceutical composition of claim 1, wherein the composition has a crystallization inhibitor or a particle agglomeration inhibitor.

13. The oral pharmaceutical composition of claim 1, wherein the composition is a powder, granulate, particulate, bead, pellet, sprinkle, suspension, solution, tablet, caplet, capsule, or a combination thereof.

14. The oral pharmaceutical composition of claim 1, wherein the composition is controlled release or immediate release.

15. The oral pharmaceutical composition of claim 1, wherein the composition is a coated or uncoated tablet or caplet.

16. The oral pharmaceutical composition of claim 1, wherein the composition is a monolithic or multilayered tablet.

17. The oral pharmaceutical composition of claim 1, which when administered once, twice or three times a day as one to twelve unit dosage forms total per day to a human subject, provides a 17HPC $C_{avg-24h}$ of greater than at least one of 0.1, 0.5 and 1.0 ng/mL.

18. A method of treatment comprising administering to a subject an oral pharmaceutical composition comprising or prepared from:
 a therapeutically effective amount of particulate form 17HPC comprising from 150 mg to 750 mg of 17HPC having a D90 particle diameter of no more than about 200 nm, a pharmaceutically acceptable carrier, and one or more additional agents chosen from pharmaceutical agents, vitamins, minerals, supplements, wherein said administration results in at least one of a bioavailability ratio of greater than 2.0 when comparing an 800 mg BID dose to a 400 mg BID dose, and a $C_{avg}$ in said subject of greater than 6.4 ng/mL.

19. The method of claim 18, wherein said method comprises administering said pharmaceutical composition once, twice or three times a day as one to twelve unit dosage forms total per day to a human subject, resulting in a 17HPC $C_{avg-24h}$ of greater than at least one of 0.1, 0.5 and 1.0 ng/mL in said human subject.

20. The method of claim 19, wherein said particulate form of 17HPC has a mean particle diameter of less than about 60 nm.

\* \* \* \* \*